(12) United States Patent
Nawana et al.

(10) Patent No.: US 12,214,346 B2
(45) Date of Patent: Feb. 4, 2025

(54) DERMAL PATCH WITH A DIAGNOSTIC TEST STRIP

(71) Applicant: Satio, Inc., Boston, MA (US)

(72) Inventors: Namal Nawana, Weston, MA (US); Ziad Tarik Al-Shamsie, San Diego, CA (US)

(73) Assignee: Satio, Inc., Boston, MA (US)

( * ) Notice: Subject to any disclaimer, the term of this patent is extended or adjusted under 35 U.S.C. 154(b) by 0 days.

(21) Appl. No.: 18/090,063

(22) Filed: Dec. 28, 2022

(65) Prior Publication Data

US 2023/0142316 A1 May 11, 2023

Related U.S. Application Data

(63) Continuation-in-part of application No. 17/994,454, filed on Nov. 28, 2022, now Pat. No. 11,877,848, and
(Continued)

(51) Int. Cl.
*A61B 5/151* (2006.01)
*B01L 3/00* (2006.01)

(52) U.S. Cl.
CPC ........ *B01L 3/5023* (2013.01); *A61B 5/15109* (2013.01); *B01L 2200/04* (2013.01); *B01L 2200/10* (2013.01); *B01L 2200/16* (2013.01); *B01L 2300/023* (2013.01); *B01L 2300/044* (2013.01); *B01L 2300/0672* (2013.01); *B01L 2300/069* (2013.01); *B01L 2300/0825* (2013.01); *B01L 2400/049* (2013.01)

(58) Field of Classification Search
CPC ............... B01L 3/5023; B01L 2200/04; B01L 2200/10; B01L 2200/16; B01L 2300/023; B01L 2300/044; A61B 5/15109

USPC ......................................................... 600/309
See application file for complete search history.

(56) References Cited

U.S. PATENT DOCUMENTS 5,015,228 A  5/1991 Columbus et al.
5,338,308 A  8/1994 Wilk
(Continued)

FOREIGN PATENT DOCUMENTS

AU  2006283345 A1  3/2007
AU  2006283345 B2  3/2007
(Continued)

OTHER PUBLICATIONS

English machine translation of JP-2004024164-A, patents.google.com, 8 pages.
(Continued)

*Primary Examiner* — Phillip A Gray
(74) *Attorney, Agent, or Firm* — Potomac Law Group, PLLC; Reza Mollaaghababa

(57) ABSTRACT

A system for analyzing a physiological sample includes a cartridge configured to attach to the skin of a subject. The cartridge includes: a processing fluid pack that is configured to release a processing fluid stored therein, a diagnostic test strip, and a vacuum pin. The system also includes a lancet with a needle. The lancet is configured to deploy the needle upon engagement with the cartridge to draw a physiological sample from the subject. The vacuum pin is configured to create a vacuum within the cartridge to draw the released processing fluid and the drawn physiological sample to the diagnostic test strip.

17 Claims, 59 Drawing Sheets

Related U.S. Application Data a continuation-in-part of application No. 17/991,284, filed on Nov. 21, 2022, now Pat. No. 12,048,543, and a continuation-in-part of application No. 17/971,142, filed on Oct. 21, 2022, now Pat. No. 12,053,284, and a continuation-in-part of application No. 17/903,802, filed on Sep. 6, 2022, and a continuation-in-part of application No. 17/500,873, filed on Oct. 13, 2021, now Pat. No. 11,964,121.

(56) References Cited

U.S. PATENT DOCUMENTS

| | | |
|---|---|---|
| 5,441,490 A | 8/1995 | Svedman |
| 5,527,288 A | 6/1996 | Gross et al. |
| 5,602,037 A | 2/1997 | Ostgaard et al. |
| 5,636,640 A | 6/1997 | Staehlin |
| 5,680,872 A | 10/1997 | Sesekura et al. |
| 5,848,991 A | 12/1998 | Gross et al. |
| 5,997,501 A | 12/1999 | Gross et al. |
| 6,234,980 B1 | 5/2001 | Bell |
| 6,315,985 B1 | 11/2001 | Wu et al. |
| 6,454,140 B1 | 9/2002 | Jinks |
| 6,500,150 B1 | 12/2002 | Gross et al. |
| 6,506,168 B1 | 1/2003 | Fathallah et al. |
| 6,524,284 B1 | 2/2003 | Marshall |
| 6,610,273 B2 | 8/2003 | Wu et al. |
| 6,623,457 B1 | 9/2003 | Rosenberg |
| 6,644,517 B2 | 11/2003 | Thiel et al. |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,796,429 B2 | 9/2004 | Cameron et al. |
| 6,808,506 B2 | 10/2004 | Lastovich et al. |
| 6,893,655 B2 | 5/2005 | Flanigan et al. |
| 6,932,082 B2 | 8/2005 | Stein |
| 6,960,193 B2 | 11/2005 | Rosenberg |
| 6,994,691 B2 | 2/2006 | Ejlersen |
| 7,004,928 B2 | 2/2006 | Aceti et al. |
| 7,083,592 B2 | 8/2006 | Lastovich et al. |
| 7,101,534 B1 | 9/2006 | Schultz et al. |
| 7,156,838 B2 | 1/2007 | Gabel et al. |
| 7,175,642 B2 | 2/2007 | Briggs et al. |
| 7,182,955 B2 | 2/2007 | Hart et al. |
| 7,250,037 B2 | 7/2007 | Shermer et al. |
| 7,252,651 B2 | 8/2007 | Haider et al. |
| 7,282,058 B2 | 10/2007 | Levin et al. |
| 7,308,893 B2 | 12/2007 | Boot |
| 7,435,415 B2 | 10/2008 | Gelber |
| 7,637,891 B2 | 12/2009 | Wall |
| 7,651,475 B2 | 1/2010 | Angel et al. |
| 7,678,079 B2 | 3/2010 | Shermer et al. |
| 7,846,488 B2 | 12/2010 | Johnson et al. |
| 7,905,866 B2 | 3/2011 | Haider et al. |
| 8,048,019 B2 | 11/2011 | Nisato et al. |
| 8,057,842 B2 | 11/2011 | Choi et al. |
| 8,066,680 B2 | 11/2011 | Alchas et al. |
| 8,079,960 B2 | 12/2011 | Briggs et al. |
| 8,104,469 B2 | 1/2012 | Dams |
| 8,108,023 B2 | 1/2012 | Mir et al. |
| 8,157,768 B2 | 4/2012 | Haider et al. |
| 8,206,336 B2 | 6/2012 | Shantha |
| 8,246,582 B2 | 8/2012 | Angel et al. |
| 8,246,893 B2 | 8/2012 | Ferguson et al. |
| 8,252,268 B2 | 8/2012 | Slowey et al. |
| 8,267,889 B2 | 9/2012 | Cantor et al. |
| 8,303,518 B2 | 11/2012 | Aceti et al. |
| D681,195 S | 4/2013 | Skulley et al. |
| 8,409,140 B2 | 4/2013 | Ejlersen et al. |
| 8,414,503 B2 | 4/2013 | Briggs et al. |
| 8,414,959 B2 | 4/2013 | Hye-Ok et al. |
| 8,430,097 B2 | 4/2013 | Jinks et al. |
| 8,459,253 B2 | 6/2013 | Howgill |
| 8,491,500 B2 | 7/2013 | Briggs et al. |
| 8,496,601 B2 | 7/2013 | Briggs et al. |
| D687,550 S | 8/2013 | Moeckly et al. |
| D687,551 S | 8/2013 | Moeckly et al. |
| D687,945 S | 8/2013 | Brewer et al. |
| D687,946 S | 8/2013 | Brewer et al. |
| D687,947 S | 8/2013 | Brewer et al. |
| 8,512,244 B2 | 8/2013 | Jennewine |
| 8,517,019 B2 | 8/2013 | Brewer et al. |
| 8,554,317 B2 | 10/2013 | Duan |
| 8,556,861 B2 | 10/2013 | Tsals |
| 8,561,795 B2 | 10/2013 | Schott |
| D693,921 S | 11/2013 | Burton et al. |
| 8,602,271 B2 | 12/2013 | Winker et al. |
| 8,603,040 B2 | 12/2013 | Haider et al. |
| 8,608,889 B2 | 12/2013 | Sever et al. |
| 8,622,963 B2 | 1/2014 | Iwase et al. |
| 8,696,619 B2 | 4/2014 | Schnall |
| 8,696,637 B2 | 4/2014 | Ross |
| D705,422 S | 5/2014 | Burton et al. |
| 8,715,232 B2 | 5/2014 | Yodfat et al. |
| 8,740,014 B2 | 6/2014 | Purkins et al. |
| 8,741,377 B2 | 6/2014 | Choi et al. |
| 8,784,363 B2 | 7/2014 | Frederickson et al. |
| 8,808,202 B2 | 8/2014 | Brancazio |
| 8,808,786 B2 | 8/2014 | Jinks et al. |
| 8,814,009 B2 | 8/2014 | Hodson et al. |
| 8,814,035 B2 | 8/2014 | Stuart |
| 8,821,412 B2 | 9/2014 | Gonzalez-Zugasti et al. |
| 8,821,446 B2 | 9/2014 | Trautman et al. |
| 8,821,779 B2 | 9/2014 | Ferguson et al. |
| 8,827,971 B2 | 9/2014 | Gonzalez-Zugasti et al. |
| 8,870,821 B2 | 10/2014 | Laufer |
| 8,900,180 B2 | 12/2014 | Wolter et al. |
| 8,900,194 B2 | 12/2014 | Clarke et al. |
| 8,945,071 B2 | 2/2015 | Christensen |
| 8,961,431 B2 | 2/2015 | Roe et al. |
| 9,022,973 B2 | 5/2015 | Sexton et al. |
| 9,033,898 B2 | 5/2015 | Chickering, III et al. |
| 9,041,541 B2 | 5/2015 | Levinson et al. |
| D733,290 S | 6/2015 | Burton et al. |
| 9,067,031 B2 | 6/2015 | Jinks et al. |
| 9,072,664 B2 | 7/2015 | Stein et al. |
| 9,089,661 B2 | 7/2015 | Stuart et al. |
| 9,089,677 B2 | 7/2015 | Soo et al. |
| 9,113,836 B2 | 8/2015 | Bernstein et al. |
| 9,119,578 B2 | 9/2015 | Haghgooie et al. |
| 9,119,945 B2 | 9/2015 | Simons et al. |
| 9,133,024 B2 | 9/2015 | Phan et al. |
| 9,144,651 B2 | 9/2015 | Stuart |
| 9,144,671 B2 | 9/2015 | Cantor et al. |
| 9,173,994 B2 | 11/2015 | Ziaie et al. |
| 9,174,035 B2 | 11/2015 | Ringsred et al. |
| 9,186,097 B2 | 11/2015 | Frey et al. |
| 9,227,021 B2 | 1/2016 | Buss |
| 9,289,763 B2 | 3/2016 | Berthier et al. |
| 9,289,925 B2 | 3/2016 | Ferguson et al. |
| 9,289,968 B2 | 3/2016 | Sever et al. |
| 9,295,417 B2 | 3/2016 | Haghgooie et al. |
| 9,295,987 B2 | 3/2016 | Kelly et al. |
| 9,339,956 B2 | 5/2016 | Rendon |
| 9,380,972 B2 | 7/2016 | Fletcher et al. |
| 9,380,973 B2 | 7/2016 | Fletcher et al. |
| 9,468,404 B2 | 10/2016 | Hayden |
| 9,480,428 B2 | 11/2016 | Colin et al. |
| 9,504,813 B2 | 11/2016 | Buss |
| 9,522,225 B2 | 12/2016 | Chong et al. |
| 9,549,700 B2 | 1/2017 | Fletcher et al. |
| 9,555,187 B2 | 1/2017 | Sonderegger et al. |
| 9,566,393 B2 | 2/2017 | Iwase et al. |
| 9,579,461 B2 | 2/2017 | Sonderegger et al. |
| 9,623,087 B2 | 4/2017 | Zhang et al. |
| 9,642,895 B2 | 5/2017 | Dai et al. |
| 9,643,229 B2 | 5/2017 | Wilson et al. |
| 9,675,675 B2 | 6/2017 | Zhang et al. |
| 9,675,752 B2 | 6/2017 | Christensen |
| 9,682,222 B2 | 6/2017 | Burton et al. |
| 9,693,950 B2 | 7/2017 | Determan et al. |
| 9,694,149 B2 | 7/2017 | Jinks et al. |
| 9,717,850 B2 | 8/2017 | Sonderegger |
| 9,724,462 B2 | 8/2017 | Rotem |
| 9,730,624 B2 | 8/2017 | Gonzalez-Zugasti et al. |

(56) References Cited

U.S. PATENT DOCUMENTS

| | | |
|---|---|---|
| 9,770,578 B2 | 9/2017 | Chowdhury |
| 9,775,551 B2 | 10/2017 | Bernstein et al. |
| 9,782,574 B2 | 10/2017 | Simmers |
| 9,789,249 B2 | 10/2017 | Frederickson et al. |
| 9,789,299 B2 | 10/2017 | Simmers |
| 9,844,631 B2 | 12/2017 | Bureau |
| 9,849,270 B2 | 12/2017 | Stockholm |
| D808,515 S | 1/2018 | Atkin et al. |
| 9,861,580 B2 | 1/2018 | Mueting et al. |
| 9,861,801 B2 | 1/2018 | Baker et al. |
| 9,872,975 B2 | 1/2018 | Burton et al. |
| 9,884,151 B2 | 2/2018 | Sullivan et al. |
| 9,895,520 B2 | 2/2018 | Burton et al. |
| 9,956,170 B2 | 5/2018 | Cantor et al. |
| 9,968,767 B1 | 5/2018 | Hasan et al. |
| 9,987,629 B2 | 6/2018 | Berthier et al. |
| 9,993,189 B2 | 6/2018 | Phan et al. |
| 10,004,887 B2 | 6/2018 | Gross et al. |
| 10,010,676 B2 | 7/2018 | Bureau |
| 10,010,706 B2 | 7/2018 | Gonzalez et al. |
| 10,010,707 B2 | 7/2018 | Colburn et al. |
| 10,016,315 B2 | 7/2018 | Letourneau et al. |
| 10,029,845 B2 | 7/2018 | Jinks |
| 10,035,008 B2 | 7/2018 | Brandwein et al. |
| 10,076,649 B2 | 9/2018 | Gilbert et al. |
| 10,080,843 B2 | 9/2018 | Bureau |
| 10,080,846 B2 | 9/2018 | Sonderegger et al. |
| 10,099,043 B2 | 10/2018 | Berry et al. |
| 10,105,524 B2 | 10/2018 | Meyer et al. |
| 10,111,807 B2 | 10/2018 | Baker et al. |
| D834,704 S | 11/2018 | Atkin et al. |
| 10,154,957 B2 | 12/2018 | Zhang et al. |
| 10,155,334 B2 | 12/2018 | Rendon |
| 10,183,156 B2 | 1/2019 | Ross et al. |
| 10,188,335 B2 | 1/2019 | Haghgooie et al. |
| D840,020 S | 2/2019 | Howgill |
| 10,201,691 B2 | 2/2019 | Berry et al. |
| 10,232,157 B2 | 3/2019 | Berry et al. |
| 10,232,160 B2 | 3/2019 | Baker et al. |
| 10,248,765 B1 | 4/2019 | Holmes et al. |
| 10,265,484 B2 | 4/2019 | Stuart et al. |
| 10,272,214 B2 | 4/2019 | Child et al. |
| 10,300,260 B2 | 5/2019 | Wirtanen et al. |
| 10,307,578 B2 | 6/2019 | Frederickson et al. |
| 10,315,021 B2 | 6/2019 | Frederickson et al. |
| 10,327,990 B2 | 6/2019 | Egeland et al. |
| 10,328,248 B2 | 6/2019 | Baker et al. |
| 10,335,560 B2 | 7/2019 | Stein et al. |
| 10,335,562 B2 | 7/2019 | Jinks et al. |
| 10,335,563 B2 | 7/2019 | Brewer et al. |
| 10,357,610 B2 | 7/2019 | Sonderegger |
| 10,384,047 B2 | 8/2019 | Simmers |
| 10,391,290 B2 | 8/2019 | Burton et al. |
| 10,398,885 B2 | 9/2019 | Frits et al. |
| 10,406,339 B2 | 9/2019 | Simmers |
| 10,410,838 B2 | 9/2019 | Hanson et al. |
| 10,426,390 B2 | 10/2019 | Berthier et al. |
| 10,426,739 B2 | 10/2019 | Knutson |
| 10,478,346 B2 | 11/2019 | Knutson |
| 10,492,716 B2 | 12/2019 | Berthier et al. |
| 10,507,286 B2 | 12/2019 | Egeland et al. |
| 10,518,071 B2 | 12/2019 | Kulkarni |
| D872,853 S | 1/2020 | Stuart et al. |
| 10,525,463 B2 | 1/2020 | Kelly et al. |
| 10,542,922 B2 | 1/2020 | Sia et al. |
| 10,543,310 B2 | 1/2020 | Bernstein et al. |
| 10,549,079 B2 | 2/2020 | Burton et al. |
| 10,568,937 B2 | 2/2020 | Hattersley et al. |
| D878,544 S | 3/2020 | Stuart et al. |
| 10,576,257 B2 | 3/2020 | Berry et al. |
| 10,596,333 B2 | 3/2020 | Howgill |
| 10,598,583 B1 | 3/2020 | Peeters et al. |
| 10,638,963 B2 | 5/2020 | Beyerlein et al. |
| 10,646,703 B2 | 5/2020 | Chowdhury |
| 10,653,349 B2 | 5/2020 | Delamarche et al. |
| 10,695,289 B2 | 6/2020 | Brown et al. |
| 10,695,547 B2 | 6/2020 | Burton et al. |
| 10,716,926 B2 | 7/2020 | Burton et al. |
| 10,729,842 B2 | 8/2020 | Hooven et al. |
| 10,772,550 B2 | 9/2020 | Aceti et al. |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,881,342 B2 | 1/2021 | Kelly et al. |
| 10,888,259 B2 | 1/2021 | Jordan et al. |
| 10,926,030 B2 | 2/2021 | Lanigan et al. |
| 10,932,710 B2 | 3/2021 | Jordan et al. |
| 10,939,860 B2 | 3/2021 | Levinson et al. |
| 10,940,085 B2 | 3/2021 | Baker et al. |
| 10,953,211 B2 | 3/2021 | Ross et al. |
| 11,020,548 B2 | 6/2021 | Stuart et al. |
| 11,033,212 B2 | 6/2021 | Berthier et al. |
| 11,040,183 B2 | 6/2021 | Baker et al. |
| 11,103,685 B2 | 8/2021 | Gonzalez et al. |
| 11,110,234 B2 | 9/2021 | Richardson et al. |
| 11,116,953 B2 | 9/2021 | Kobayashi et al. |
| 11,147,955 B2 | 10/2021 | Gross et al. |
| 11,177,029 B2 | 11/2021 | Levinson et al. |
| 11,197,625 B1 | 12/2021 | Schleicher et al. |
| 11,202,895 B2 | 12/2021 | Davis et al. |
| 11,207,477 B2 | 12/2021 | Hodson |
| 11,247,033 B2 | 2/2022 | Baker et al. |
| 11,253,179 B2 | 2/2022 | Bernstein et al. |
| 11,266,337 B2 | 3/2022 | Jackson et al. |
| 11,273,272 B2 | 3/2022 | Stuart et al. |
| 11,291,989 B2 | 4/2022 | Morrison |
| 11,298,060 B2 | 4/2022 | Jordan et al. |
| 11,298,478 B2 | 4/2022 | Stuart et al. |
| 11,304,632 B2 | 4/2022 | Mou et al. |
| 11,344,684 B2 | 5/2022 | Richardson et al. |
| 11,395,614 B2 | 7/2022 | Berthier et al. |
| 11,452,474 B1 | 9/2022 | Nawana et al. |
| 11,458,289 B2 | 10/2022 | Moeckly et al. |
| 11,497,712 B2 | 11/2022 | Stein et al. |
| 11,497,866 B2 | 11/2022 | Howgill |
| 11,510,602 B1 | 11/2022 | Nawana et al. |
| 2002/0077584 A1 | 6/2002 | Lin et al. |
| 2002/0193740 A1 | 12/2002 | Alchas et al. |
| 2004/0002121 A1 | 1/2004 | Regan et al. |
| 2004/0010207 A1 | 1/2004 | Flaherty et al. |
| 2004/0059256 A1 | 3/2004 | Perez |
| 2004/0059366 A1 | 3/2004 | Sato et al. |
| 2004/0106904 A1 | 6/2004 | Gonnelli et al. |
| 2004/0162467 A1 | 8/2004 | Cook |
| 2005/0106713 A1 | 5/2005 | Phan et al. |
| 2005/0118388 A1 | 6/2005 | Kingsford |
| 2005/0203461 A1 | 9/2005 | Flaherty et al. |
| 2006/0047243 A1 | 3/2006 | Rosenberg |
| 2006/0068490 A1 | 3/2006 | Tang et al. |
| 2006/0142651 A1 | 6/2006 | Brister et al. |
| 2006/0271084 A1 | 11/2006 | Schraga |
| 2007/0004989 A1 | 1/2007 | Dhillon |
| 2007/0191696 A1 | 8/2007 | Mischler et al. |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0099427 A1 | 4/2009 | Jina et al. |
| 2009/0105614 A1 | 4/2009 | Momose et al. |
| 2009/0112125 A1 | 4/2009 | Tamir |
| 2009/0259176 A1 | 10/2009 | Yairi |
| 2010/0121271 A1 | 5/2010 | Perriere |
| 2010/0198107 A1 | 8/2010 | Groll et al. |
| 2010/0249560 A1 | 9/2010 | Levinson et al. |
| 2010/0256524 A1 | 10/2010 | Levinson et al. |
| 2010/0269837 A1 | 10/2010 | Levinson et al. |
| 2010/0272652 A1 | 10/2010 | Levinson |
| 2011/0009847 A1 | 1/2011 | Levinson et al. |
| 2011/0060280 A1 | 3/2011 | Caffey et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0144463 A1 | 6/2011 | Pesach et al. |

(56) References Cited

U.S. PATENT DOCUMENTS

| | | |
|---|---|---|
| 2011/0172508 A1 | 7/2011 | Chickering, III et al. |
| 2011/0172510 A1 | 7/2011 | Chickering, III et al. |
| 2011/0198221 A1 | 8/2011 | Angelescu |
| 2011/0213335 A1 | 9/2011 | Burton et al. |
| 2011/0245635 A1 | 10/2011 | Fujiwara et al. |
| 2011/0257497 A1 | 10/2011 | Tamada et al. |
| 2011/0288389 A9 | 11/2011 | Levinson et al. |
| 2012/0016308 A1 | 1/2012 | Schott |
| 2012/0041338 A1 | 2/2012 | Chickering, III et al. |
| 2012/0046203 A1 | 2/2012 | Walsh et al. |
| 2012/0078224 A1 | 3/2012 | Lerner et al. |
| 2012/0109066 A1 | 5/2012 | Chase et al. |
| 2012/0123297 A1 | 5/2012 | Brancazio |
| 2012/0259599 A1 | 10/2012 | Deck et al. |
| 2012/0271123 A1 | 10/2012 | Castle et al. |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2013/0018279 A1 | 1/2013 | Plante et al. |
| 2013/0158468 A1 | 6/2013 | Bernstein et al. |
| 2013/0158482 A1 | 6/2013 | Davis et al. |
| 2013/0211289 A1 | 8/2013 | Moga et al. |
| 2013/0253446 A1 | 9/2013 | Duan et al. |
| 2013/0269423 A1 | 10/2013 | Angelescu |
| 2014/0066843 A1 | 3/2014 | Zhang et al. |
| 2014/0109900 A1 | 4/2014 | Jinks |
| 2014/0194854 A1 | 7/2014 | Tsals |
| 2014/0305823 A1 | 10/2014 | Gelfand et al. |
| 2014/0309555 A1 | 10/2014 | Gelfand et al. |
| 2014/0309557 A1 | 10/2014 | Fletcher et al. |
| 2014/0336616 A1 | 11/2014 | Edwards |
| 2015/0057510 A1 | 2/2015 | Levinson et al. |
| 2015/0057901 A1 | 2/2015 | Sundholm et al. |
| 2015/0073385 A1 | 3/2015 | Lyon et al. |
| 2015/0087944 A1 | 3/2015 | Levinson et al. |
| 2015/0136122 A1 | 5/2015 | Stuart et al. |
| 2015/0250959 A1 | 9/2015 | Stuart et al. |
| 2015/0258272 A1 | 9/2015 | Sullivan et al. |
| 2015/0278476 A1 | 10/2015 | Levinson et al. |
| 2015/0352295 A1 | 12/2015 | Burton et al. |
| 2016/0038068 A1 | 2/2016 | Chickering, III et al. |
| 2016/0051981 A1 | 2/2016 | Berthier et al. |
| 2016/0067468 A1 | 3/2016 | Chowdhury |
| 2016/0136365 A1 | 5/2016 | Stuart et al. |
| 2016/0144100 A1 | 5/2016 | Gharib et al. |
| 2016/0199581 A1 | 7/2016 | Cachemaille et al. |
| 2016/0213295 A1 | 7/2016 | Matsunami et al. |
| 2016/0256095 A1 | 9/2016 | Krasnow et al. |
| 2016/0262676 A1 | 9/2016 | Haghgooie et al. |
| 2016/0315123 A1 | 10/2016 | Kim et al. |
| 2016/0324506 A1 | 11/2016 | Tariyal et al. |
| 2016/0354589 A1 | 12/2016 | Kobayashi et al. |
| 2016/0361006 A1 | 12/2016 | Bullington et al. |
| 2017/0001192 A1 | 1/2017 | Kelly et al. |
| 2017/0014822 A1 | 1/2017 | Ker |
| 2017/0021067 A1 | 1/2017 | Todd et al. |
| 2017/0021117 A1 | 1/2017 | Howgill |
| 2017/0035337 A1 | 2/2017 | Wilkinson et al. |
| 2017/0035975 A1 | 2/2017 | Myung et al. |
| 2017/0043103 A1 | 2/2017 | Wotton et al. |
| 2017/0059304 A1 | 3/2017 | Ma et al. |
| 2017/0120022 A1 | 5/2017 | Chickering, III et al. |
| 2017/0122846 A1 | 5/2017 | Holmes et al. |
| 2017/0127991 A1 | 5/2017 | Bernstein et al. |
| 2017/0173288 A1 | 6/2017 | Stam et al. |
| 2017/0197029 A1 | 7/2017 | Cindrich et al. |
| 2017/0224912 A1 | 8/2017 | Yodfat et al. |
| 2017/0231543 A1 | 8/2017 | Cunningham et al. |
| 2017/0290977 A1 | 10/2017 | Schauderna |
| 2018/0001029 A1 | 1/2018 | Egeland et al. |
| 2018/0008183 A1 | 1/2018 | Chickering, III et al. |
| 2018/0008703 A1 | 1/2018 | Johnson |
| 2018/0008808 A1 | 1/2018 | Chowdhury |
| 2018/0021559 A1 | 1/2018 | Xu |
| 2018/0078241 A1 | 3/2018 | Moga et al. |
| 2018/0103884 A1 | 4/2018 | Delamarche et al. |
| 2018/0126058 A1 | 5/2018 | David et al. |
| 2018/0132515 A1 | 5/2018 | Lawrence et al. |
| 2018/0132774 A1 | 5/2018 | Gonzalez-Zugasti et al. |
| 2018/0242890 A1 | 8/2018 | Chickering, III et al. |
| 2018/0243543 A1 | 8/2018 | Baek et al. |
| 2018/0296148 A1 | 10/2018 | Gelfand et al. |
| 2018/0304063 A1 | 10/2018 | Gonzalez et al. |
| 2018/0344631 A1 | 12/2018 | Zhang et al. |
| 2018/0369512 A1 | 12/2018 | Blatchford et al. |
| 2019/0000365 A1* | 1/2019 | Beyerlein ........ A61B 5/150984 |
| 2019/0001076 A1 | 1/2019 | Solomon et al. |
| 2019/0001081 A1 | 1/2019 | Guion et al. |
| 2019/0001085 A1 | 1/2019 | Cottenden et al. |
| 2019/0005401 A1 | 1/2019 | Frostell-Karlsson et al. |
| 2019/0015584 A1 | 1/2019 | Meehan et al. |
| 2019/0015827 A1 | 1/2019 | Berthier et al. |
| 2019/0022339 A1 | 1/2019 | Richardson et al. |
| 2019/0023473 A1 | 1/2019 | Schott |
| 2019/0030260 A1 | 1/2019 | Wotton et al. |
| 2019/0053740 A1 | 2/2019 | Bernstein et al. |
| 2019/0054010 A1 | 2/2019 | Slowey et al. |
| 2019/0142318 A1 | 5/2019 | Diebold et al. |
| 2019/0159709 A1 | 5/2019 | Barone et al. |
| 2019/0209820 A1 | 7/2019 | Chickering, III et al. |
| 2019/0240470 A1 | 8/2019 | Frederickson et al. |
| 2019/0298943 A1 | 10/2019 | Stuart et al. |
| 2019/0336058 A1 | 11/2019 | Haghgooie et al. |
| 2019/0366067 A1 | 12/2019 | Ginggen et al. |
| 2020/0009364 A1 | 1/2020 | Amir |
| 2020/0010219 A1 | 1/2020 | Felippone et al. |
| 2020/0011860 A1 | 1/2020 | Nawana et al. |
| 2020/0033008 A1 | 1/2020 | Baker |
| 2020/0069897 A1 | 3/2020 | Hodson et al. |
| 2020/0085414 A1 | 3/2020 | Berthier et al. |
| 2020/0101219 A1 | 4/2020 | Wang et al. |
| 2020/0147209 A1 | 5/2020 | Johnson |
| 2020/0163603 A1 | 5/2020 | Jordan et al. |
| 2020/0164359 A1 | 5/2020 | Jordan et al. |
| 2020/0246560 A1 | 8/2020 | Hodson et al. |
| 2020/0253521 A1 | 8/2020 | Ivosevic et al. |
| 2020/0261668 A1 | 8/2020 | Hodson et al. |
| 2020/0289808 A1 | 9/2020 | Moeckly et al. |
| 2020/0297945 A1 | 9/2020 | Cottenden et al. |
| 2020/0353155 A1 | 11/2020 | Bernstein et al. |
| 2021/0022681 A1 | 1/2021 | Chickering, III et al. |
| 2021/0030975 A1 | 2/2021 | Burton et al. |
| 2021/0059588 A1 | 3/2021 | Welch et al. |
| 2021/0100487 A1 | 4/2021 | Cho et al. |
| 2021/0121110 A1 | 4/2021 | Kelly et al. |
| 2021/0170153 A1 | 6/2021 | Ross et al. |
| 2021/0196567 A1 | 7/2021 | Baker et al. |
| 2021/0228124 A1 | 7/2021 | Gonzalez-Zugasti et al. |
| 2021/0259599 A1 | 8/2021 | Haghgooie et al. |
| 2021/0298679 A1 | 9/2021 | Pierart |
| 2021/0330227 A1 | 10/2021 | Levinson et al. |
| 2021/0369150 A1 | 12/2021 | Bernstein et al. |
| 2021/0378567 A1 | 12/2021 | Weidemaier et al. |
| 2022/0031211 A1 | 2/2022 | Yakhnich et al. |
| 2022/0058895 A1 | 2/2022 | Han |
| 2022/0062607 A1 | 3/2022 | Davis et al. |
| 2022/0071534 A9 | 3/2022 | Gonzalez-Zugasti et al. |
| 2022/0133192 A1 | 5/2022 | Brancazio |
| 2022/0134072 A1 | 5/2022 | Kosel et al. |
| 2022/0215921 A1 | 7/2022 | Levinson et al. |
| 2022/0218251 A1 | 7/2022 | Jackson et al. |
| 2022/0233117 A1 | 7/2022 | Lee et al. |
| 2022/0249818 A1 | 8/2022 | Chickering, III et al. |
| 2022/0257158 A1 | 8/2022 | Haghgooie et al. |
| 2022/0287642 A1 | 9/2022 | Chickering, III et al. |
| 2022/0313128 A1 | 10/2022 | Bernstein et al. |
| 2022/0330860 A1 | 10/2022 | Nawana |
| 2022/0330861 A1 | 10/2022 | Nawana |
| 2022/0347451 A1 | 11/2022 | Jung et al. |
| 2022/0361784 A1 | 11/2022 | Jordan et al. |

(56) References Cited

U.S. PATENT DOCUMENTS

| | | |
|---|---|---|
| 2022/0369957 A1 | 11/2022 | Nawana |
| 2023/0109881 A1 | 4/2023 | Nawana et al. |

FOREIGN PATENT DOCUMENTS

| | | |
|---|---|---|
| AU | 2016266112 A1 | 12/2016 |
| CN | 101296752 A | 10/2008 |
| EP | 0931507 A1 | 7/1999 |
| EP | 1769735 A1 | 4/2007 |
| EP | 2493537 A2 | 9/2012 |
| EP | 2493537 B1 | 12/2017 |
| EP | 3513833 A1 | 7/2019 |
| EP | 3490453 B1 | 12/2021 |
| EP | 3962363 A1 | 3/2022 |
| ES | 2550668 T3 | 11/2015 |
| ES | 2565805 T3 | 4/2016 |
| GB | 1492500 A | 11/1977 |
| GB | 2428197 A | 1/2007 |
| JP | 2004024164 A | 1/2004 |
| JP | 2018538535 A | 12/2018 |
| KR | 100873642 B1 | 12/2008 |
| KR | 101857300 | 5/2018 |
| KR | 101857300 B1 | 5/2018 |
| NO | 2012028675 A3 | 5/2012 |
| WO | 9311747 A1 | 6/1993 |
| WO | 9929296 A1 | 6/1999 |
| WO | 0078286 A1 | 12/2000 |
| WO | 0210037 A1 | 2/2002 |
| WO | 0226217 A2 | 4/2002 |
| WO | 0232785 A1 | 4/2002 |
| WO | 02083205 A1 | 10/2002 |
| WO | 02083231 A1 | 10/2002 |
| WO | 02083232 A1 | 10/2002 |
| WO | 03002069 A2 | 1/2003 |
| WO | 03030880 A1 | 4/2003 |
| WO | 03035510 A1 | 5/2003 |
| WO | 03066126 A2 | 8/2003 |
| WO | 03084597 A1 | 10/2003 |
| WO | 03086349 A1 | 10/2003 |
| WO | 03086350 A1 | 10/2003 |
| WO | 03089036 A1 | 10/2003 |
| WO | 2004009172 A1 | 1/2004 |
| WO | 2004022133 A2 | 3/2004 |
| WO | 2004022142 A1 | 3/2004 |
| WO | 2004032990 A2 | 4/2004 |
| WO | 2004039429 A2 | 5/2004 |
| WO | 2004062715 A3 | 10/2004 |
| WO | 2004098576 A1 | 11/2004 |
| WO | 2005006535 A1 | 1/2005 |
| WO | 2005026236 A1 | 3/2005 |
| WO | 2005060441 A2 | 7/2005 |
| WO | 2005014078 A3 | 10/2005 |
| WO | 2005084534 | 10/2005 |
| WO | 2005084534 A1 | 10/2005 |
| WO | 2005123173 A1 | 12/2005 |
| WO | 2006016364 A2 | 2/2006 |
| WO | 2006055795 A1 | 5/2006 |
| WO | 2006055799 A1 | 5/2006 |
| WO | 2006055802 A1 | 5/2006 |
| WO | 2006055844 A2 | 5/2006 |
| WO | 2006062848 A1 | 6/2006 |
| WO | 2006062974 A2 | 6/2006 |
| WO | 2006108185 A1 | 10/2006 |
| WO | 2006115663 A2 | 11/2006 |
| WO | 2006135696 A2 | 12/2006 |
| WO | 2007002521 A2 | 1/2007 |
| WO | 2007002522 A1 | 1/2007 |
| WO | 2007002523 A2 | 1/2007 |
| WO | 2007023276 A1 | 3/2007 |
| WO | 2007061781 A1 | 5/2007 |
| WO | 2007064486 A1 | 6/2007 |
| WO | 2007103712 A2 | 9/2007 |
| WO | 2006110723 A3 | 11/2007 |
| WO | 2007124411 A1 | 11/2007 |
| WO | 2008014161 A1 | 1/2008 |
| WO | 2007124406 A3 | 2/2008 |
| WO | 2008008845 A3 | 4/2008 |
| WO | 2008049107 A1 | 4/2008 |
| WO | 2008091602 A3 | 9/2008 |
| WO | 2008121459 A1 | 10/2008 |
| WO | 2008149333 A1 | 12/2008 |
| WO | 2008149333 A9 | 1/2009 |
| WO | 2009037192 A1 | 3/2009 |
| WO | 2009046173 A3 | 5/2009 |
| WO | 2009061895 A2 | 5/2009 |
| WO | 2009061907 A2 | 5/2009 |
| WO | 2009056981 A3 | 8/2009 |
| WO | 2009126653 A1 | 10/2009 |
| WO | 2009158300 A1 | 12/2009 |
| WO | 2009142852 A3 | 1/2010 |
| WO | 2010049048 A1 | 5/2010 |
| WO | 2010059605 A2 | 5/2010 |
| WO | 2010062908 A1 | 6/2010 |
| WO | 2010071262 A1 | 6/2010 |
| WO | 2010098339 A1 | 9/2010 |
| WO | 2010101621 A1 | 9/2010 |
| WO | 2010101625 A2 | 9/2010 |
| WO | 2010101626 A1 | 9/2010 |
| WO | 2010101620 A3 | 11/2010 |
| WO | 2010129783 A1 | 11/2010 |
| WO | 2010002613 A3 | 12/2010 |
| WO | 2010110916 A3 | 12/2010 |
| WO | 2010151329 A1 | 12/2010 |
| WO | 2011014514 A1 | 2/2011 |
| WO | 2010117602 A3 | 3/2011 |
| WO | 2011016615 A3 | 4/2011 |
| WO | 2011053787 A2 | 5/2011 |
| WO | 2011053788 A2 | 5/2011 |
| WO | 2011053796 A2 | 5/2011 |
| WO | 2011063067 A1 | 5/2011 |
| WO | 2011065972 A2 | 6/2011 |
| WO | 2011071788 A1 | 6/2011 |
| WO | 2011075099 A1 | 6/2011 |
| WO | 2011075103 A1 | 6/2011 |
| WO | 2011075104 A1 | 6/2011 |
| WO | 2011075105 A1 | 6/2011 |
| WO | 2011075569 A1 | 6/2011 |
| WO | 2011084316 A2 | 7/2011 |
| WO | 2011088211 A2 | 7/2011 |
| WO | 2011094573 A1 | 8/2011 |
| WO | 2011014514 | 9/2011 |
| WO | 2011088214 A3 | 9/2011 |
| WO | 2011113114 A1 | 9/2011 |
| WO | 2011116388 A1 | 9/2011 |
| WO | 2011084951 A3 | 11/2011 |
| WO | 2011088211 A3 | 12/2011 |
| WO | 2011150144 A2 | 12/2011 |
| WO | 2011163347 A2 | 12/2011 |
| WO | 2012030316 A1 | 3/2012 |
| WO | 2012018486 A3 | 4/2012 |
| WO | 2012045561 A1 | 4/2012 |
| WO | 2012048388 A1 | 4/2012 |
| WO | 2012049155 A1 | 4/2012 |
| WO | 2012054592 A1 | 4/2012 |
| WO | 2012021792 A3 | 5/2012 |
| WO | 2012028675 A3 | 5/2012 |
| WO | 2012061556 A1 | 5/2012 |
| WO | 2012089627 A1 | 7/2012 |
| WO | 2012122162 A1 | 9/2012 |
| WO | 2012145665 A2 | 10/2012 |
| WO | 2012117302 A3 | 11/2012 |
| WO | 2012149126 A1 | 11/2012 |
| WO | 2012149134 A1 | 11/2012 |
| WO | 2012149143 A1 | 11/2012 |
| WO | 2012154362 A1 | 11/2012 |
| WO | 2012154362 | 12/2012 |
| WO | 2012173971 A2 | 12/2012 |
| WO | 2012149134 | 1/2013 |
| WO | 2012149155 A9 | 3/2013 |
| WO | 2013036602 A1 | 3/2013 |
| WO | 2013050701 A1 | 4/2013 |
| WO | 2013055638 A1 | 4/2013 |
| WO | 2013055641 A1 | 4/2013 |
| WO | 2013059409 A1 | 4/2013 |

(56) References Cited

FOREIGN PATENT DOCUMENTS

| | | |
|---|---|---|
| WO | 2013082418 A1 | 6/2013 |
| WO | 2013082427 A1 | 6/2013 |
| WO | 2013090353 A1 | 6/2013 |
| WO | 2013096026 A1 | 6/2013 |
| WO | 2013096027 A1 | 6/2013 |
| WO | 2013112877 A1 | 8/2013 |
| WO | 2013120665 A1 | 8/2013 |
| WO | 2013136176 A1 | 9/2013 |
| WO | 2013136185 A3 | 11/2013 |
| WO | 2013165715 A1 | 11/2013 |
| WO | 2013188609 A1 | 12/2013 |
| WO | 2014004462 A1 | 1/2014 |
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |
| WO | 2014078545 A1 | 5/2014 |
| WO | 2014081746 A1 | 5/2014 |
| WO | 2014099404 A1 | 6/2014 |
| WO | 2014105458 A1 | 7/2014 |
| WO | 2014110016 A1 | 7/2014 |
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014172246 A1 | 10/2014 |
| WO | 2014172247 A1 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015168219 A1 | 11/2015 |
| WO | 2015179511 A1 | 11/2015 |
| WO | 2016009986 A1 | 1/2016 |
| WO | 2016018892 A1 | 2/2016 |
| WO | 2016081843 A1 | 5/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017024115 A1 | 2/2017 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

International Preliminary Report of Patentability, PCT/US2022/029829, dated Nov. 21, 2023.
International Preliminary Report on Patentability, PCT/US2022/024607 dated Oct. 12, 2023.
Written Opinion for International Application, No. PCT/US2022/024607, dated Oct. 12, 2023.
International Search Report and Written Opinion, PCT/US2022/024607, dated Aug. 4, 2022.
Taiwan Office Action, TW111142334, dated Dec. 12, 2023.
Taiwan Office Action, TW111142334, dated May 18, 2023.
U.S. Appl. No. 17/719,881, filed Apr. 13, 2022, Self-Contained Dermal Patch for Detection of Physiological Analytes.
U.S. Appl. No. 17/412,205, filed Aug. 25, 2021, Dermal Patch System.
U.S. Appl. No. 17/747,544, filed May 18, 2022, Self-Contained Dermal Patch for Blood Analysis.
U.S. Appl. No. 17/412,213, filed Aug. 25, 2021, Dual Lever Dermal Patch System.
U.S. Appl. No. 17/903,802, filed Sep. 6, 2022, Dual Lever Dermal Patch System.
U.S. Appl. No. 17/500,873, filed Oct. 13, 2021, Mono Dose Dermal Patch for Pharmaceutical Delivery.
U.S. Appl. No. 17/521,466, filed Nov. 8, 2021, Dermal Patch for Collecting a Physiological Sample.
U.S. Appl. No. 17/994,454, filed Nov. 28, 2022, Dermal Patch for Collecting a Physiological Sample.
U.S. Appl. No. 18/090,026, filed Dec. 28, 2022, Dermal Patch for Collecting a Physiological Sample.
U.S. Appl. No. 17/971,142, filed Oct. 21, 2022, Dermal Patch for Collecting a Physiological Sample.
U.S. Appl. No. 17/991,284, filed Nov. 21, 2022, Dermal Patch for Collecting a Physiological Sample with Removable Vial.
U.S. Appl. No. 18/090,063, filed Dec. 28, 2022, Dermal Patch with a Diagnostic Test Strip.
U.S. Appl. No. 18/090,107, filed Dec. 28, 2022, Dermal Patch for Delivering a Pharmaceutical.
International Preliminary Report of Patentability for PCT/US2022/046384 issued Apr. 16, 2024.
International Preliminary Report of Patentability for PCT/US2022/048913 dated May 2, 2024.

(56) References Cited

OTHER PUBLICATIONS

International Search Report and Written Opinion for PCT/US2022/046384 mailed Jan. 5, 2023.
International Search Report and Written Opinion for International Application No. PCT/US2023/080656 dated Feb. 19, 2024.
International Search Report and Written Opinion for International Application No. PCT/US2023/086234 dated Mar. 7, 2024.
International Search Report and Written Opinion for PCT/US2022/048913 mailed Feb. 21, 2023.
International Search Report and Written Opinion for PCT/US2023/086151 dated May 13, 2024.
International Search Report and Written Opinion for PCT/US22/029829 mailed Nov. 23, 2022.
International Search Report and Written Opinion, PCT/US2022/046384, dated Jan. 5, 2023, 12 pages.
International Search Report and Written Opinion, PCT/US2022/048913, dated Feb. 21, 2023, 16 pages.
International Search Report for International Application No. PCT/2023/086214 dated Apr. 8, 2024.
U.S. Appl. No. 18/597,513, filed Mar. 6, 2024, Lancet for Use with a Dermal Patch System.
U.S. Appl. No. 18/674,275, filed May 24, 2024, Dermal Patch for Collecting a Physiological Sample.
U.S. Appl. No. 18/596,098, Dermal Patch with Biomeuic Sensor.
Copies of the foreign references and the NPLs are not submitted herewith as they can be retrieved in the U.S. Appl. No. 17/903,802, filed Sep. 6, 2022, U.S. Appl. No. 17/500,873, filed Oct. 13, 2021, U.S. Appl. No. 17/994,454, filed Nov. 28, 2022, U.S. Appl. No. 17/971,142, filed Oct. 21, 2022, and U.S. Appl. No. 17/991,284, filed Nov. 21, 2022.

\* cited by examiner

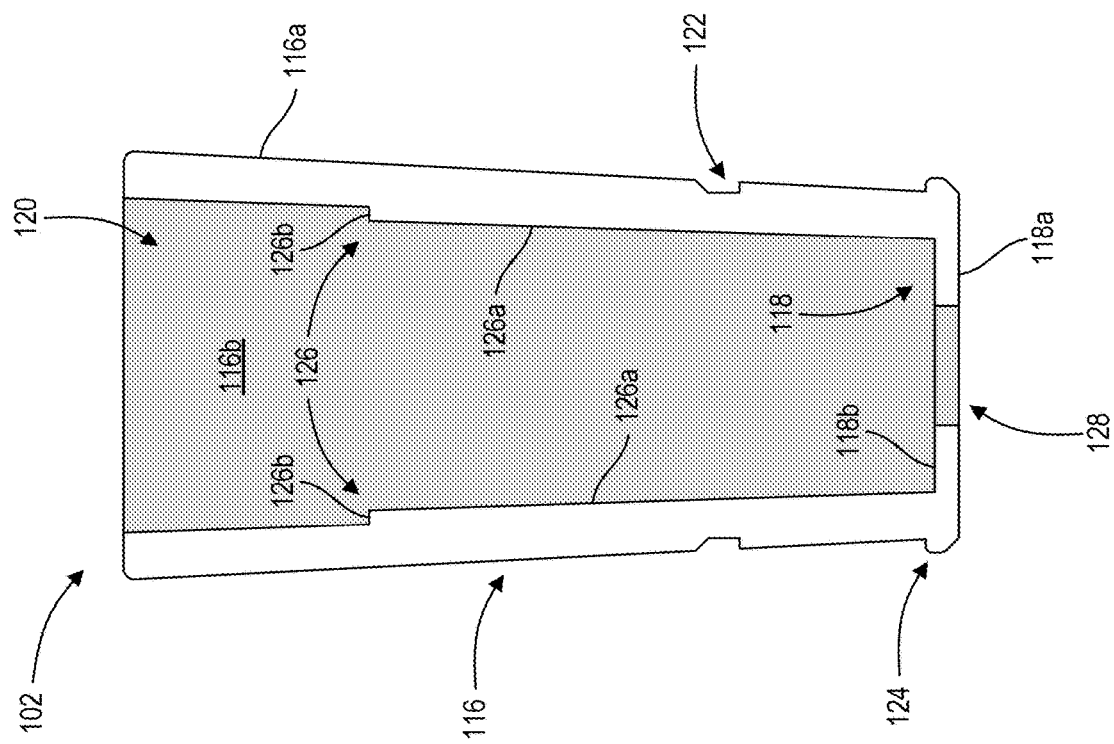
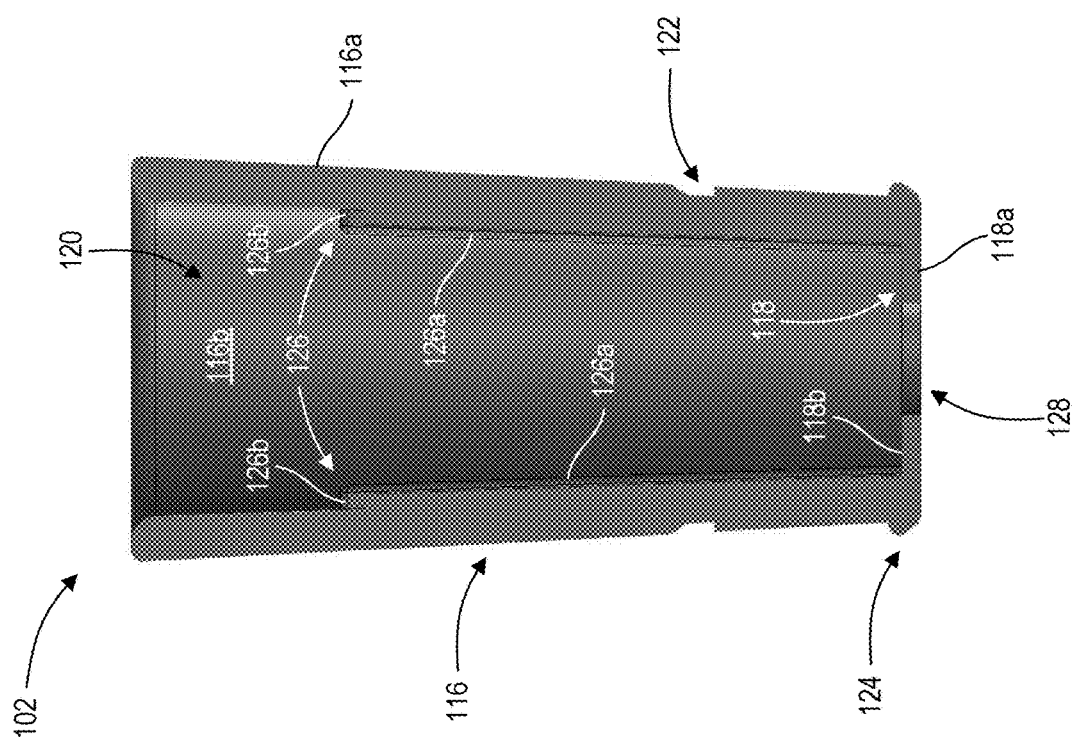
Fig. 11B
Fig. 11A

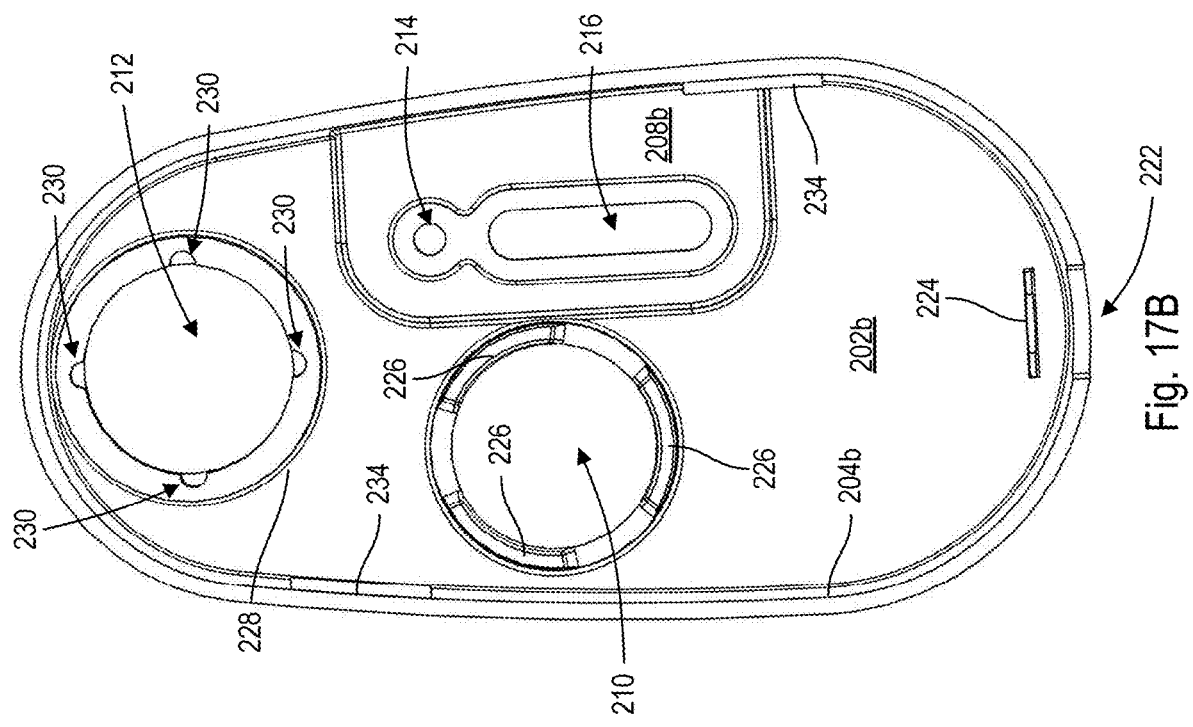
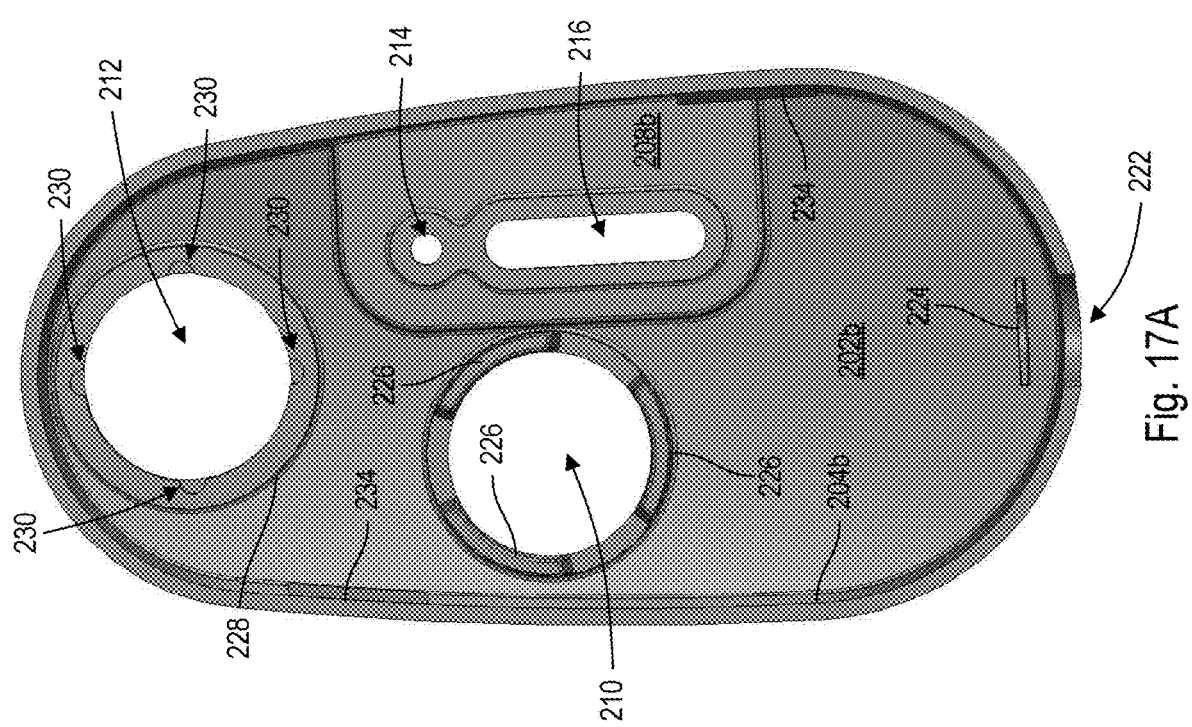
Fig. 17B
Fig. 17A

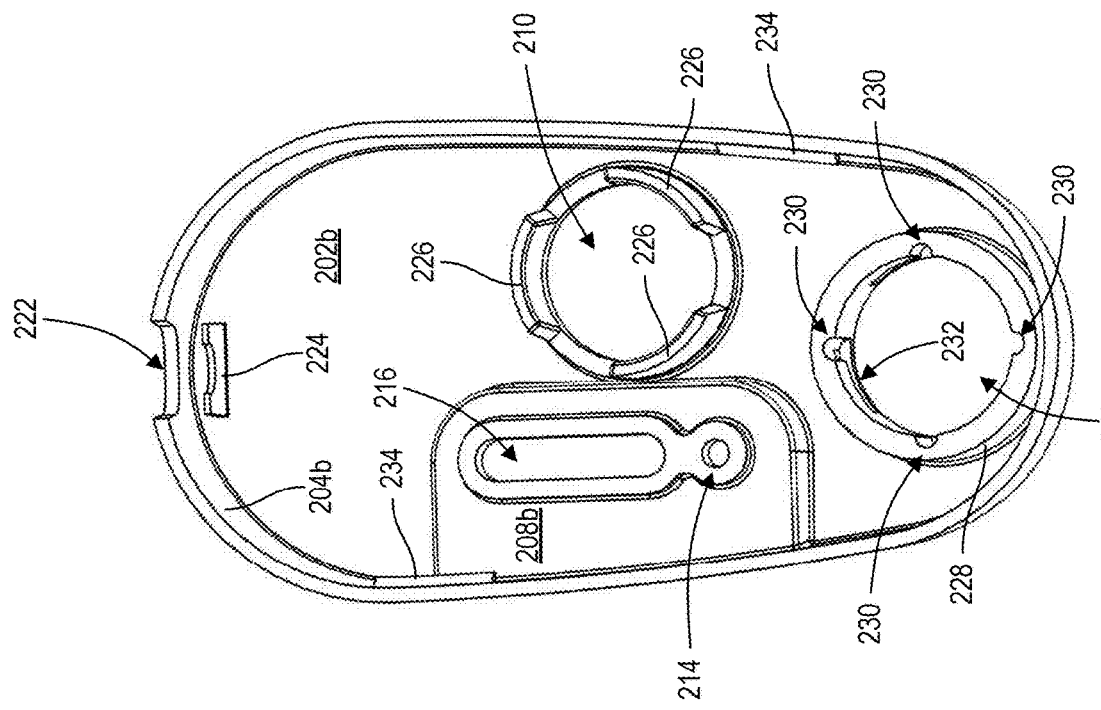
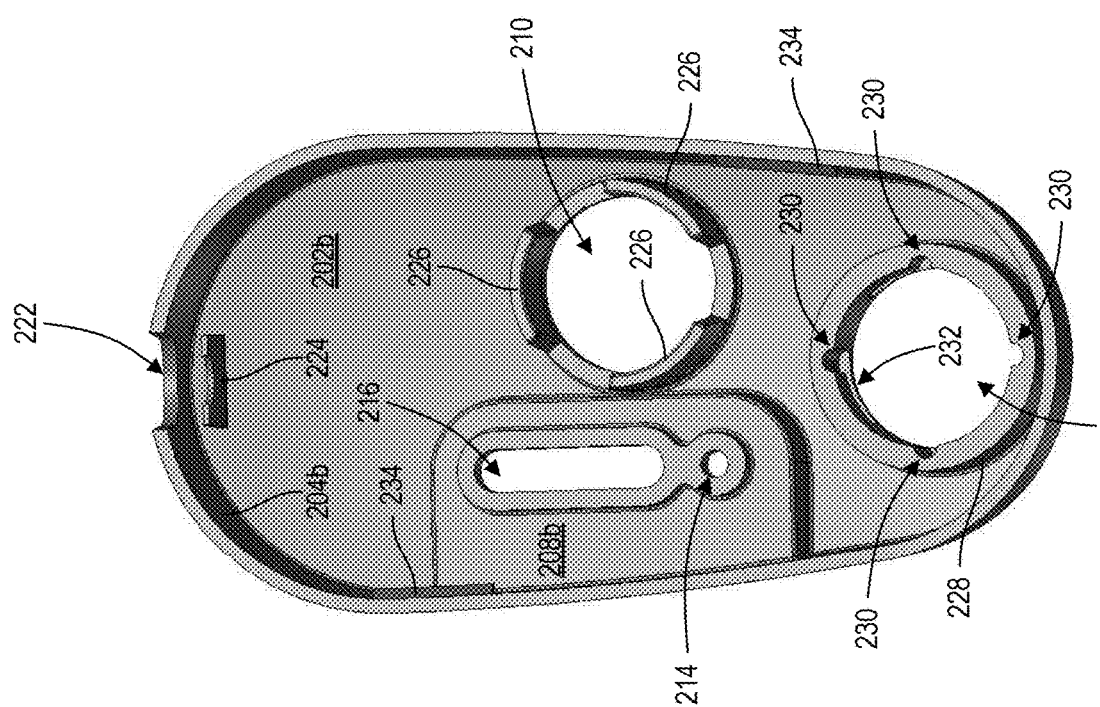

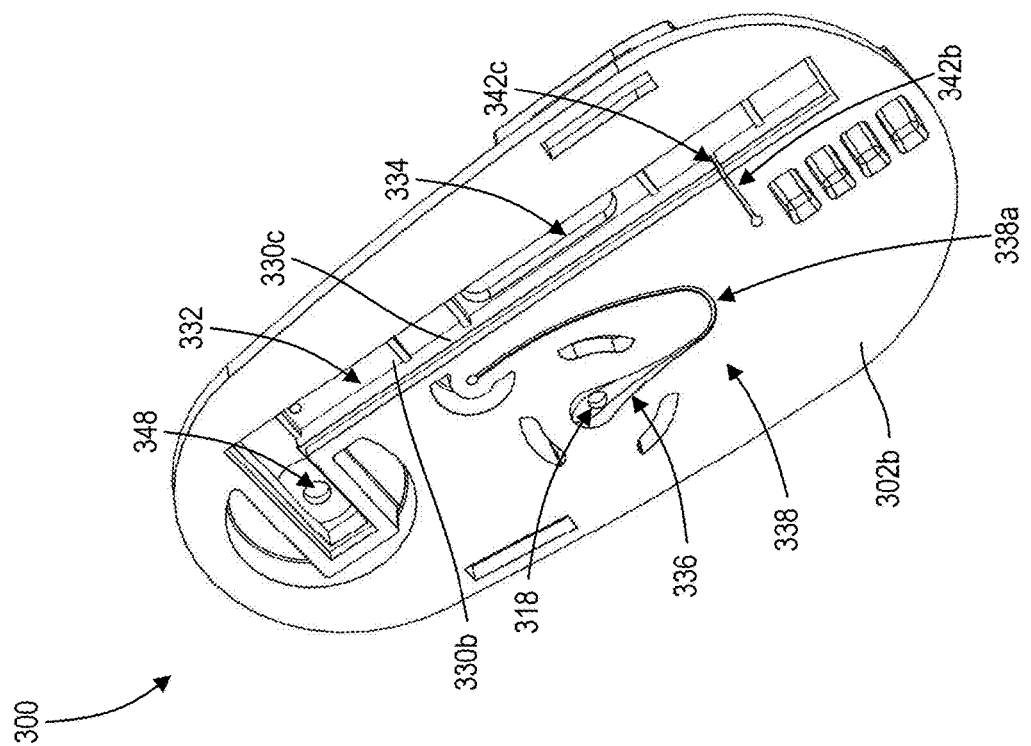
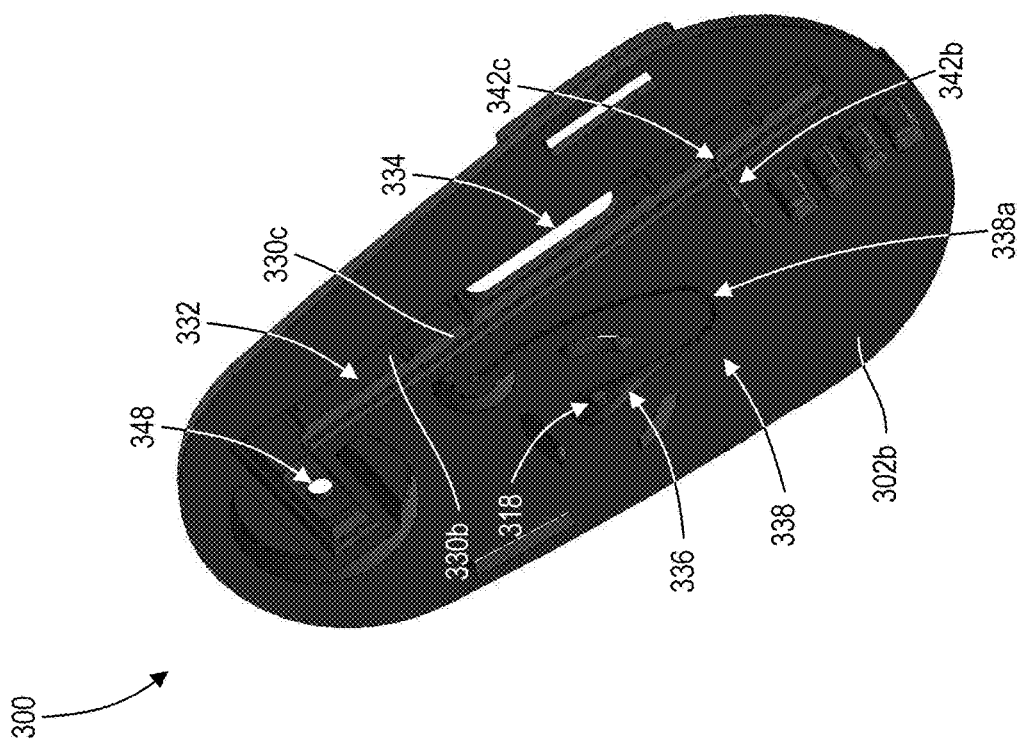

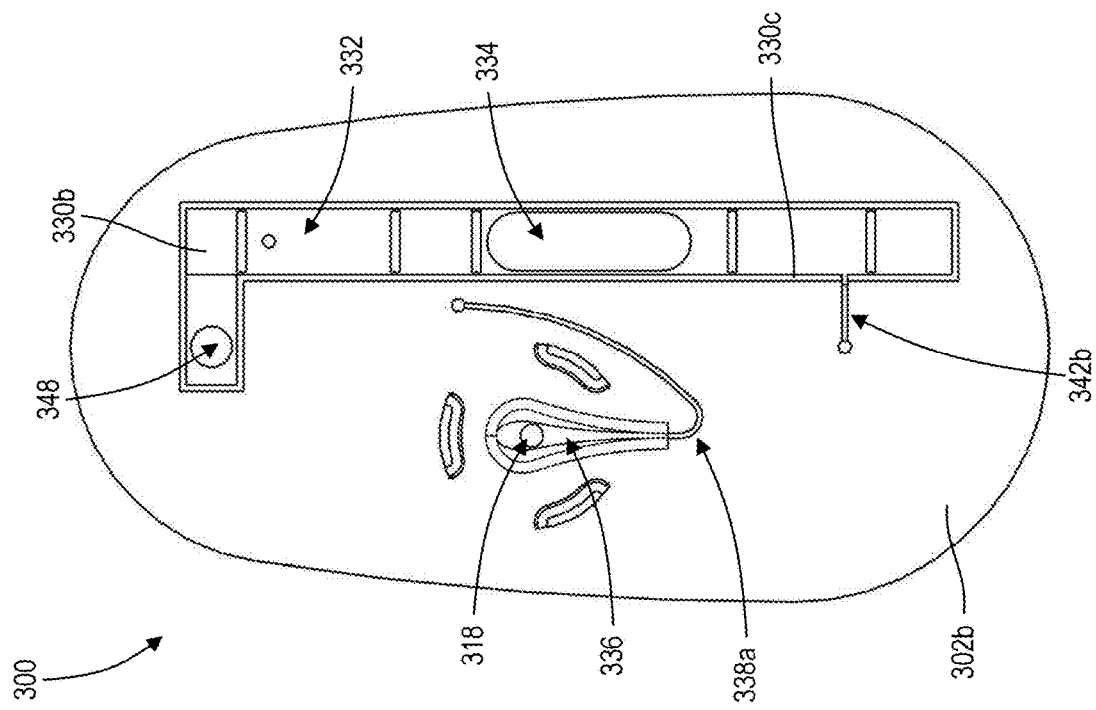
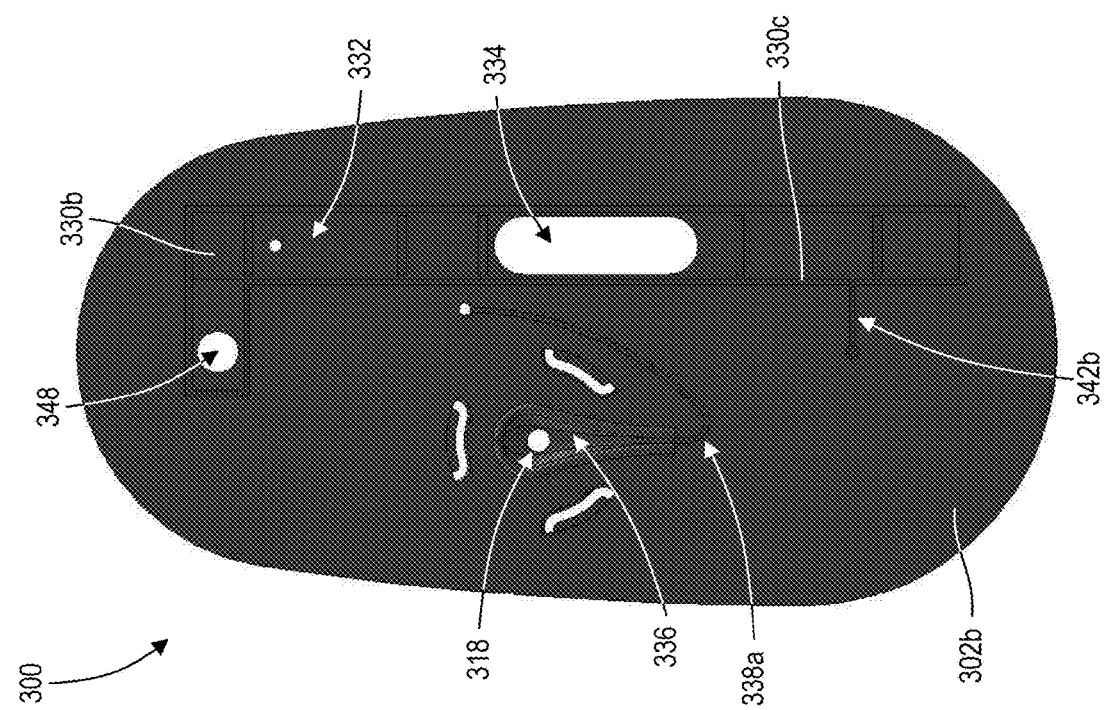

DERMAL PATCH WITH A DIAGNOSTIC TEST STRIP

RELATED APPLICATIONS

The present application is a continuation-in-part of U.S. patent application Ser. No. 17/903,802 (entitled Dual Lever Dermal Patch System and filed on Sep. 6, 2022), Ser. No. 17/500,873 (entitled Mono Dose Dermal Patch for Pharmaceutical Delivery and filed on Oct. 13, 2021), Ser. No. 17/994,454 (entitled Dermal Patch for Collecting a Physiological Sample and filed on Nov. 28, 2022), Ser. No. 17/971,142 (entitled Dermal Patch for Collecting a Physiological Sample and filed on Oct. 21, 2022), and Ser. No. 17/991,284 (entitled Dermal Patch for Collecting a Physiological Sample with Removable Vial and filed on Nov. 21, 2022). Each of these applications is herein incorporated by reference in its entirety.

TECHNICAL FIELD

The present teachings are generally directed to dermal patches that can be employed to detect a biomarker in a drawn physiological sample.

BACKGROUND

Biomarkers are increasingly employed for diagnosis of various disease conditions as well as for assessing treatment protocols. In many cases, it is important to monitor the level of the biomarker over time (e.g., to assess the progression of a disease). The temporal monitoring of biomarkers via conventional techniques includes drawing a physiological fluid sample from a subject. These techniques may be cumbersome and painful to the subject. For example, the invasive nature of drawing a blood sample form a subject can cause discomfort and may lead to less cooperation from a subject, especially children, rendering multiple measurements of a target analyte (e.g., a biomarker) difficult.

Conventional devices allow for continuous monitoring of a target analyte (e.g., glucose monitors) typically suffer from several shortcomings, such as low sensitivity and/or specificity. Therefore, there is still a need for dermal patches for the detection a target analyte.

SUMMARY

Aspects of the present disclosure address the above-referenced problems and/or others.

In one aspect, a system for analyzing a physiological sample includes a cartridge configured to attach to the skin of a subject. The cartridge includes a processing fluid pack that is configured to release a processing fluid stored therein, a diagnostic test strip, and a vacuum pin. The system further includes a lancet with a needle, wherein the lancet is configured to deploy the needle upon engagement with the cartridge to draw a physiological sample from the subject. The vacuum pin is configured to create a vacuum within the cartridge to draw the released processing fluid and the drawn physiological sample to the diagnostic test strip. In some embodiments, the drawn physiological sample and the released processing fluid interact to form a processed physiological sample and the diagnostic test strip is configured to detect a biomarker within the processed physiological sample. In other embodiments, the vacuum pin is moveable between an undeployed position and a deployed position at which the vacuum pin creates the vacuum within the dermal patch when in the deployed position. In some embodiments, the strength of the vacuum generated via movement of the pin is related, e.g., it is proportional on, a distance travelled by the vacuum pin.

In some embodiments, the cartridge further includes a vacuum chamber, wherein the vacuum pin is moveable between the undeployed position and the deployed position within the vacuum chamber. In other embodiments, the cartridge further includes a physiological sample channel in open communication with the vacuum chamber, wherein the physiological sample channel is configured to carry the drawn physiological sample, and wherein the vacuum draws the physiological sample to the diagnostic test strip via the physiological sample channel. In other embodiments, the cartridge further includes a moveable button that is configured to compress the processing fluid pack. In some embodiments, the button is configured to move from a locked position to a deployed position, and the cartridge is configured to prevent the button from compressing the processing fluid pack when the button is in the locked position and is configured to allow the button to compress the processing fluid pack when the button is in the deployed position. In other embodiments, the cartridge further includes a piercing element, and the button is configured to compress the processing fluid pack into the piercing element to rupture the processing fluid pack, thereby releasing a processing fluid contained in the fluid pack.

In certain embodiments, the lancet is configured to automatically deploy the needle upon engagement with the cartridge. In other embodiments, the lancet is configured to automatically retract the needle into a housing of the lancet after deployment. In certain embodiments, the system further comprises a computer system configured to image the diagnostic test strip and determine a result of a test associated with the diagnostic test strip based on the image. In other embodiments, the system also includes an electronic medical record database that stores a plurality of electronic medical records, the cartridge further includes a quick response code, and the computer system is configured to associate the quick response code with an electronic medical record within the electronic medical record database. In other embodiments, the computer system is configured to update the associated electronic medical record with the determined result. In certain embodiments, the processing fluid stored in the processing fluid pack includes a lysing agent. In other embodiments the processing fluid stored in the processing fluid pack includes other reagents (e.g., detergents, surfactants, etc.). In other embodiments, the processing fluid pack includes a buffer, including without limitation, TBS-T, Tris Buffered Saline-Tween, and TENT, and Tris Buffered saline with EDTA. In other embodiments, the processing fluid can be a buffer solution to neutralize pH. In other embodiments, the diagnostic test strip is a lateral flow test strip.

In another aspect, a method for analyzing a physiological sample, affixing a cartridge to the skin of a subject, inserting a lancet with a needle into the cartridge, wherein inserting the lancet into the cartridge deploys the needle to draw a physiological sample from the subject, moving a vacuum pin to create a vacuum within the cartridge which draws the drawn physiological sample to the diagnostic test strip, and rupturing a processing fluid pack of the cartridge to release a processing fluid to the diagnostic test strip. In certain embodiments, the method further includes moving a button of the cartridge to a deployed position to compress the processing fluid pack into a piercing element of the cartridge thereby rupturing the processing fluid pack. In other embodiments, inserting the lancet into the cartridge causes the lancet to automatically deploy the needle.

In yet another aspect, a cartridge configured to attach to skin of a subject includes a processing fluid pack that is configured to release a processing fluid stored therein, a diagnostic test strip, a vacuum pin, and a lancet with a needle. The lancet is configured to deploy the needle upon engagement with the cartridge to draw a physiological sample from the subject. The vacuum pin is configured to create a vacuum within the cartridge to draw the released processing fluid and the drawn physiological sample to the diagnostic test strip.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which:

FIGS. 2A and 2B-7A and 7B depict a cartridge of the dermal patch system in accordance with an exemplary embodiment of the present disclosure;

FIGS. 11A and 11B depict a housing of the lancet in accordance with an exemplary embodiment of the present disclosure;

FIGS. 15A and 15B-22A and 22B depict a cover of the cartridge of the dermal patch system in accordance with an exemplary embodiment of the present disclosure;

FIGS. 23A and 23B-40A and 40B depict a base of the dermal patch system in accordance with an exemplary embodiment of the present disclosure;

FIGS. 43A and 43B-45 depict a button of the dermal patch system in accordance with an exemplary embodiment of the present disclosure;

DETAILED DESCRIPTION

Figure 1A:
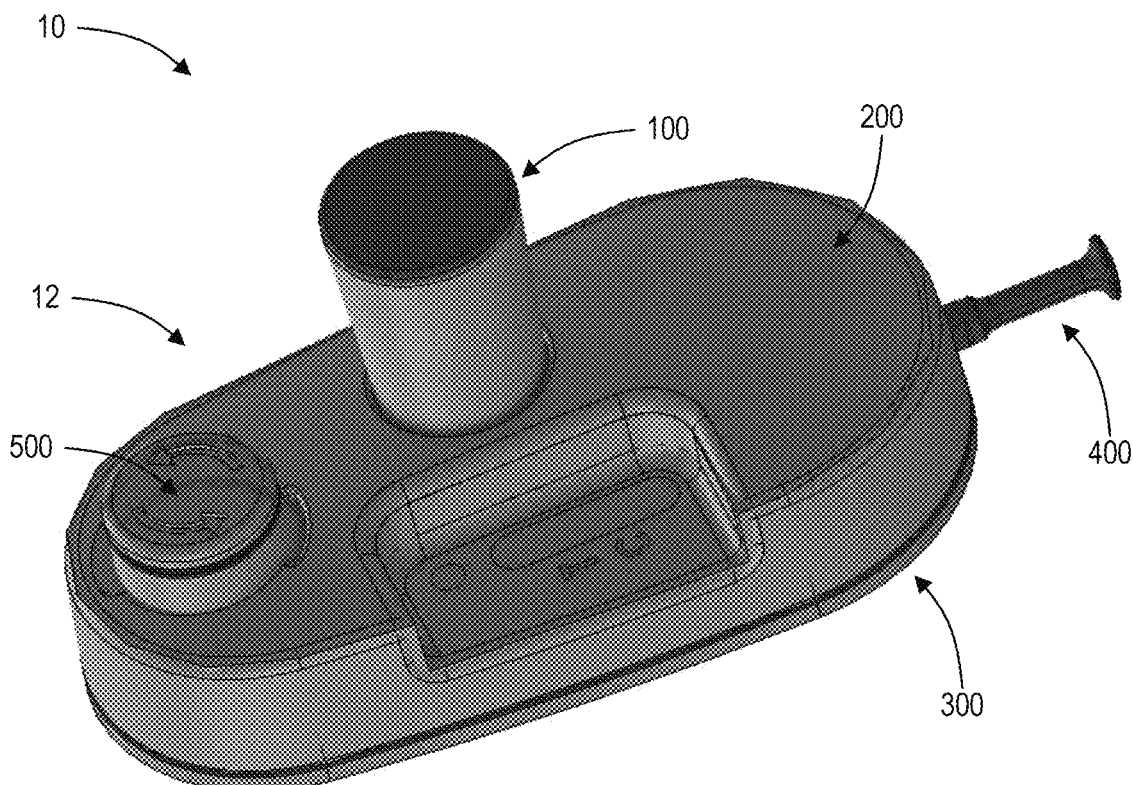
FIGS. 1A and 1B depict a dermal patch system in accordance with an exemplary embodiment of the present disclosure.

The present disclosure generally relates to a dermal patch that may be utilized to detect a biomarker in a physiological sample.

In some embodiments, a dermal patch may be used to perform a diagnostic test by detecting an analyte in a physiological sample. Dermal patches disclosed herein may allow a user to perform a diagnostic test in a variety of environments (e.g., in the home, in the field, in a medical facility, etc.).

Various terms are used herein in accordance with their ordinary meanings in the art, unless otherwise indicated.

The term "about," as used herein, denotes a deviation of at most 10% relative to a numerical value. For example, about 100 μm means in the range of 90 μm-110 μm.

The term "substantially," as used herein, refers to a deviation, if any, of at most 10% from a complete state and/or condition.

The term "subject" as used herein refers to a human subject or an animal subject (i.e., chicken, pig, cattle, dog, cat, etc.).

The term "physiological sample," as used herein, includes fluid drawn from a subject and includes, but is not limited to, blood and interstitial fluid.

The term "lancet," as used herein, refers broadly to an element that can be used to provide a passageway, or facilitate the production of a passageway, in the skin for drawing a physiological sample.

The term "transparent," as used herein, indicates that light can substantially pass through an object (e.g., a window) to allow visualization of a material disposed behind the object. For example, in some embodiments, a transparent object allows the passageway of at least 70%, or at least 80%, or at least 90% of visible light therethrough.

The term "vacuum," as used herein, refers to a pressure less than atmospheric pressure and more particularly to a pressure that can facilitate the movement of a fluid (e.g., a physiological sample) within a dermal patch.

The term "needle" as used herein, refers to a component with a pointed tip that is configured to pierce an outer surface of an element (e.g., skin of a subject) to provide a passageway.

The term "diagnostic test strip" refers to a band/piece/strip of paper or other material configured to determine the presence or absence of a biomarker in a physiological sample.

The term "biomarker" refers to a biological molecule that is an indicator of a biological state or condition.

The present disclosure generally relates to a device, which is herein also referred to as a dermal patch or a dermal patch system, for detecting a biomarker in a physiological sample (e.g., bodily fluids such as blood, interstitial fluids, etc.) from a subject. In some embodiments discussed below, such a dermal patch system can include a cartridge that can be affixed to a subject's skin (e.g., via an adhesive layer) and a separate lancet that can be engaged with the cartridge to puncture the skin, thereby providing a passageway for extracting the physiological sample. As discussed in more detail below, the lancet can include a housing in which at least one needle that is configured for puncturing the skin is disposed. The lancet can further include a mechanism that can be transitioned between at least two states. In one state (herein referred to as a locked state), the mechanism retains the needle within the lancet in an undeployed position when the lancet is not engaged with the cartridge. When the lancet is coupled to the cartridge, the mechanism transitions to a second state (herein referred to as a released state). In the released state, the mechanism allows the needle to be deployed for puncturing the skin. For example, in some embodiments, the mechanism can include an upper locking portion that can retain an upper spring that is coupled to a needle platform (to which a needle is mounted) in a compressed state, thereby preventing the needle from transitioning into a deployed position. Further, the mechanism can include an upper interference member that prevents the movement of the needle platform when the mechanism is in the locked state.

The engagement of the lancet with the cartridge results in an automatic transition of the mechanism from the locked state to the released state, which transitions the needle into a deployed position in which the needle extends beyond the lancet and the cartridge housing to puncture the subject's skin. In some embodiments, the engagement of the lancet with the cartridge causes the upper locking member to release the needle platform, which in turn allows the upper spring to decompress and thus push down the needle platform thereby deploying the needle. In some embodiments, the mechanism can further include a lower interference member that restricts the downward movement of the needle platform, when the needle platform is released. In this manner the extent of the penetration of the needle into the skin can be controlled. In certain embodiments, the mechanism can also include a lower locking member that retains a lower spring in a compressed state. The downward movement of the needle platform can cause the release of the lower locking member to allow the lower spring to decompress and exert a restoring force on the needle platform to cause the retraction of the needle into the lancet housing.

In this manner, the lancet remains safe before it is engaged with the cartridge as the lancet is not capable of deploying the needle when the lancet is not engaged with the cartridge. Furthermore, in this manner, the lancet remains safe after drawing a physiological sample as the needle automatically retracts back into the lancet after being deployed.

Figure 1B:
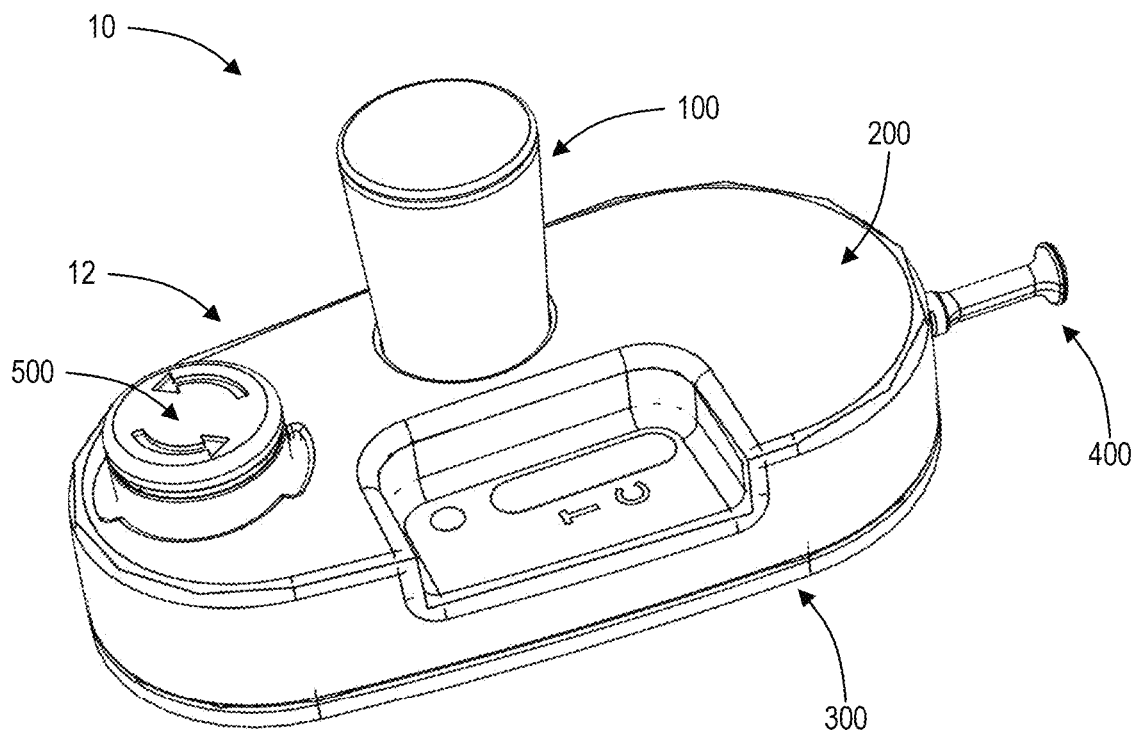
Figure 2A:
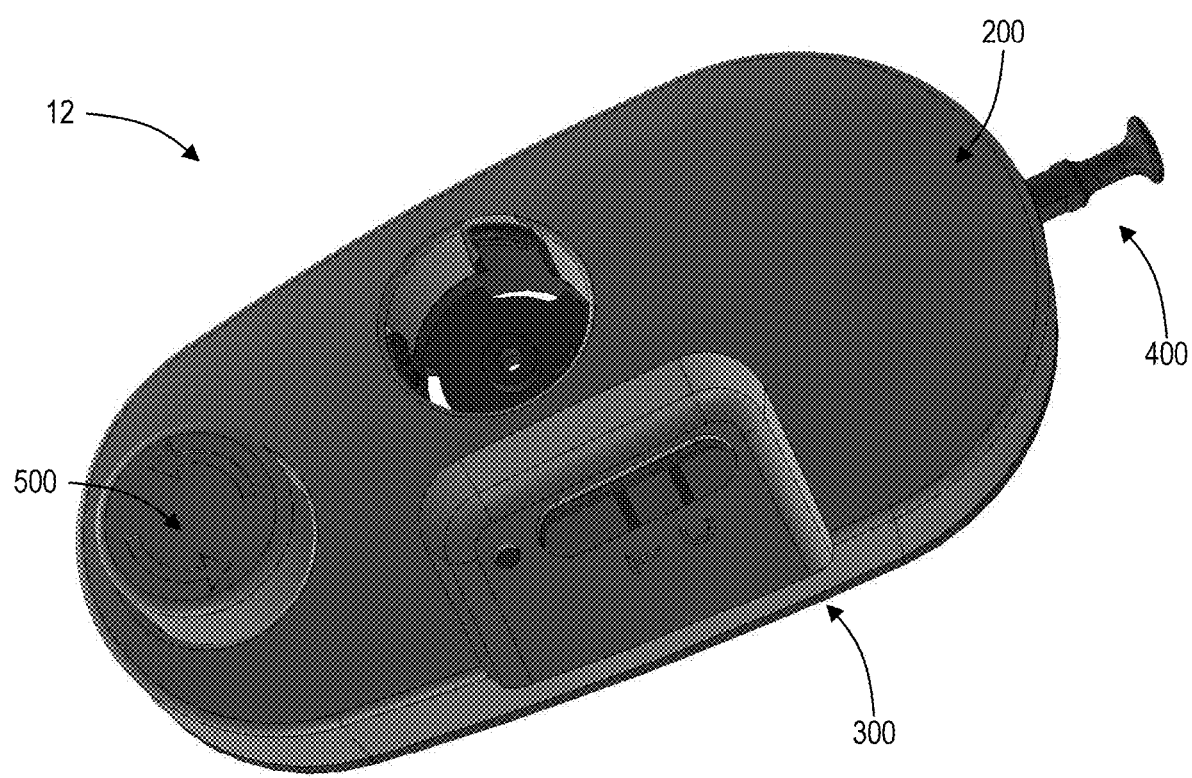
Figure 2B:
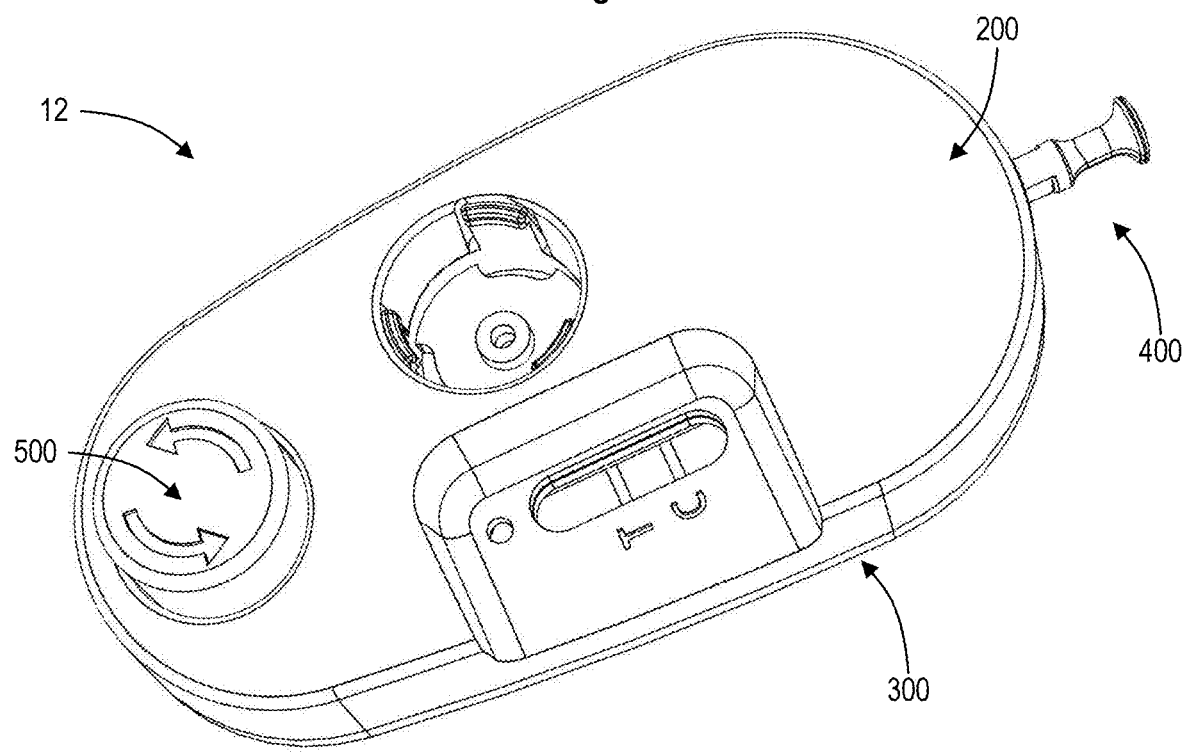
Figure 4A:
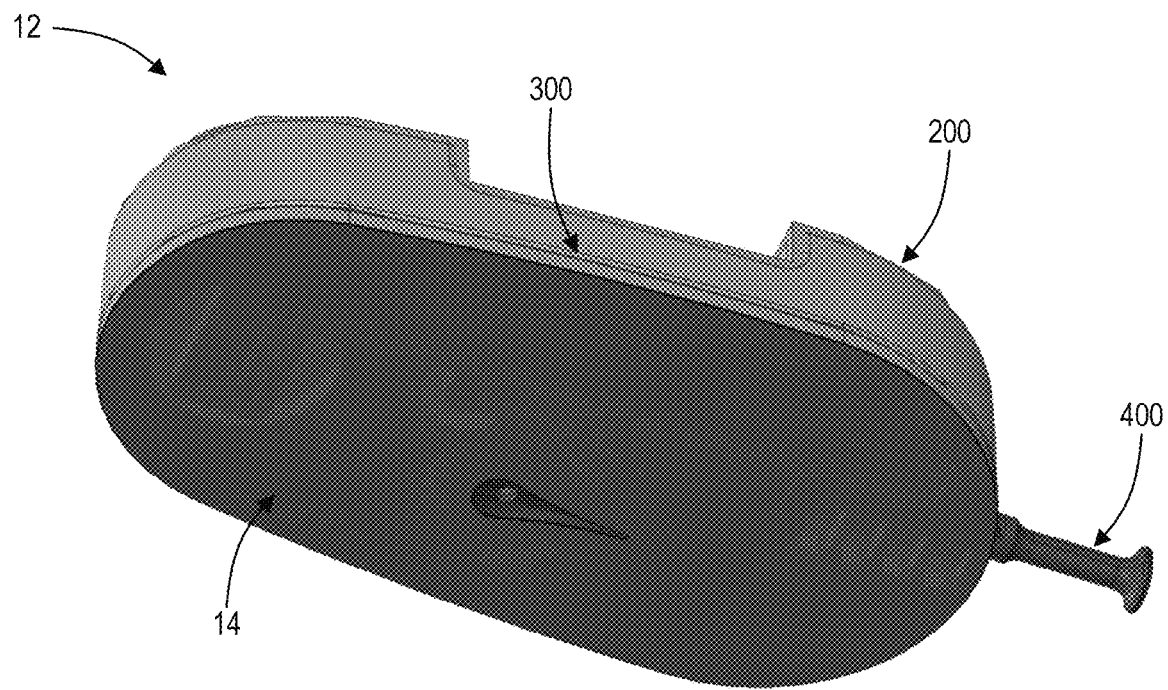
Figure 4B:
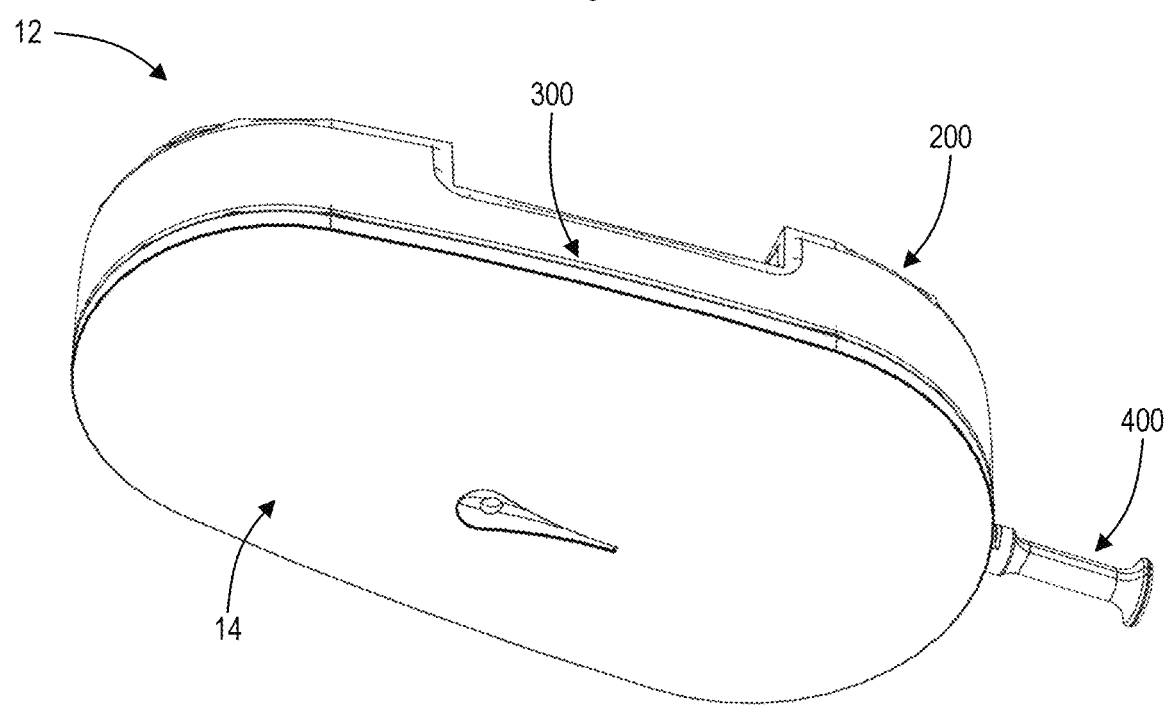
Figure 5A:
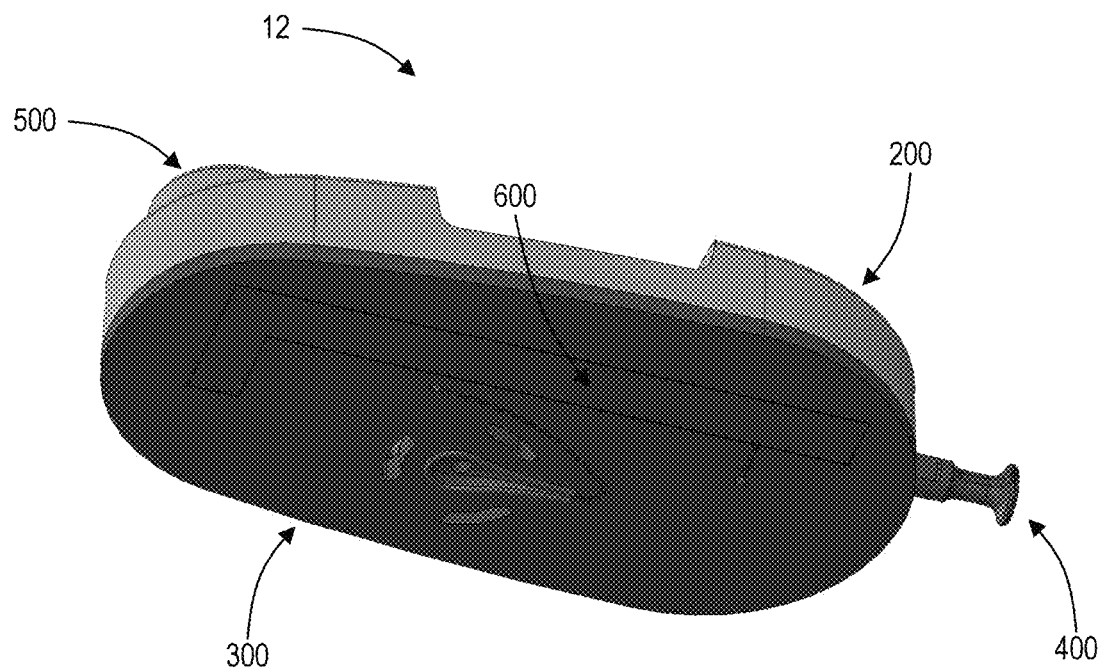
Figure 5B:
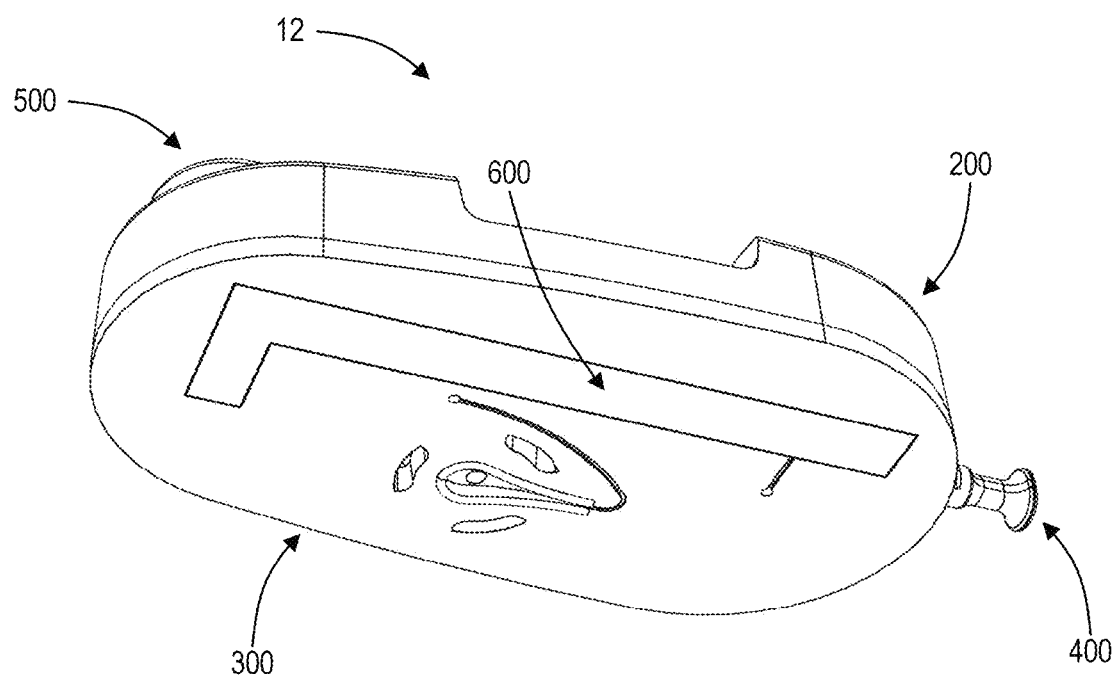

Referring now to FIGS. 1A and 1B, a dermal patch system 10 is shown in accordance with an exemplary embodiment. The dermal patch system 10 includes a cartridge 12 that can be affixed to a subject's skin via an adhesive layer 14. (FIGS. 4A and 4B). The dermal patch system 10 also includes a lancet 100 that can engage with the cartridge 12 to deploy a needle disposed within the lancet 100.

The dermal patch system 10 includes a lancet 100, a cartridge 12 that can be affixed to a subject's skin via an adhesive layer 14 (FIGS. 4A and 4B). As will be discussed in further detail herein, the lancet 100 can engage with the cartridge 12 to deploy a needle disposed within the lancet housing to puncture the subject's skin thereby drawing a physiological sample from the subject.

The cartridge 12 includes a cover 200 and a base 300 that can couple to the cover 200. For example, the cover 200 and the base 300 can be formed as two or more separate components that are removably coupled to one another (e.g., via a snap fitting). In other embodiments, the cover 200 and the base 300 form an integral unitary cartridge 12. In some of these embodiments, the cover 200 can be bonded or coupled to the base 300 via an adhesive, laser welding, heat sealing, heat activated adhesive, etc. The dermal patch system 10 also includes a vacuum pin 400. As will be discussed in further detail herein, the vacuum pin 400 can be disposed within the cartridge 12 and is configured to create a vacuum within the cartridge 12.

The cartridge 12 may be formed using a variety of suitable materials including, but not limited to, polymeric materials (e.g., polyolefins, polyethylene terephthalate (PET), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, photocross linkable polymers, etc.). In some embodiments, some of the cover 200 may be formed of poly(dimethylsiloxane) (PDMS) to allow visibility of components disposed within the cartridge 12.

Figure 6A:
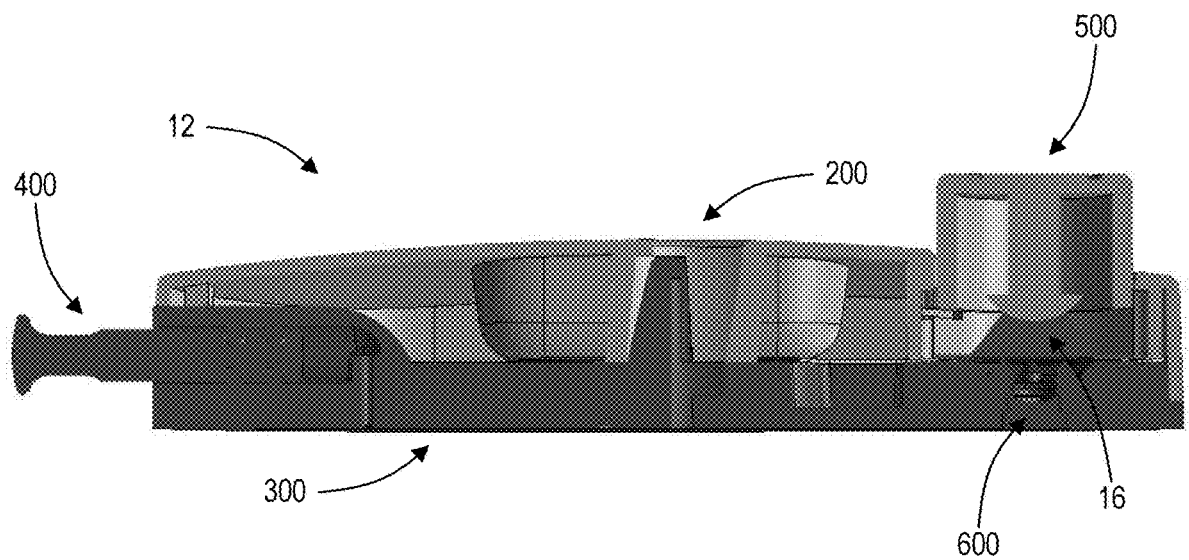
Figure 6B:
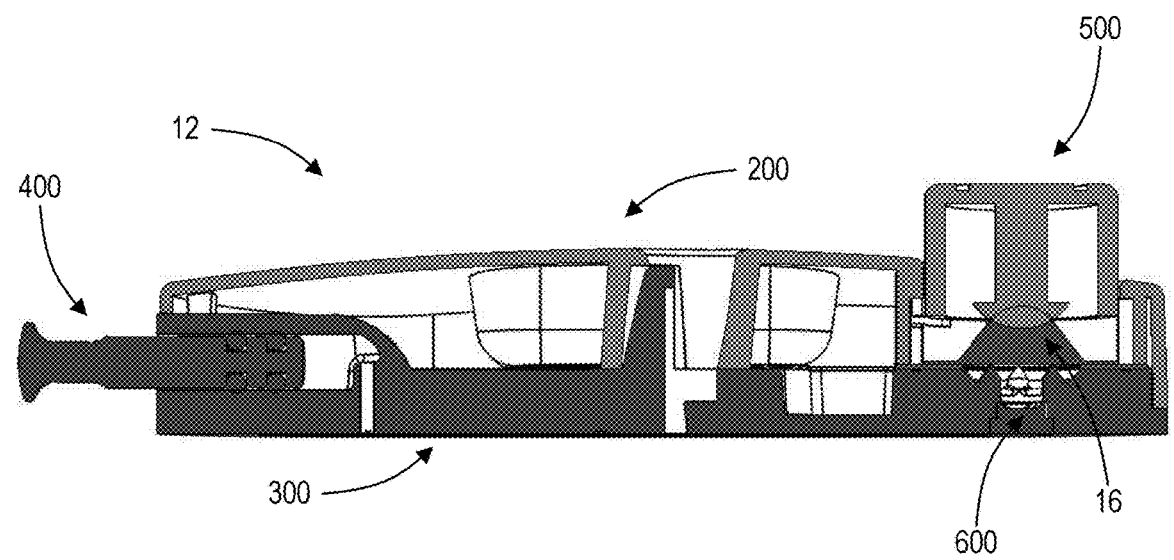
Figure 7A:
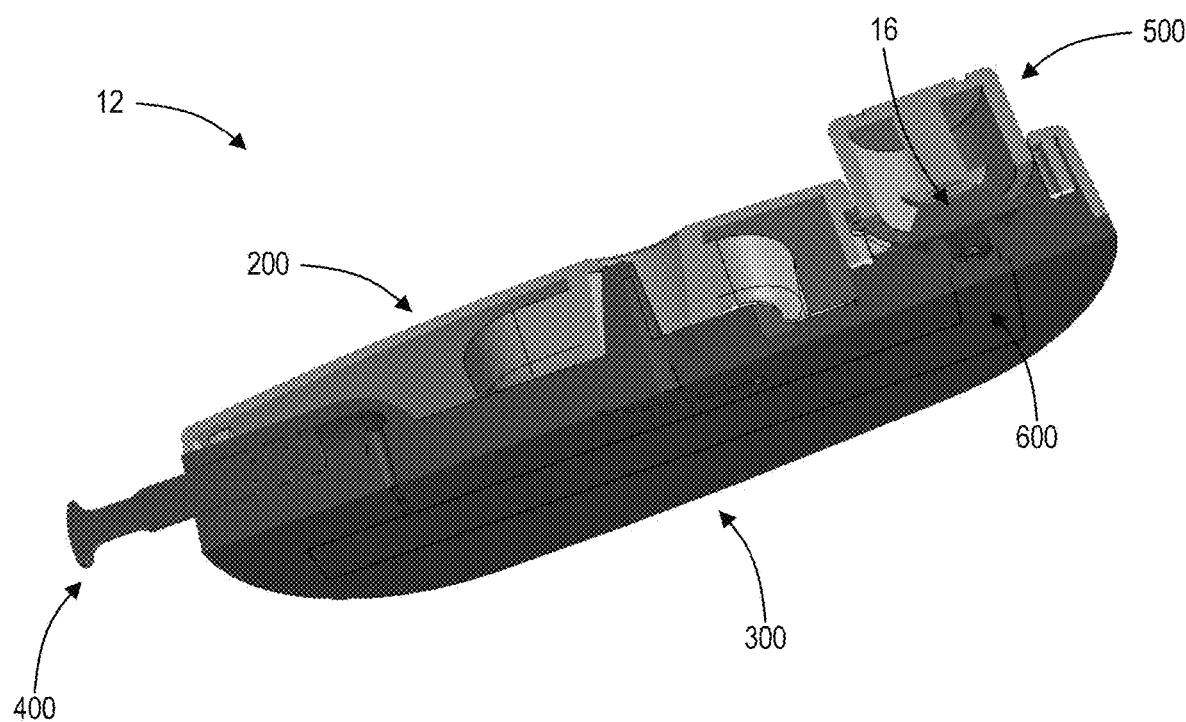
Figure 7B:
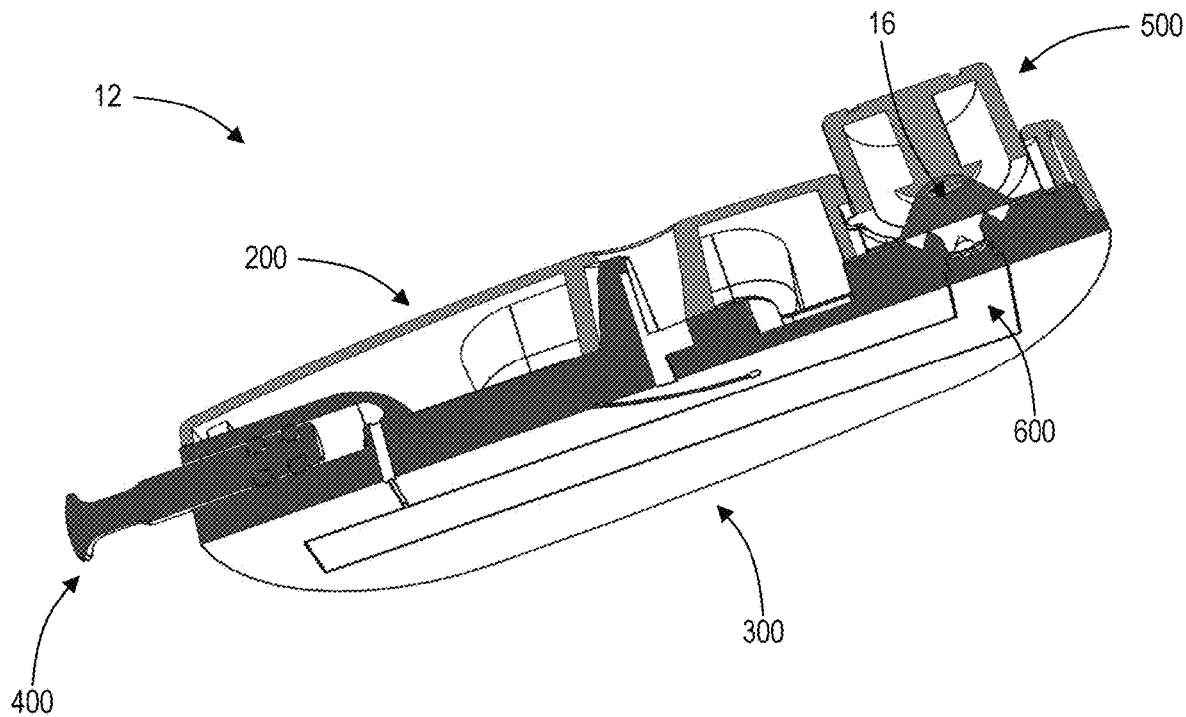

With particular reference to FIGS. 6A and 6B, the cartridge 12 further includes a sealed processing fluid pack 16 that is disposed in the base 300 of the cartridge 12 and a button 500 that extends through the cover 200. The processing fluid pack 16 is disposed within the cartridge 12 and contains a processing fluid (e.g., TBS-T, Tris Buffered Saline-Tween, and TENT, Tris Buffered saline with EDTA, etc.) for processing a physiological sample drawn form a subject. The processing fluid pack 16 is formed of a frangible membrane. As will be discussed in further detail herein, the button 500 is configured to apply a pressure upon the processing fluid pack 16 which causes the processing fluid pack 16 to rupture thereby releasing the processing fluid.

The cartridge 12 also includes a test strip support 600 that is configured to retain a diagnostic test strip 18. The test strip support 600 is configured to couple to the base 300 such that the diagnostic test strip 18 (FIG. 8B) is disposed within the cartridge 12 when the test strip support 600 is coupled to the base 300. The cartridge 12 further includes a film 20 (FIG. 8B) disposed on the base 300. As will be discussed in further detail herein, the film 20 seals at least a portion of the base 300.

Figure 9:
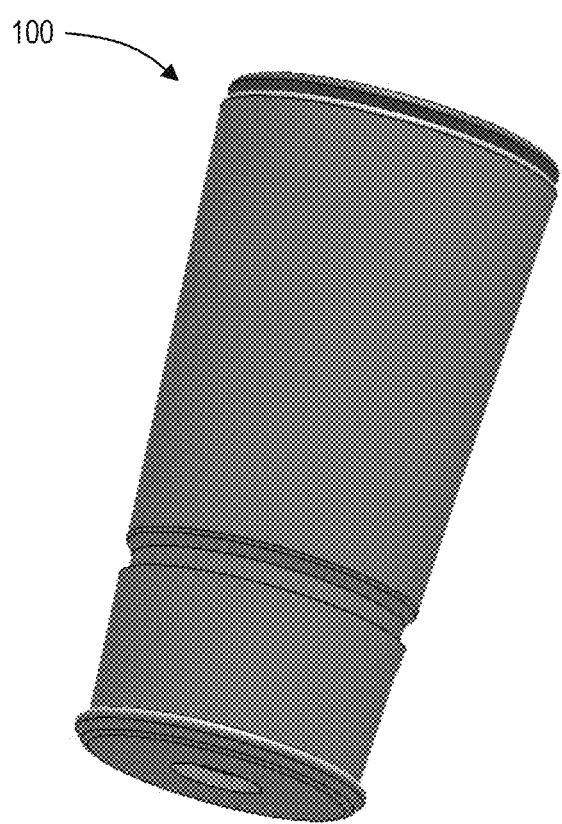
FIGS. 9 and 10 depict a lancet of the dermal patch system in accordance with an exemplary embodiment of the present disclosure
Figure 10:
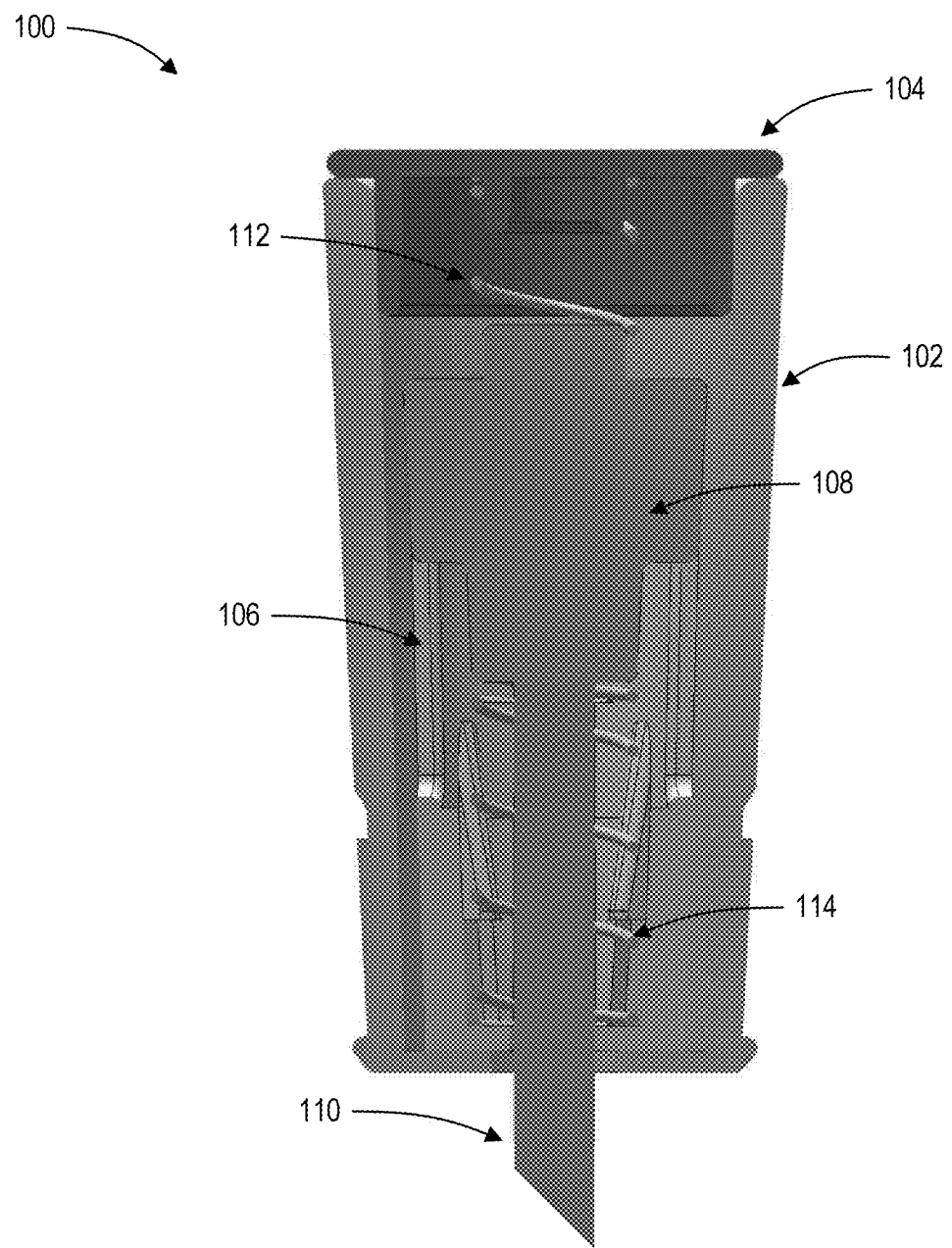

Referring now to FIGS. 9 and 10, the lancet 100 is shown in accordance with an exemplary embodiment. The lancet 100 includes a housing 102 in which various components of the lancet are disposed and a cap 104 that is coupled to the housing 102. The lancet 100 can further include an inner sleeve 106 within the housing 102 and a needle frame 108 that is disposed within the inner sleeve 106 and onto which a needle 110 is mounted. The lancet 100 also can include an injection spring 112 and a retraction spring 114 that move a needle of the lancet between various positions.

With particular reference to FIGS. 11A and 11B, the housing 102 includes a side wall 116 and a bottom wall 118. The side wall 116 includes an outer surface 116a and an opposed inner surface 116b. The bottom wall 118 includes an outer surface 118a and an opposed inner surface 118b. The side wall 116 extends vertically from the bottom wall 118. The side wall 116 has a generally cylindrical shape and the bottom wall 118 is generally circular in shape and is concentric relative to a longitudinal axis of the generally cylindrical side wall and covers a lower opening formed by the generally cylindrical side wall. The inner surface 116b of the side wall 116 and the inner surface 118b of the bottom wall 118 define an inner volume 120.

The outer surface 116a defines a notch 122 that extends circumferentially around the outer surface 116a of the side wall 116. As will be discussed in further detail herein, the notch 122 is shaped and dimensioned to couple to a locking member of the cartridge 12 via a snap fit. The housing 102 further includes a rim 124 that extends circumferentially around the outer surface 116a of the side wall 116. The inner surface 116b defines a first and second column 126 that extend vertically from the inner surface 118b of the bottom wall 118. The columns 126 includes an inner surface 126a and a top surface 126b. The inner surface 126a extends vertically between the inner surface 118b of the bottom wall 118 and the top surface 126b. The top surface 126b extends longitudinally between the inner surface 116b of the side wall 116 and the inner surface 126a.

As will be discussed in further detail herein, before the lancet 100 is inserted into the cartridge 12 the columns 126 retain the needle 110 of the lancet 100 in an undeployed position.

The bottom wall 118 defines an aperture 128 that extends through the bottom wall 118. Stated another way, the aperture 128 extends between the outer surface 118a and the inner surface 118b of the bottom wall 118. As will be discussed in further detail herein, when the lancet is activated via engagement with the cartridge 12, the needle of the lancet 100 is activated to extend through the aperture 128 and puncture the subject's skin thereby providing a passageway through which a physiological sample can be drawn from a subject.

Figure 12A:
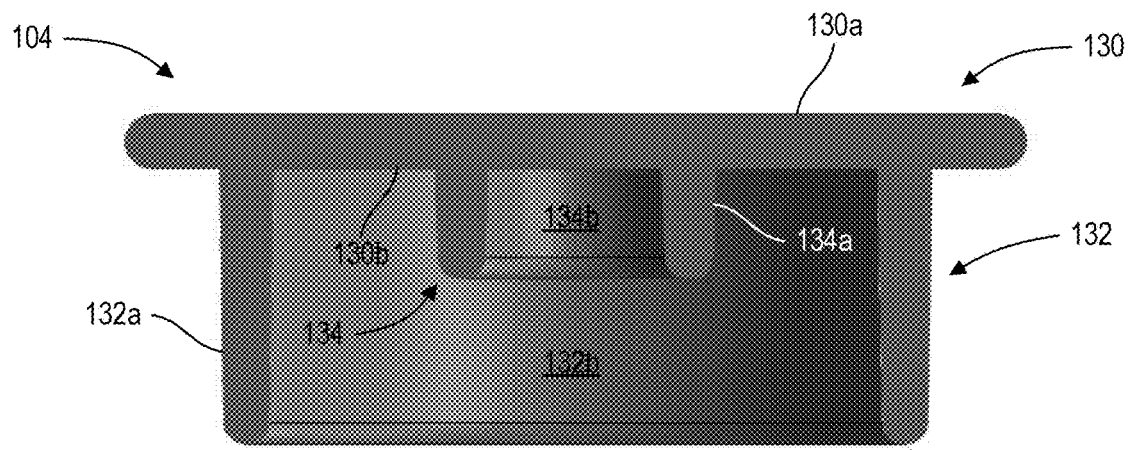
FIGS. 12A and 12B depict a cap of the lancet in accordance with an exemplary embodiment of the present disclosure.
Figure 12B:
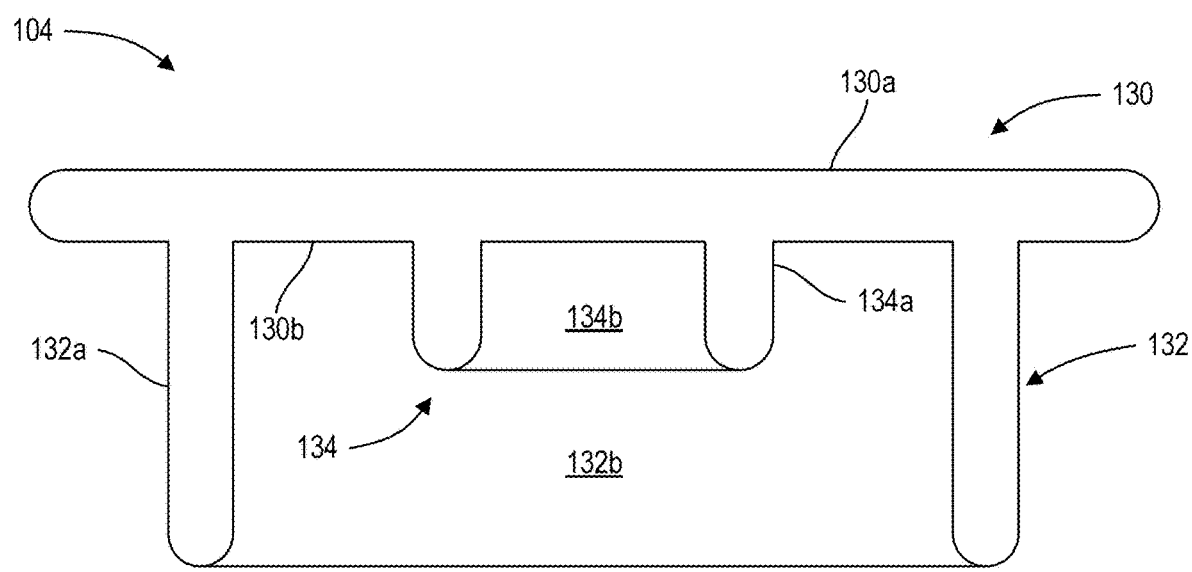

With particular reference to FIGS. 12A and 12B the cap 104 includes a top wall 130 with an outer surface 130a and an opposed inner surface 130b. The cap 104 also includes a side wall 132 with an outer surface 132a and an opposed inner surface 132b. The top wall 130 extends longitudinally from and perpendicular to the side wall 132. The side wall 132 extends vertically from and perpendicular to the top wall 130. The top wall 130 and the side wall 132 are generally circular in shape and are concentric with one another. The cap 104 also includes an inner cylinder 134 with an outer surface 134a and an opposed inner surface 134b. The inner cylinder 134 extends vertically from and perpendicular to the top wall 130. The inner cylinder 134 is concentric with the top wall 130 and the side wall 132.

When the cap 104 is coupled to the housing 102 the side wall 132 extends into the inner volume 120 of the housing 102 and at least a portion of the side wall 132 contacts the inner surface 116b of the side wall 116 such that the cap 104 couples to the housing 102 via an interference fit.

Figure 13:
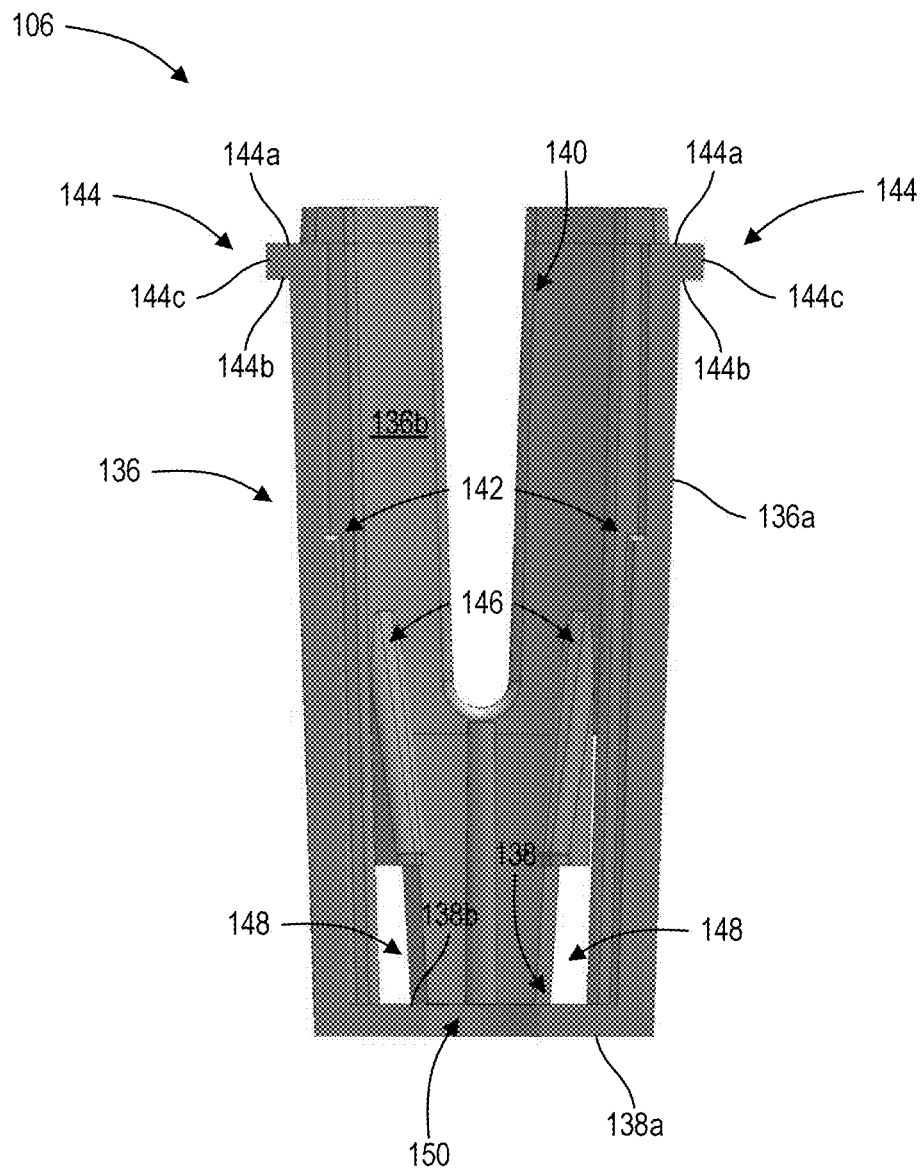
FIG. 13 depicts an inner sleeve of the lancet in accordance with an exemplary embodiment of the present disclosure.

As depicted in FIG. 13, the inner sleeve 106 includes a side wall 136 and a bottom wall 138. The side wall 136 includes an outer surface 136a and an opposed inner surface 136b. The bottom wall 138 includes an outer surface 138a and an opposed inner surface 138b. The side wall 136 extends vertically from the bottom wall 138. The side wall 136 is substantially cylindrical and the bottom wall 138 are generally circular in shape and are concentric with one another. The inner surface 136b of the side wall 136 and the inner surface 138b of the bottom wall 138 define an inner volume 140. The inner surface 136b defines a plurality of columns 142 each of which extends vertically from and perpendicular to the inner surface 138b of the bottom wall 138. As will be discussed in further detail herein, when the needle frame 108 is in a deployed position, a portion of the needle frame 108 rests upon the columns 142.

The inner sleeve 106 further includes a plurality of ledges 144 that extend circumferentially about the side wall 136. Each ledge 144 includes a top surface 144a, an opposed bottom surface 144b and an outer surface 144c that extends between the top surface 144a and the bottom surface 144b. The inner sleeve 106 also includes a plurality of locking members 146 that extend from the inner surface 136b of the side wall 136. As will be discussed in further detail herein, the proximal end of the locking members 146 retains the retraction spring 114 in a compressed state in absence of engagement between the lancet 100 and the cartridge 12. The side wall 136 further defines a plurality of openings 148 that extend through the side wall 136. Stated another way, the openings 148 extend between the outer surface 136a and the inner surface 136b of the side wall 136. Each of the openings 148 are aligned with a proximal end of a locking member 146 to allow the proximal end of a locking member 146 to extend therethrough.

The bottom wall 138 defines an aperture 150 that extends through the bottom wall 138. Stated another way, the aperture 150 extends between the outer surface 138a and the inner surface 138b of the bottom wall 138. The aperture 150 is concentric with the aperture 128 of the housing 102. As will be discussed in further detail herein, when in a deployed position, the needle 110 of the lancet 100 extends through the aperture 150 of the inner sleeve 106 as well as the aperture 128 of the housing 102.

Figure 14:
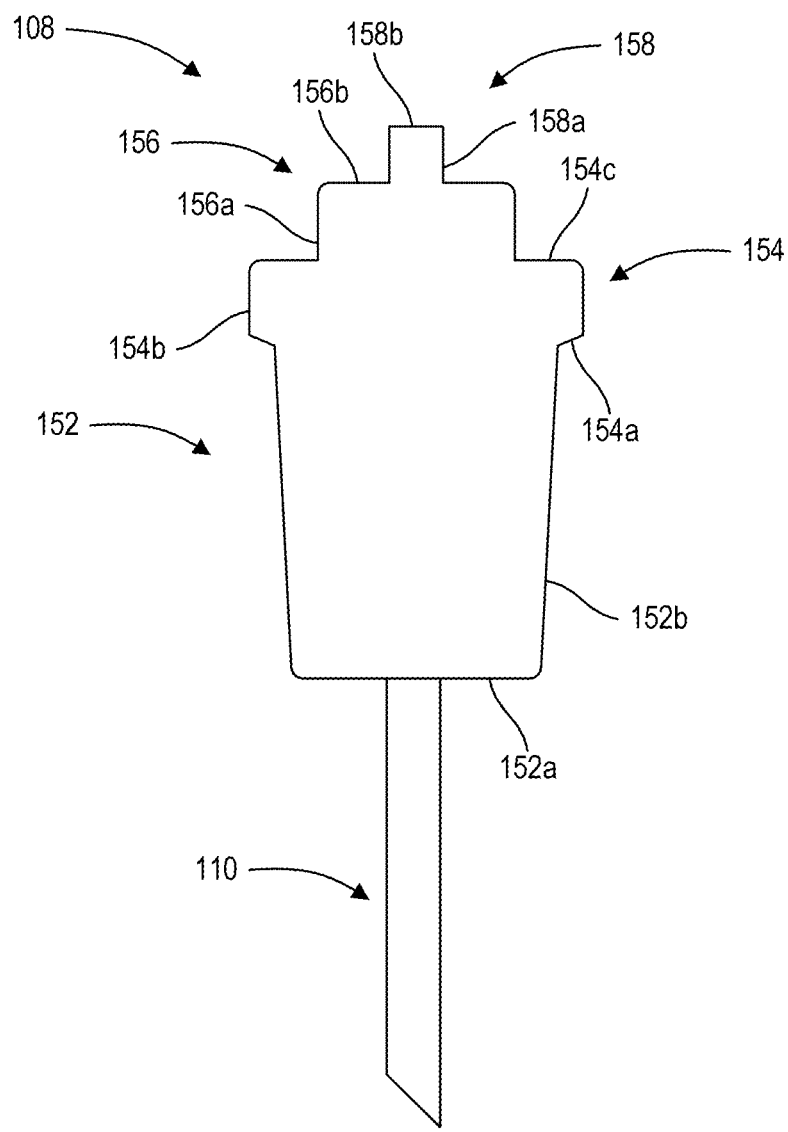
FIG. 14 depicts a needle frame in accordance with an exemplary embodiment of the present disclosure.
Figure 15A:
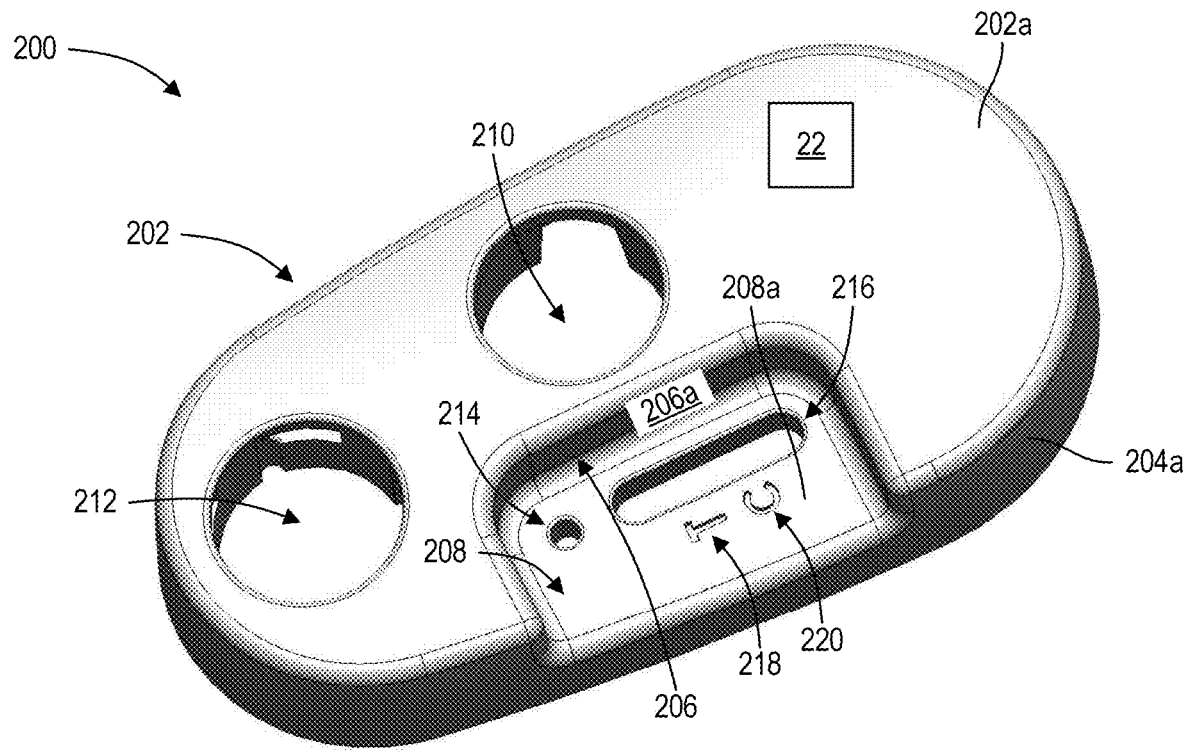
Figure 15B:
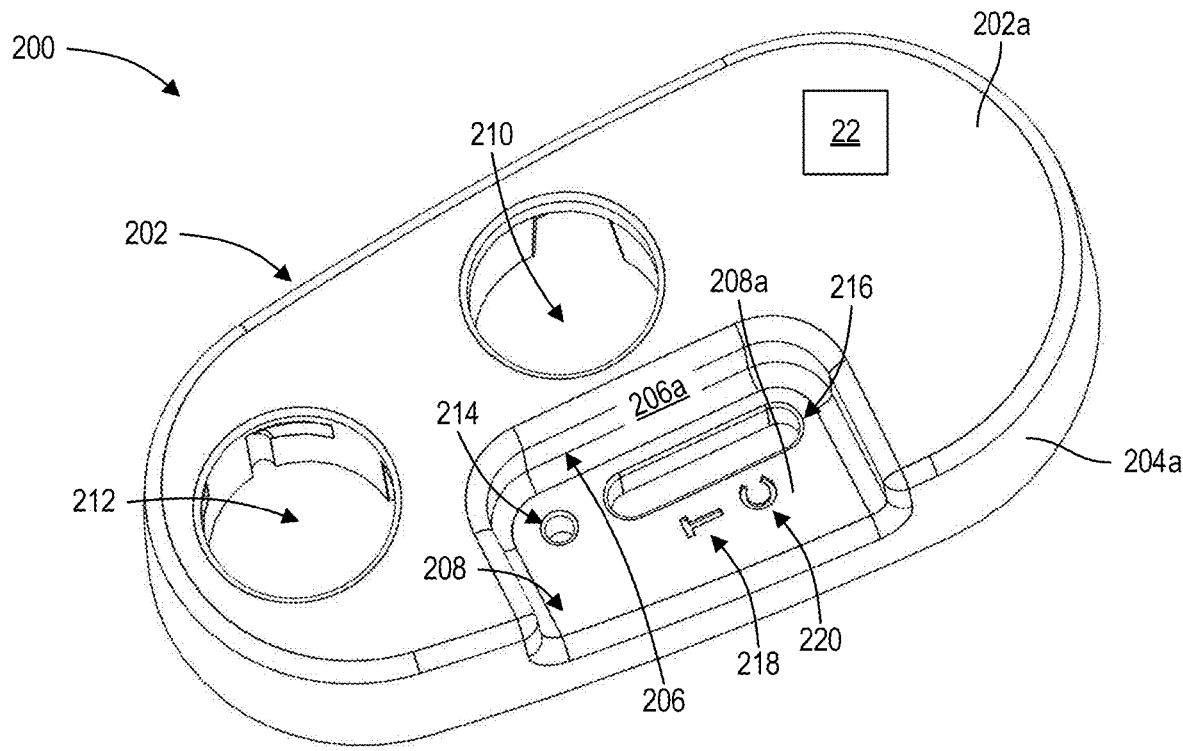

As depicted in FIG. 14, the needle frame 108 includes a first cylinder 152 and a second cylinder 154 disposed vertically above the second cylinder 154. The first cylinder 152 includes a bottom surface 152a and an outer surface 152b. The second cylinder 154 is disposed vertically above the first cylinder 152 and the third cylinder 156 is disposed vertically above the second cylinder 154. The first cylinder 152 includes a bottom surface 152*a* and an outer surface 152*b* and the second cylinder 154 includes a bottom surface 154*a*, an outer surface 154*b* and a top surface 154*c*. The third cylinder 156 includes an outer surface 156*a* and a top surface 156*b*. Similarly, the protrusion 158 includes an outer surface 158*a* and a top surface 158*b*.

The bottom surface 152*a* of the first cylinder 152 extends circumferentially about the outer surface 152*b* of the first cylinder. The outer surface 152*b* of the first cylinder 152 extends vertically between the bottom surface 152*a* of the first cylinder 152 and the bottom surface 154*a* of the second cylinder 154. The bottom surface 154*a* of the second cylinder 154 extends at an angle longitudinally between the outer surface 152*b* of the first cylinder and the outer surface 154*b* of the second cylinder 154. The outer surface 154*b* extends vertically between the bottom surface 154*a* and the top surface 154*c* of the second cylinder 154. The top surface 154*c* of the second cylinder 154 extends longitudinally between the outer surface 154*b* of the second cylinder and the outer surface 156*a* of the third cylinder 156. The outer surface 156*a* extends vertically between the top surface 154*c* of the second cylinder and the top surface 156*b* of the third cylinder. The top surface 156*b* of the third cylinder extends longitudinally between the outer surface 156*a* of the third cylinder 156 and the outer surface 158*a* of the protrusion 158. The outer surface 158*a* extends vertically between the top surface 156*b* of the third cylinder and the top surface 158*b* of the protrusion 158. The top surface 158*b* of the protrusion 158 extends across a proximal end of the outer surface 158*a*.

The injection spring 112 (FIG. 10) extends vertically between the cap 104 and the needle frame 108. More specifically, a distal end of the injection spring 112 contacts the inner surface 130*b* of the top wall 130 and a proximal end of the injection spring 112 contacts the top surface 154*c* of the second cylinder 154. The distal end of the injection spring 112 extends circumferentially around the outer surface 134*a* of the inner cylinder 134. The proximal end of the injection spring 112 extends circumferentially around the third cylinder 156 and around the protrusion 158.

The needle frame 108 supports the needle 110. In some embodiments, the needle 110 is molded into the first cylinder 152 or is attached to the bottom surface 152*a* of the first cylinder 152 (e.g., via an adhesive).

Referring now to FIGS. 15A and 15B-22A and 22B, the cover 200 is shown in accordance with an exemplary embodiment.

In this embodiment, the cover 200 includes a top wall 202 and a side wall 204. The side wall 204 extends vertically from and perpendicular to the top wall 202. The top wall 202 extends longitudinally from and perpendicular to the side wall 204. The top wall 202 includes an outer surface 202*a* and an opposed inner surface 202*b*. The side wall 204 includes an outer surface 204*a* and an opposed inner surface 204*b*.

The cover 200 further includes a vertical wall 206 and a horizontal wall 208. The vertical wall 206 extends vertically between and perpendicular to the top wall 202 and the horizontal wall 208. The horizontal wall 208 extends longitudinally between and perpendicular to the side wall 204 and the vertical wall 206. The vertical wall 206 includes an outer surface 206*a* and an opposed inner surface 206*b*. The horizontal wall 208 includes an outer surface 208*a* and an opposed inner surface 208*b* (FIG. 17B).

The top wall 202 defines a lancet aperture 210 and a button aperture 212. The lancet aperture 210 and the button aperture 212 are generally circular in shape and extend through the top wall 202. Stated another way, the lancet aperture 210 and the button aperture 212 extend between the outer surface 202*a* and the inner surface 202*b* of the top wall 202. The lancet aperture 210 is shaped and dimensioned to accommodate at least a portion of the lancet 100. As will be discussed in further detail herein, the lancet aperture 210 allows the lancet 100 to couple to the base 300. That is, the lancet aperture 210 is shaped to accommodate the lancet 100 such that the lancet 100 can be engaged with the cartridge 12.

The horizontal wall 208 defines a sample viewing aperture 214 and a test strip viewing aperture 216. The sample viewing aperture 214 and the test strip viewing aperture 216 extend through the horizontal wall 208. Stated another way, the sample viewing aperture 214 and the test strip viewing aperture 216 extend between the outer surface 208*a* and the inner surface 208*b*. The sample viewing aperture 214 and the test strip viewing aperture 216 allow a user of the dermal patch system 10 to view components (e.g., the diagnostic test strip 18) disposed within the dermal patch system 10. In some embodiments, the cover 200 can further include a transparent window(s) (not shown), e.g., formed of PDMS, that extends across the sample viewing aperture 214 and the test strip viewing aperture 216.

The horizontal wall 208 further includes a test result indicator 218 and a control indicator 220 disposed on the outer surface 208*a*. As will be discussed in further detail herein, the test result indicator 218 and the control indicator 220 can be used to determine the presence or absence of a biomarker.

Figure 16B:
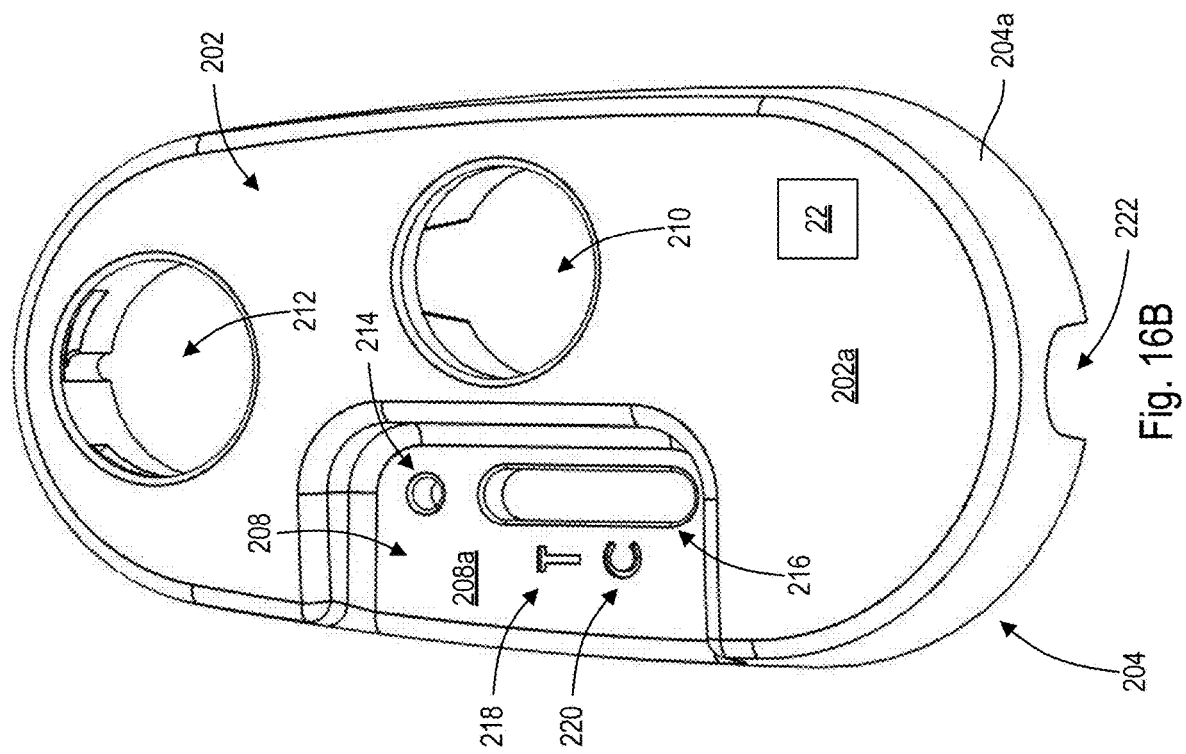
Figure 16A:
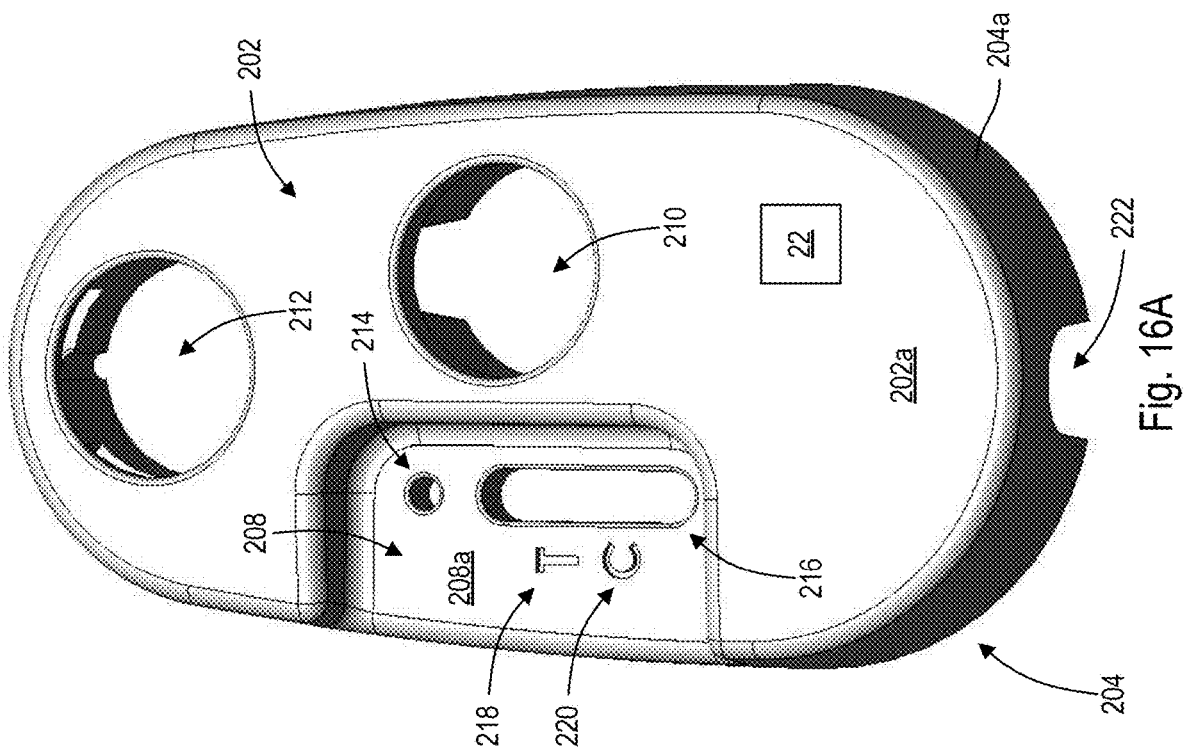

With particular reference to FIGS. 16A and 16B, the side wall 204 defines U-shaped opening 222, which extends through the side wall 204. Stated another way, the U-shaped opening 222 extends between the outer surface 204*a* and the inner surface 204*b* of the side wall 204. The U-shaped opening 222 is shaped and dimensioned to accommodate at least a portion of the vacuum pin 400. As will be discussed in further detail herein, U-shaped opening 222 allows the vacuum pin 400 to be received by a receptacle (which can be in the form of a channel) within the cartridge 12. That is, the U-shaped opening 222 is shaped to accommodate the vacuum pin 400 such that at least a portion of the vacuum pin 400 can extend through the side wall 204 to be disposed within a receptacle provided in the base 300.

Figure 18B:
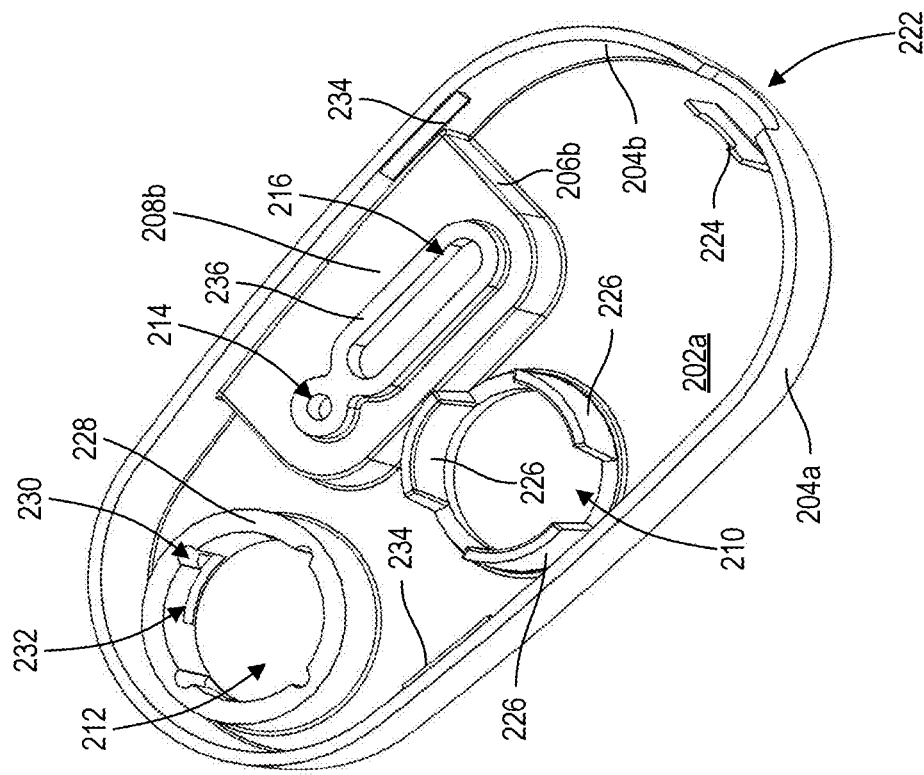
Figure 18A:
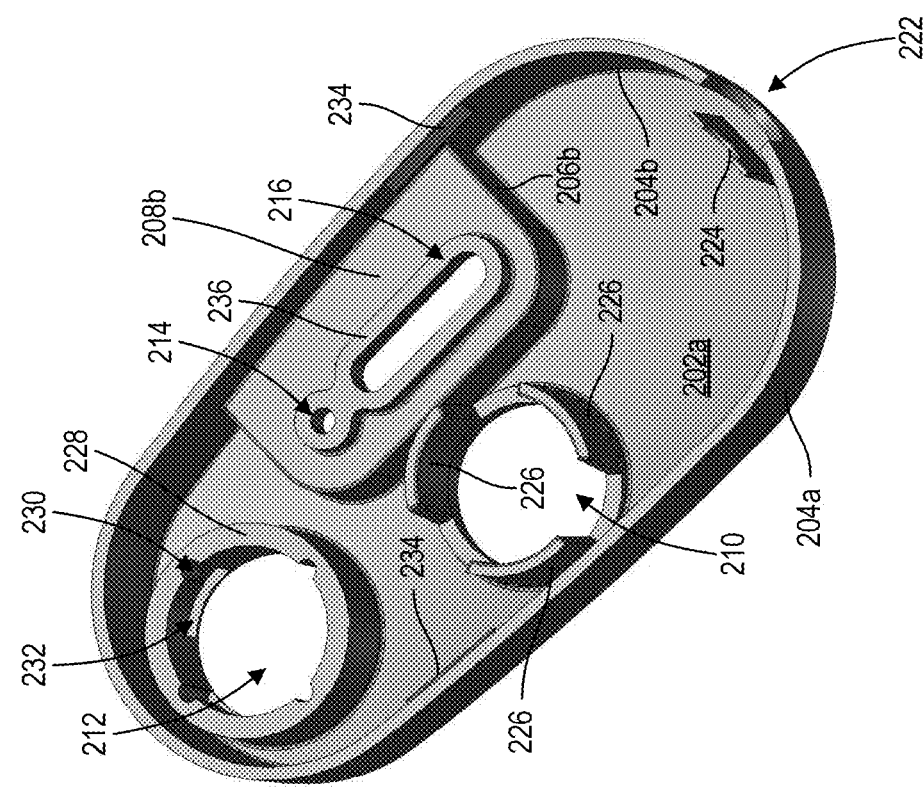
Figure 20B:
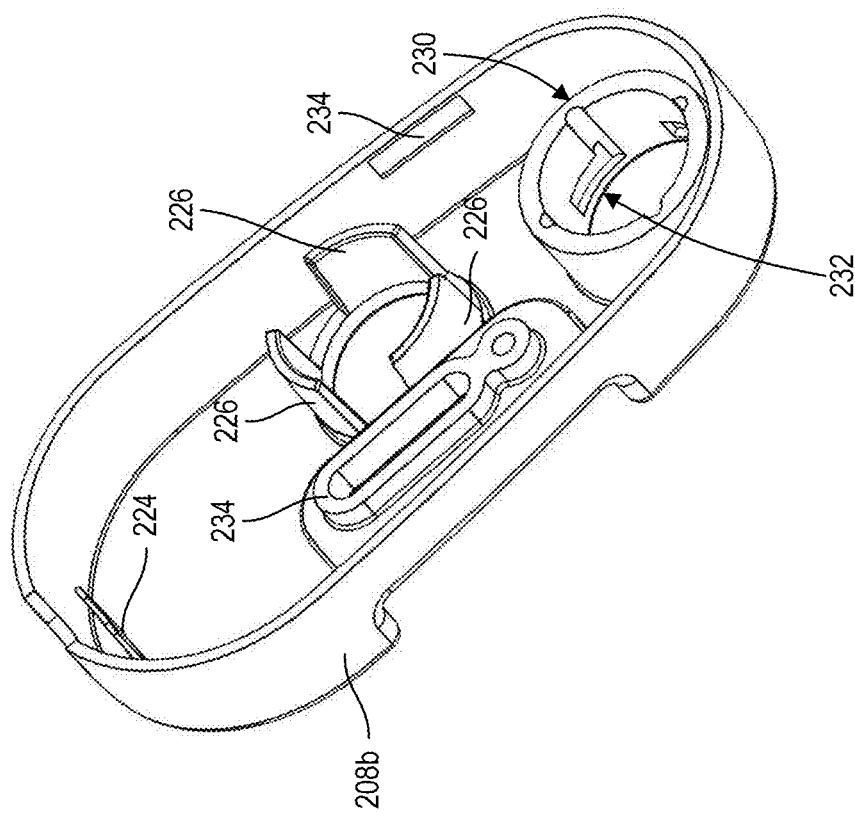
Figure 20A:
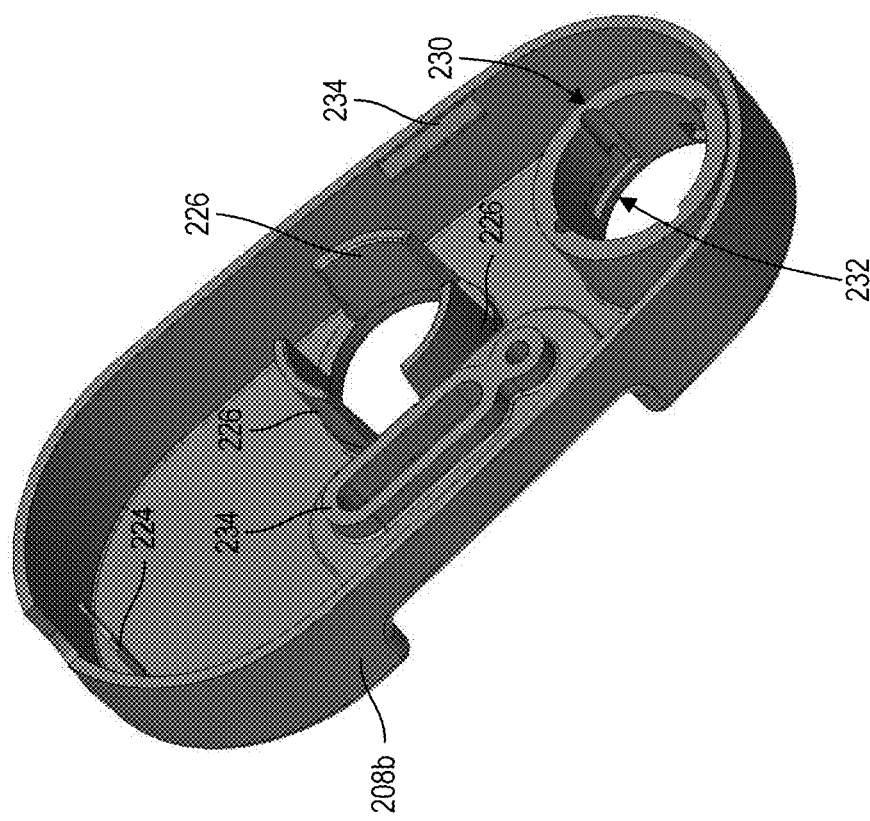
Figure 21B:
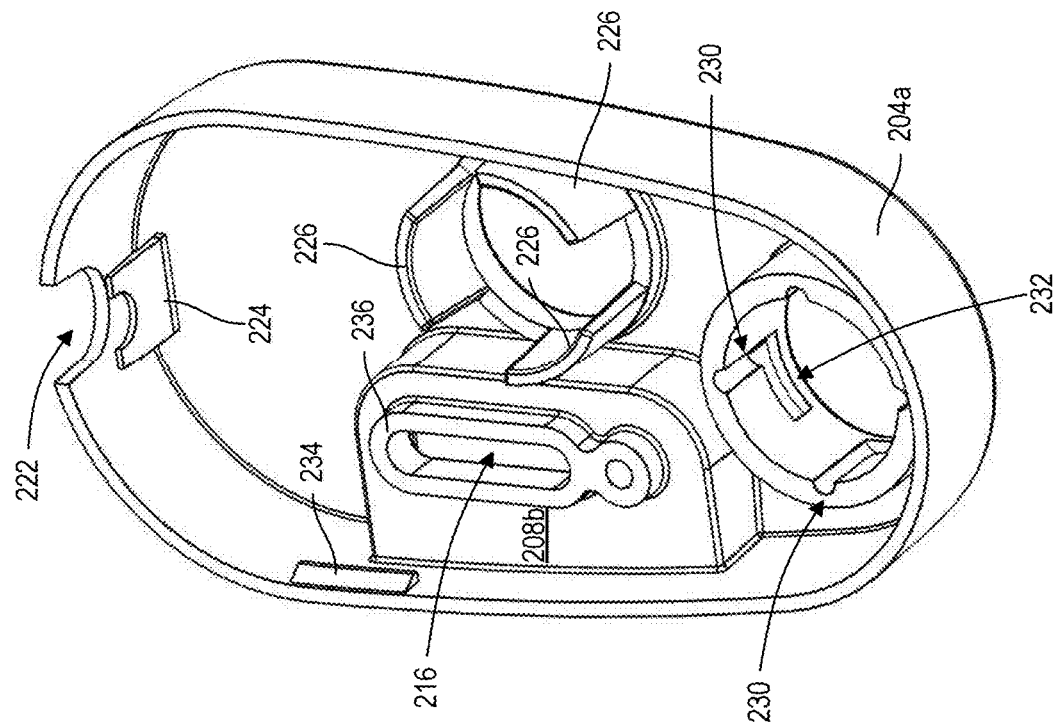
Figure 21A:
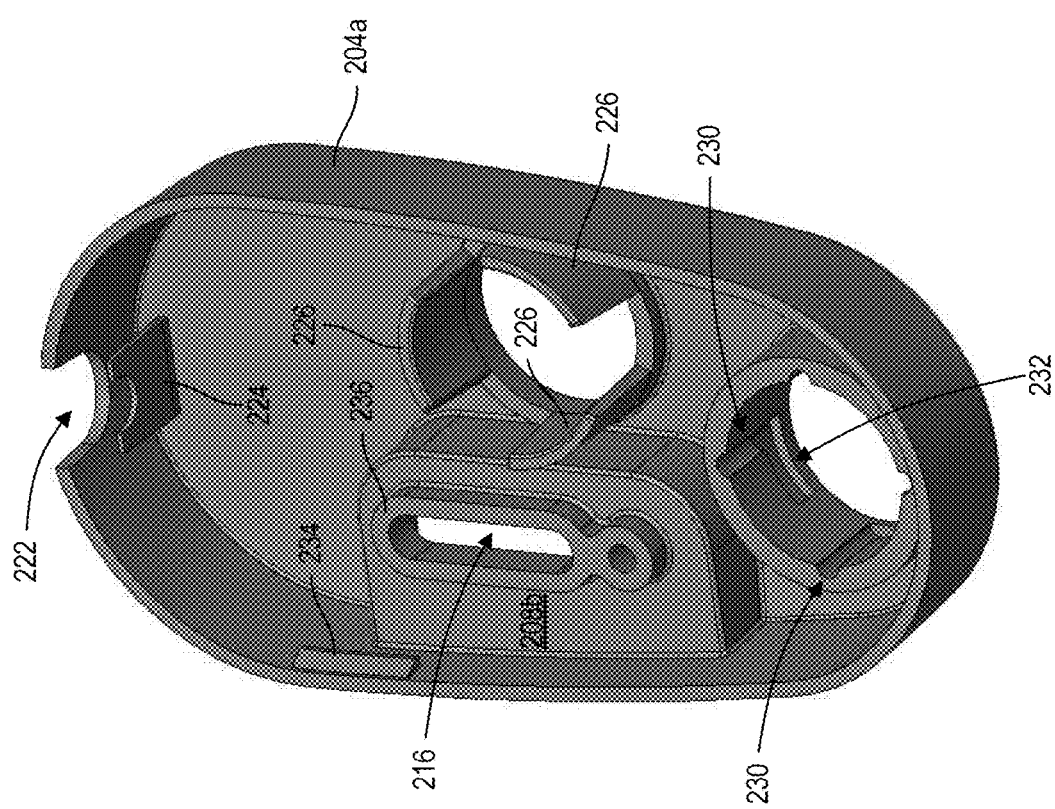
Figure 22A:
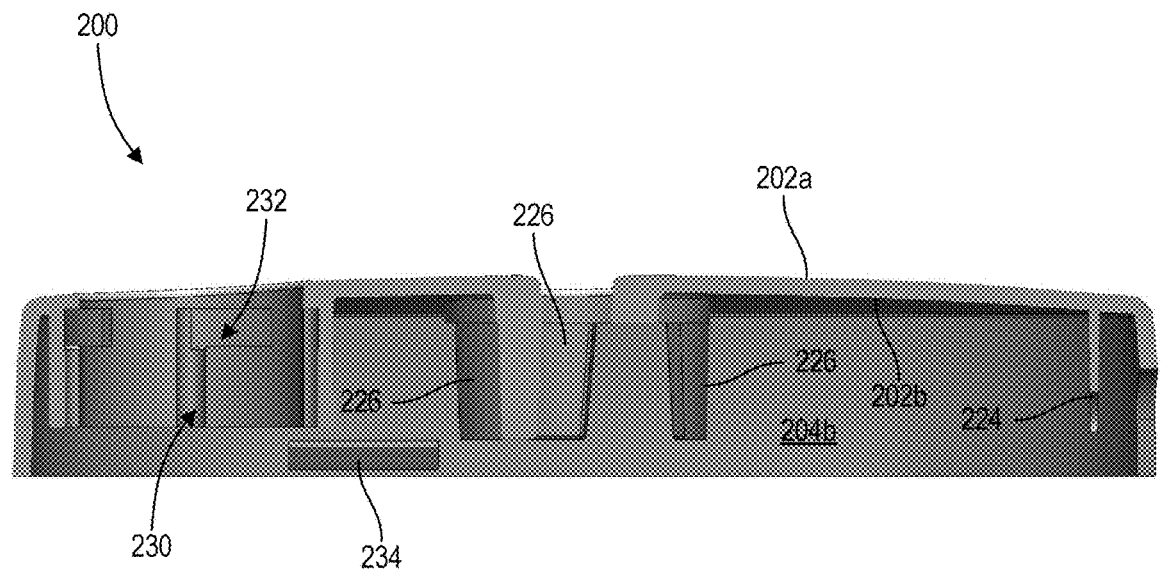
Figure 22B:
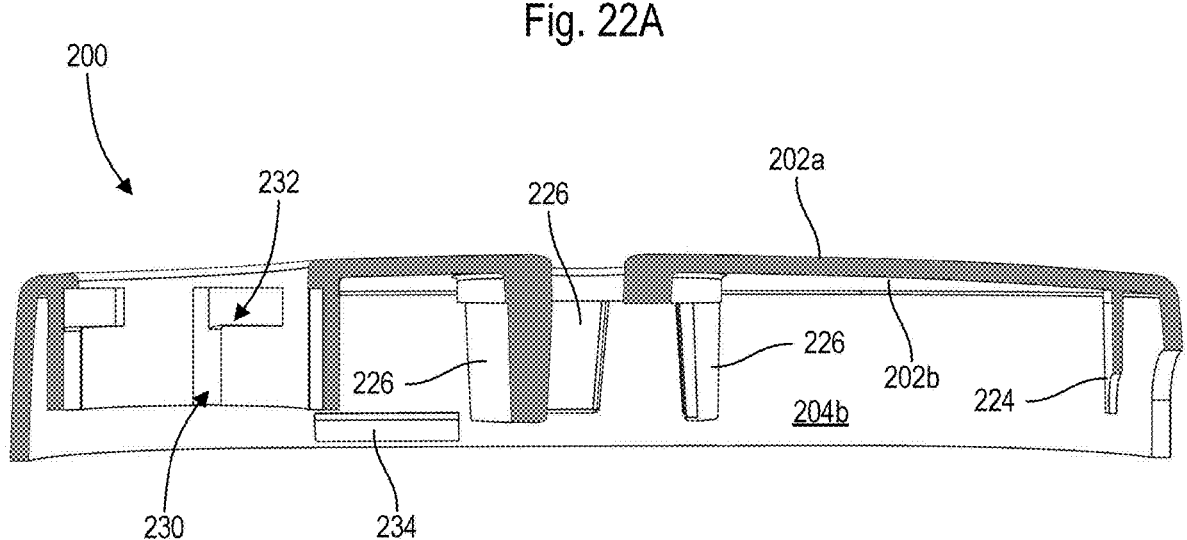

With reference to FIGS. 18A and 18B, the cover 200 further includes a U-shaped locking member 224 and a plurality of projection members 226. The U-shaped locking member 224 is aligned with the U-shaped opening 222. The U-shaped locking member 224 extends vertically from and perpendicular to the inner surface 202*b* of the top wall 202. When the cover 200 is coupled to the base 300, the U-shaped locking member 224 retains the vacuum pin 400 within the base 300 and allows the vacuum pin 400 to move a predetermined distance while remaining within the cartridge 12. The plurality of projection members 226 extend vertically from and perpendicular to the inner surface 202*b* of the top wall 202. The plurality of projection members 226 are disposed around the perimeter of the lancet aperture 210. As will be discussed in further detail herein, the plurality of projection members 226 help secure the cover 200 to the base 300.

The cover 200 also includes a button guide 228 that is generally circular in shape. The button guide 228 extends from and perpendicular to the inner surface 202*b* of the top wall 202. The button guide 228 extends circumferential around the button aperture 212.

The button guide 228 includes a plurality of vertical grooves 230 that extend vertically along an inner surface of the button guide 228 and a plurality of horizontal grooves 232 that extend horizontally along the inner surface of the button guide 228. Each vertical groove 230 is in open communication with a horizontal groove 232 and each vertical groove 230. Furthermore, each vertical groove 230 extends to a proximal end of the button guide 228.

The cover 200 further includes a plurality of locking members 234. The locking members 234 extend vertically from and perpendicular to the inner surface 204b of the side wall 204. As will be discussed in further detail herein, the locking members 234 couple the cover 200 to the base 300. The cover 200 also includes a support structure 236, which extends vertically from and perpendicular to the inner surface 208b of the horizontal wall 208. The support structure 236 extends around the viewing aperture 214 and the test strip viewing aperture 216 in such a manner that the support structure 236 does not prevent a user from viewing components disposed within the cartridge 12 when the cover 200 is coupled to the base 300.

In some embodiments, as depicted in FIGS. 15A, 15B, 16A, and 16B, the cover 200 can include a quick response ("QR") code 22 disposed on the outer surface 202a of the top wall 202. As will be discussed in further detail herein, the QR code 22 can be associated with an electronic medical record ("EMR") stored in an electronic medical record database and may aid in preserving a chain of custody of the cartridge 12.

Referring now to FIGS. 23A and 23B-40A and 40B, the base 300 is shown in accordance with an exemplary embodiment. In this embodiment, the base 300 includes a bottom wall 302 with a top surface 302a, an opposed bottom surface 302b, and an outer surface 302c that extends between the top surface 302a and the bottom surface 302b. The top surface 302a and the bottom surface 302b extend perpendicularly to the outer surface 302c. The outer surface 302c extends perpendicular to and vertically between the top surface 302a and the bottom surface 302b. The bottom wall 302 and the side wall 204 of the cover 200 have the same perimeter shape such that when the cover 200 is coupled to the base 300, outer surface 302c of the base 300 and the outer surface 204a of the cover 200 are flush with one another. Furthermore, when the cover 200 is coupled to the base 300, the side wall 204 contacts the top surface 302a of the bottom wall 302.

The base 300 further includes a rim 304 with an outer surface 304a, an opposed inner surface 304b, and a top surface 304c that extends between the outer surface 304a and the inner surface 304b. The top surface 304c extends perpendicularly to and longitudinally between the outer surface 304a and the inner surface 304b. The outer surface 304a and the inner surface 304b extend vertically from and perpendicular to the top surface 302a of the bottom wall 302 such that the outer surface 304a and the inner surface 304b extend between the top surface 302a and the top surface 304c. The rim 304 is contoured such that when the cover 200 is coupled to the base, at least a portion of the side wall 204 contacts at least a portion of the rim 304. More specifically, at least a portion of the inner surface 204b of the side wall 204 contacts at least a portion of the outer surface 304a of the rim 304.

The base 300 further includes a plurality of extensions 306 that extend vertically from and perpendicular to the rim 304. The extensions 306, the bottom wall 302 and the rim 304 define gaps 308. The gaps 308 and therefore the extensions 306, are shaped to accept a locking member 234 such that an extension 306 couples to a locking member 234 via a snap fitting thereby coupling the cover 200 to the base 300.

The base 300 also includes a vacuum pin receptacle 310 that extends vertically from and perpendicular to the top surface 302a of the bottom wall 302. The vacuum pin receptacle 310 includes an opening 312 and a chamber 314 that are each shaped to accept the vacuum pin 400 such that at least a portion of the vacuum pin 400 may be disposed within the vacuum pin receptacle 310. The vacuum pin receptacle 310 also includes a gap 316 that is shaped and dimensioned to accommodate the arms of the U-shaped locking member 224. That is, when the cover 200 is coupled to the base 300, the arms of the U-shaped locking member 224 extend through and are disposed within the gap 316.

The base 300 also includes a needle aperture 318 that is generally circular in shape. The needle aperture 318 extends through the bottom wall 302. Stated another way, the needle aperture 318 extends between the top surface 302a and the bottom surface 302b of the bottom wall 302. As will be discussed in further detail herein, when the cover 200 is coupled to the base 300 and when the cartridge 12 is adhered to a subject, the needle aperture 318 allows the needle 110 of the lancet 100 to extend through the bottom wall 302 to puncture the subject's skin, thereby allowing extraction of a physiological sample from the subject.

Figure 41:
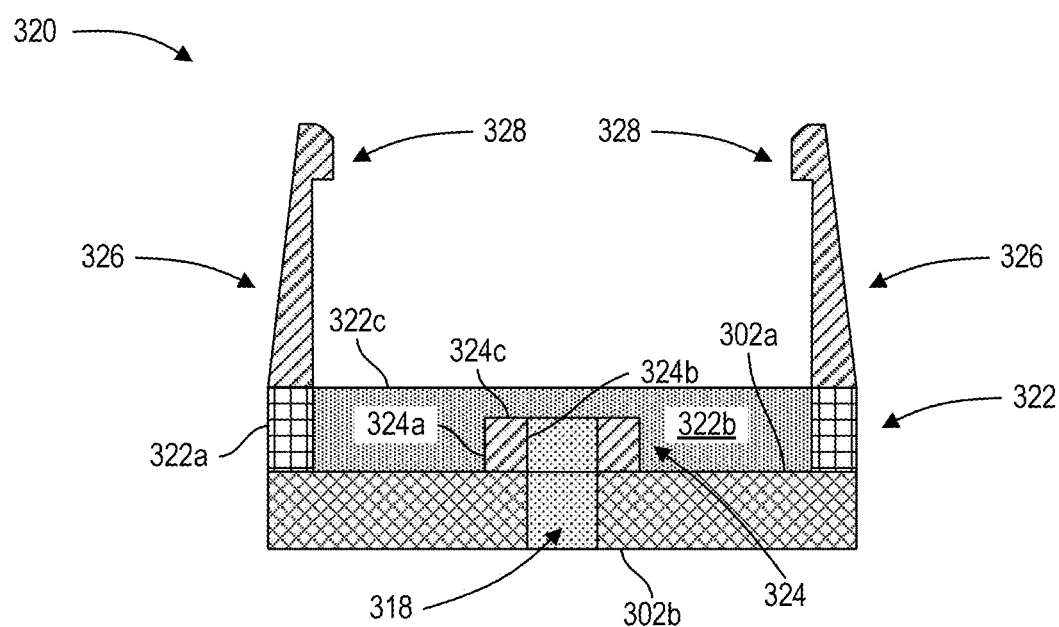
FIG. 41 depicts a lancet receiving element of the base of the dermal patch system in accordance with an exemplary embodiment of the present disclosure.

The base 300 further includes a lancet receiving element 320 that is shaped and dimensioned to accept the distal end of the lancet 100. With particular reference to FIG. 41, the lancet receiving element 320 includes an outer circular projection 322 and an inner circular projection 324 with each extending vertically from and perpendicular to the top surface 302a of the bottom wall 302. The outer circular projection 322 includes an outer surface 322a, an opposed inner surface 322b, and a top surface 322c that extends between the outer surface 322a and the inner surface 322b. The top surface 322c extends perpendicular to and longitudinally between the outer surface 322a and the inner surface 322b. The outer surface 322a and the inner surface 322b extend vertically from and perpendicular to the top surface 302a of the bottom wall 302 such that the outer surface 322a and the inner surface 322b extend between the top surface 302a and the top surface 322c. The outer circular projection 322 is shaped to accept the lancet 100.

The inner circular projection 324 is disposed around the needle aperture 318 and includes an outer surface 324a, an opposed inner surface 324b, and a top surface 324c that extends between the outer surface 324a and the inner surface 324b. The top surface 324c extends perpendicular to and longitudinally between the outer surface 324a and the inner surface 324b. The outer surface 324a and the inner surface 324b extend vertically from and perpendicular to the top surface 302a of the bottom wall 302 such that the outer surface 324a and the inner surface 324b extend between the top surface 302a and the top surface 324c. Furthermore, the outer circular projection 322 and the inner circular projection 324 circular projection are concentric with one another. As will be discussed in further detail herein, when the lancet 100 is engaged with the base 300, the top surface 324c of the inner circular projection contacts a portion of the lancet 100 which allows the lancet 100 to release the needle 110 so as to puncture the skin, thereby allowing the extraction of a physiological sample from the subject's skin.

Figure 23A:
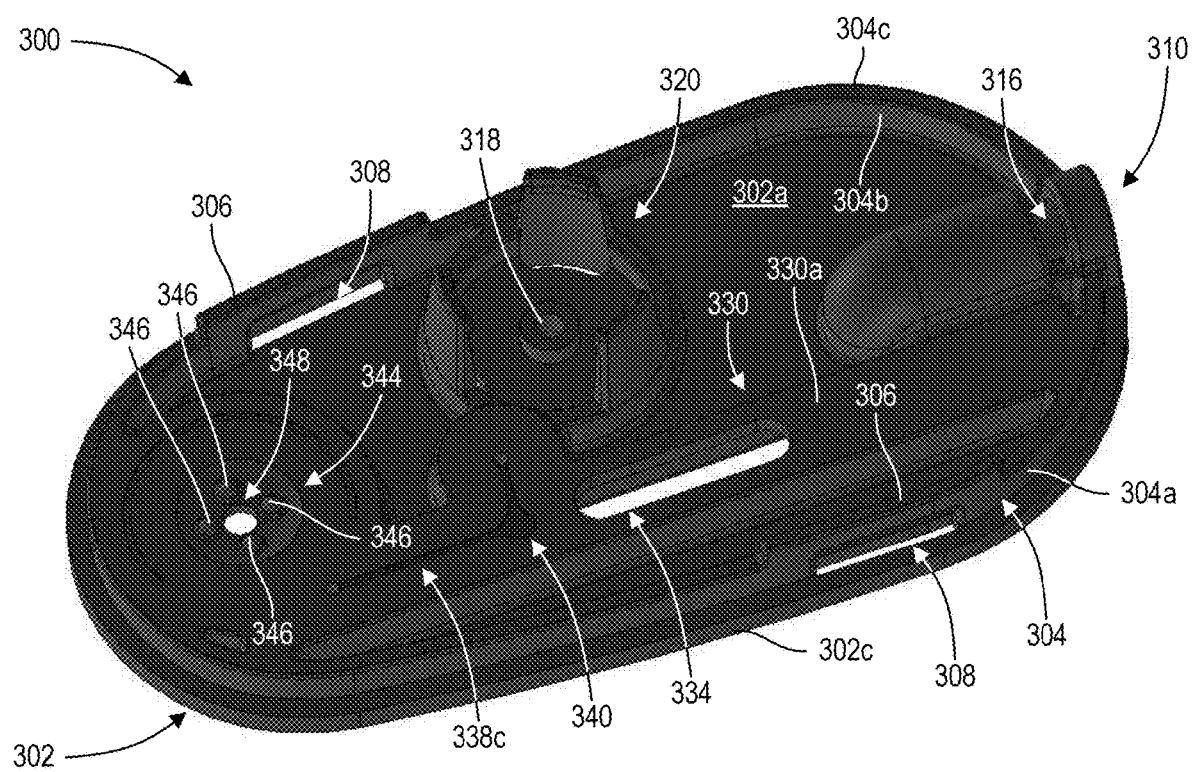
Figure 23B:
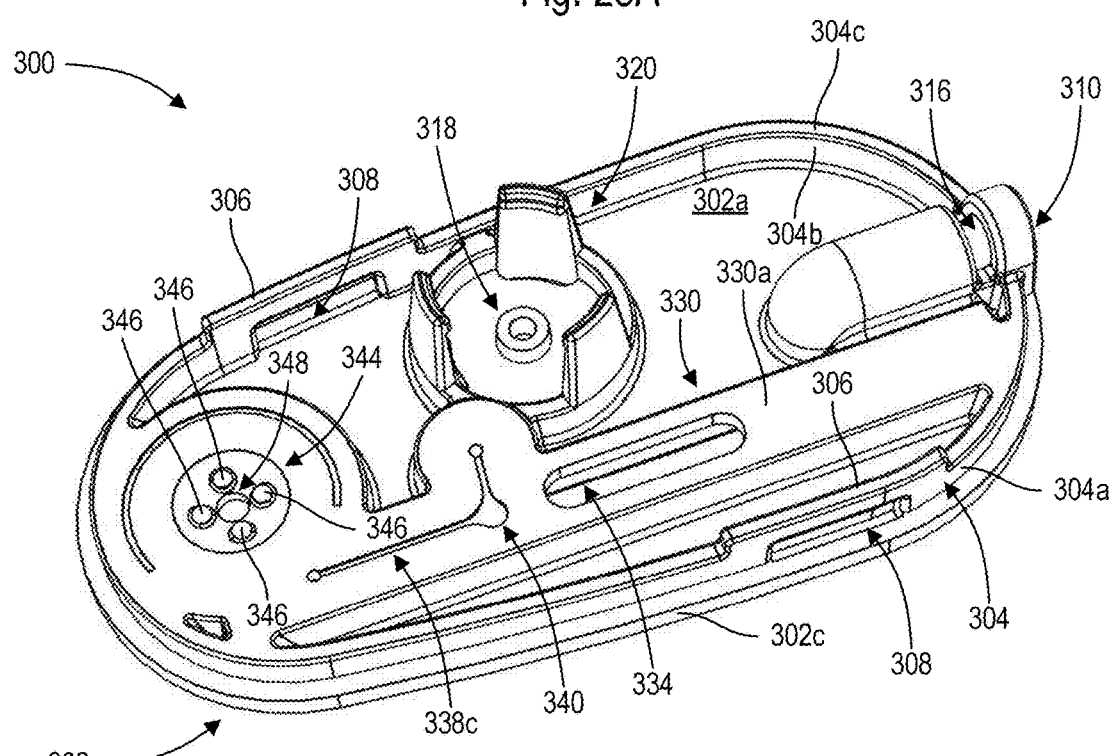
Figure 24A:
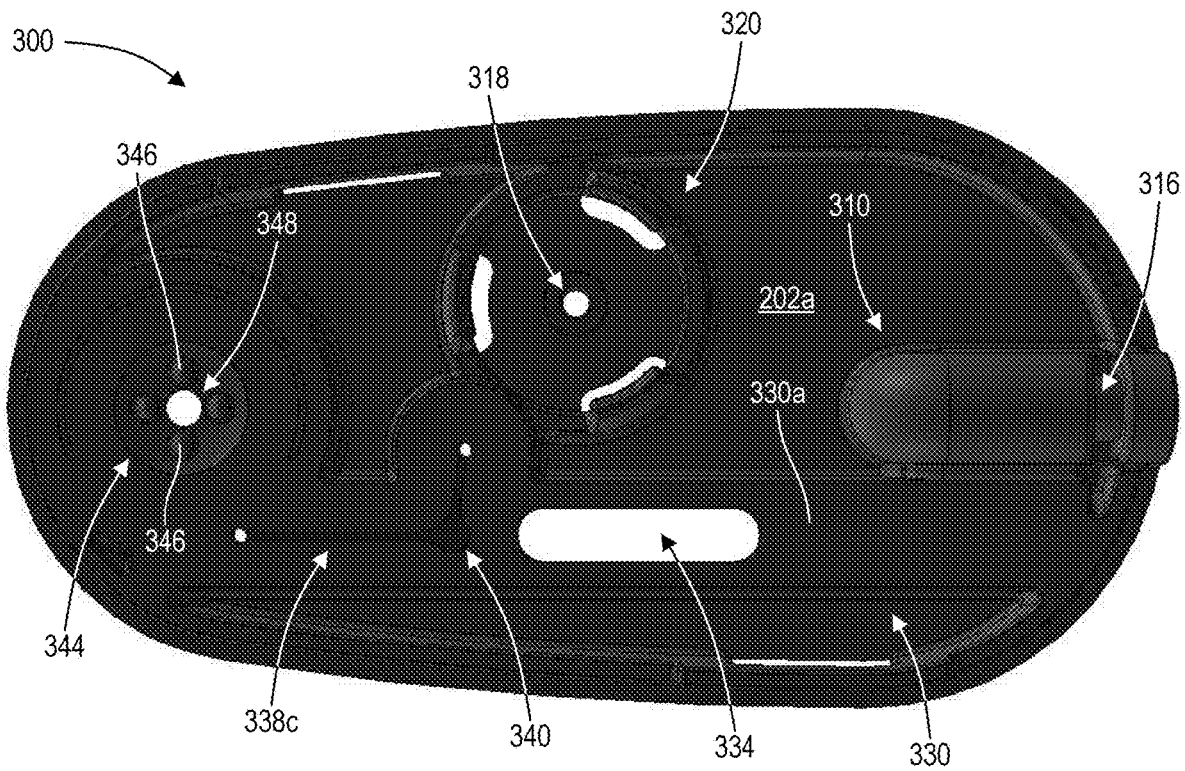
Figure 24B:
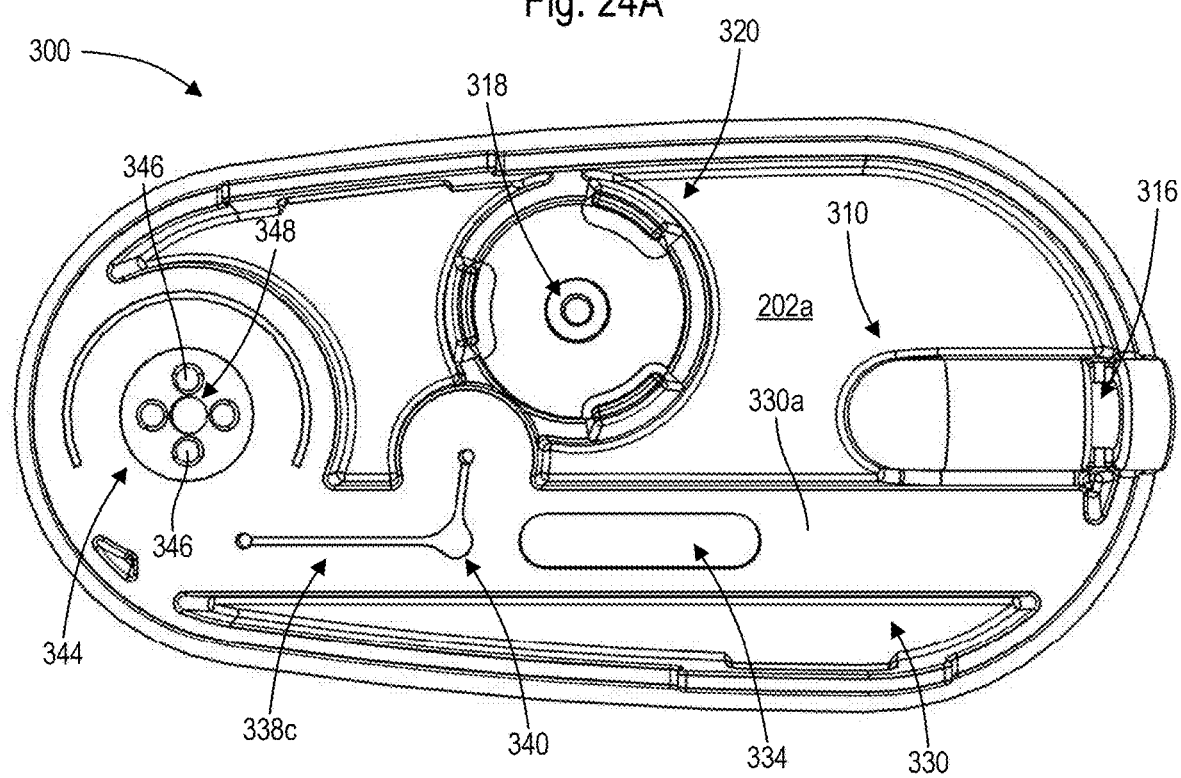
Figures 25A, 25B:
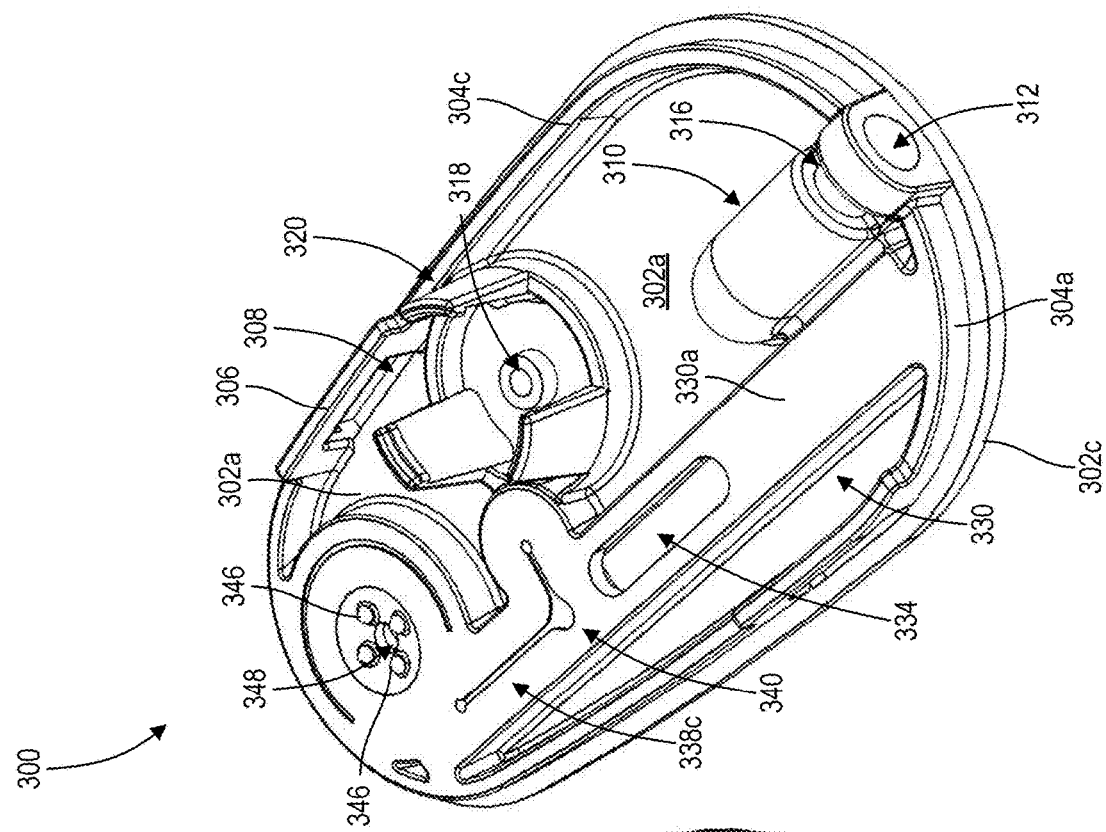
Figure 26A:
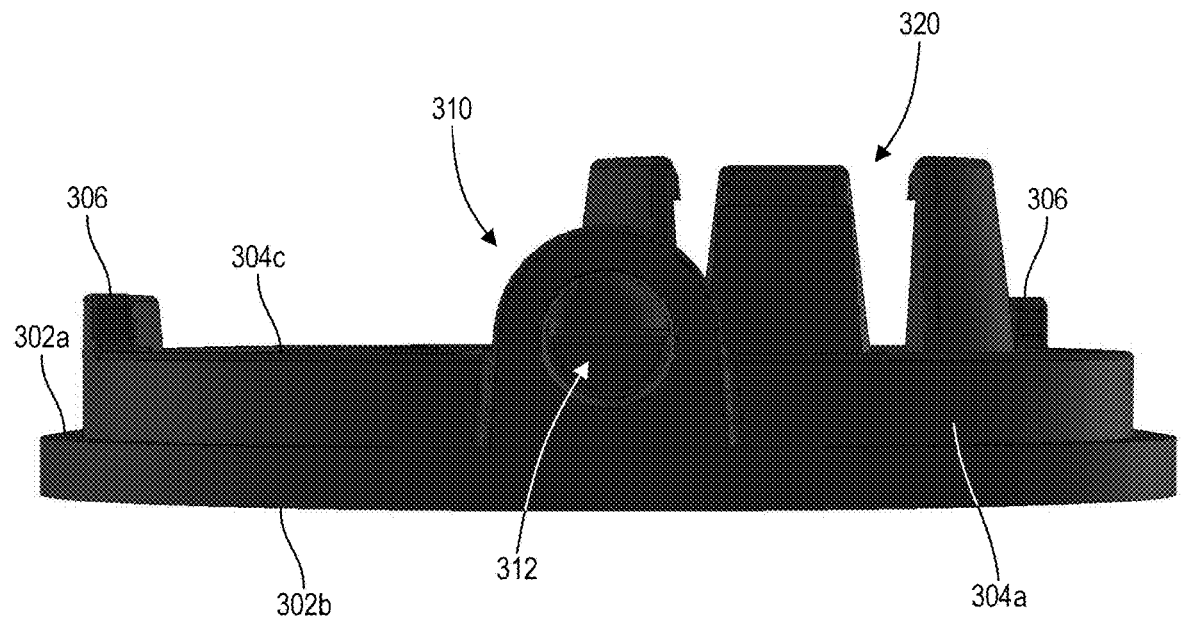
Figure 26B:
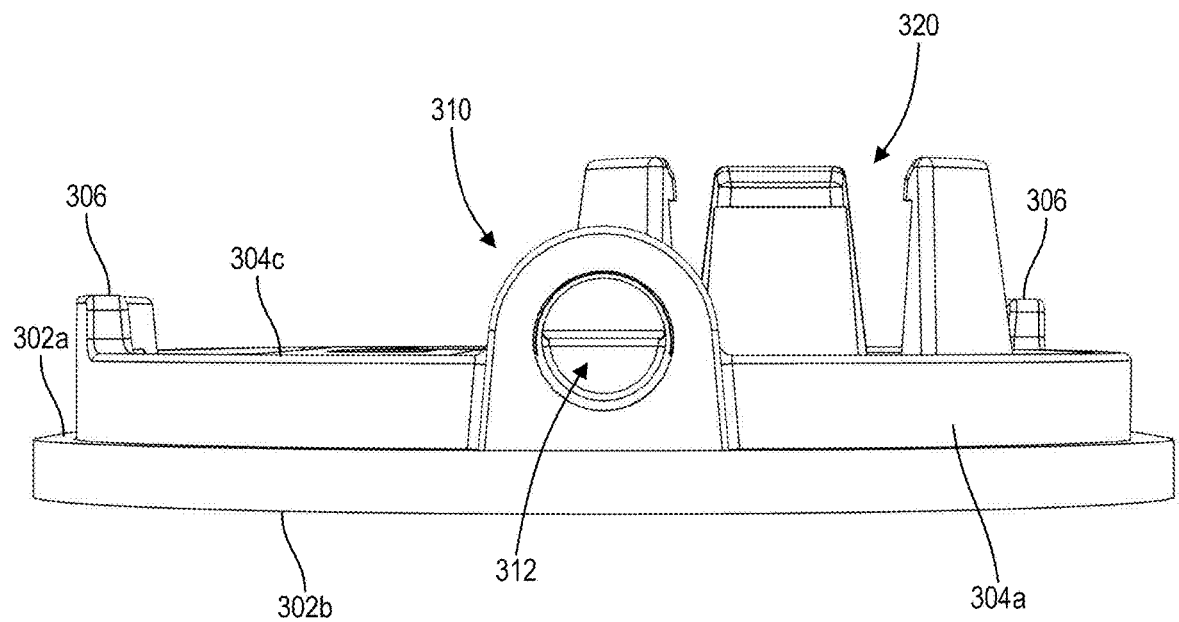
Figure 29A:
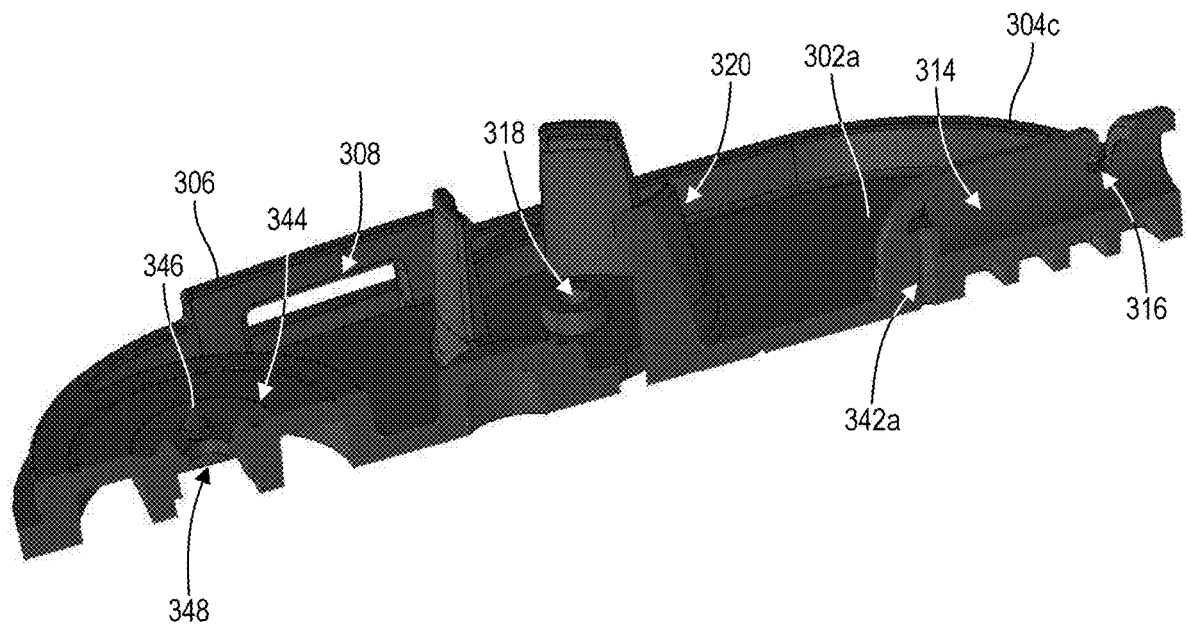
Figure 29B:
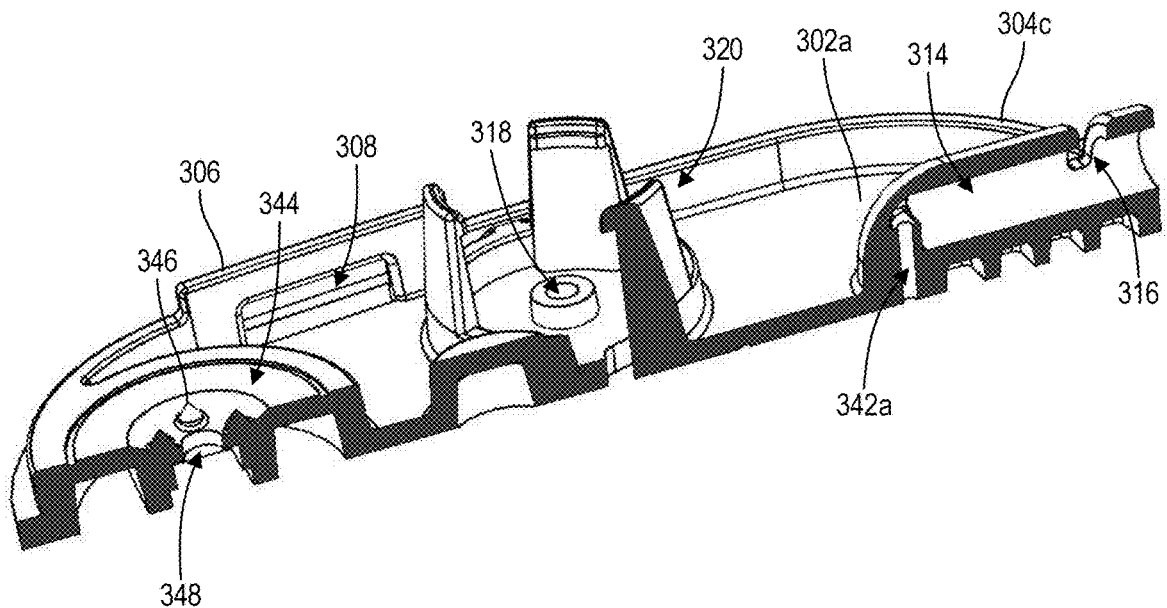
Figure 30A:
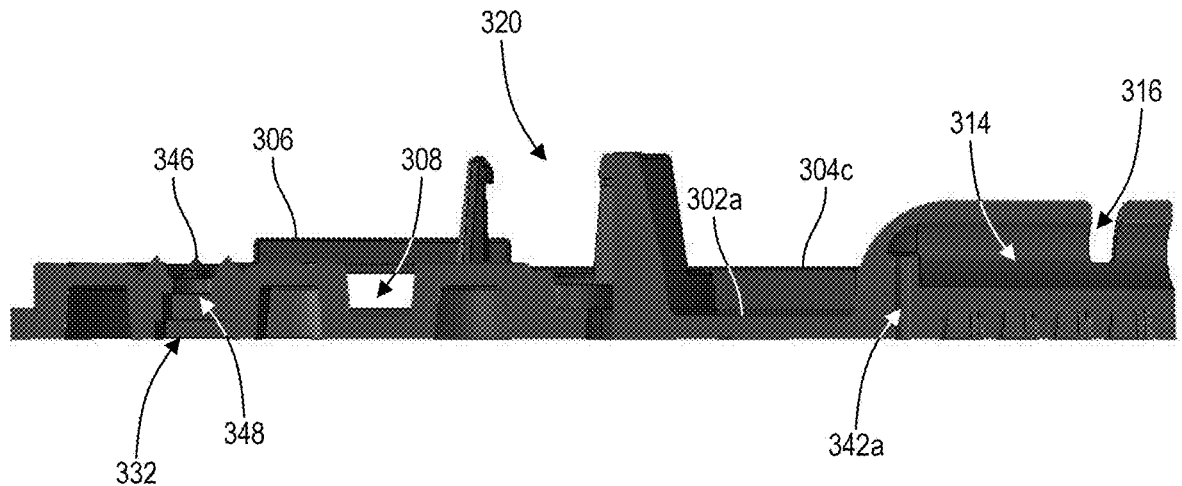
Figure 30B:
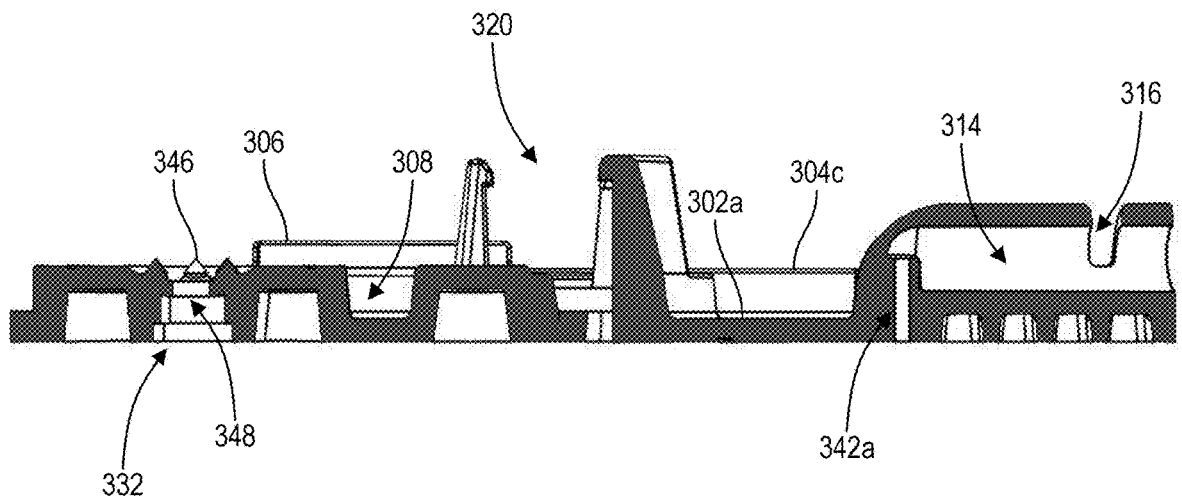
Figure 31A:
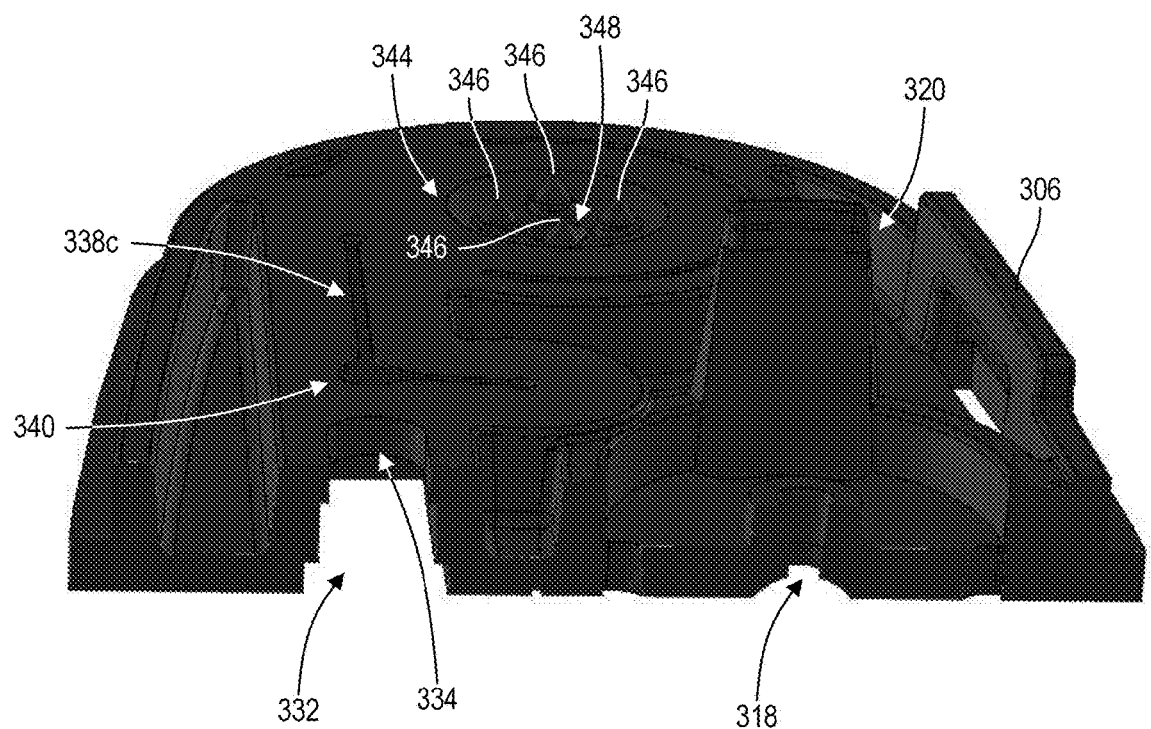
Figure 31B:
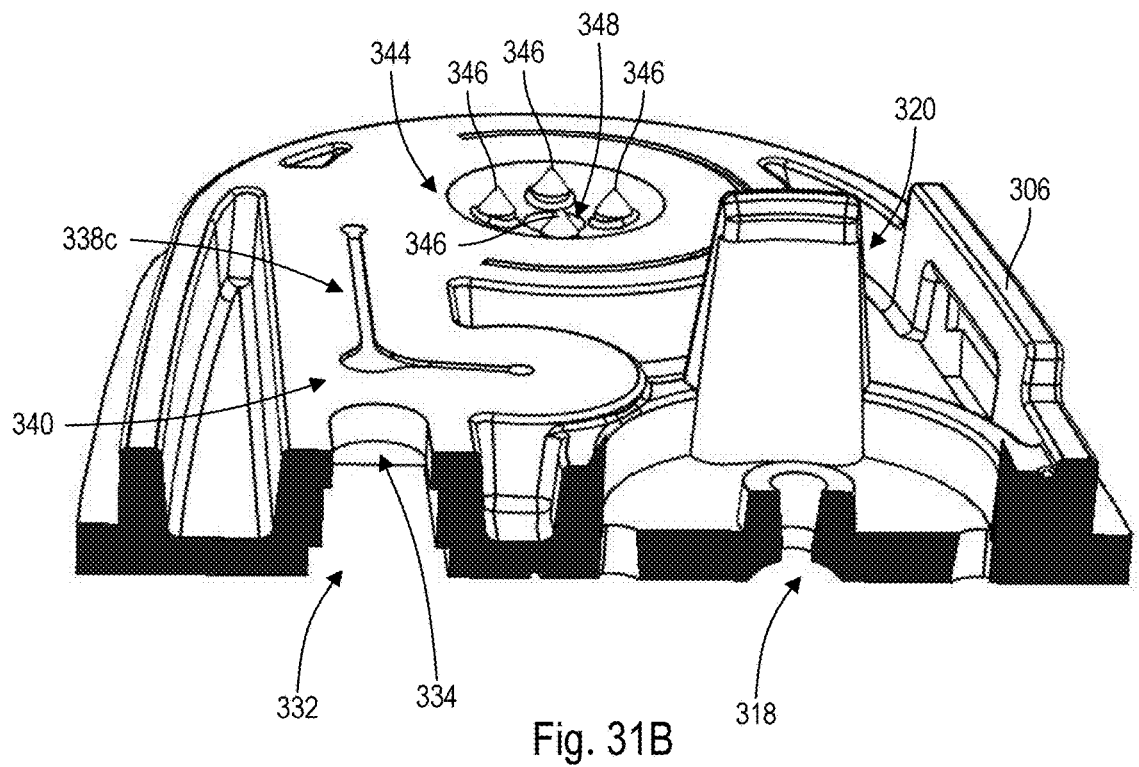
Figure 32A:
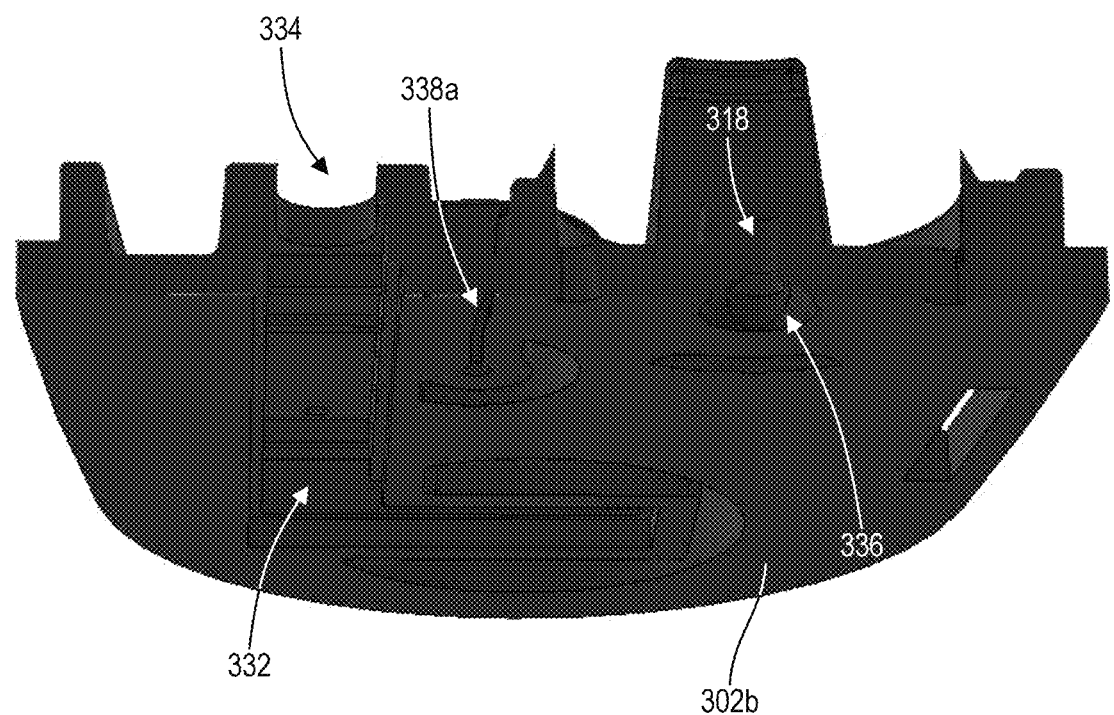
Figure 32B:
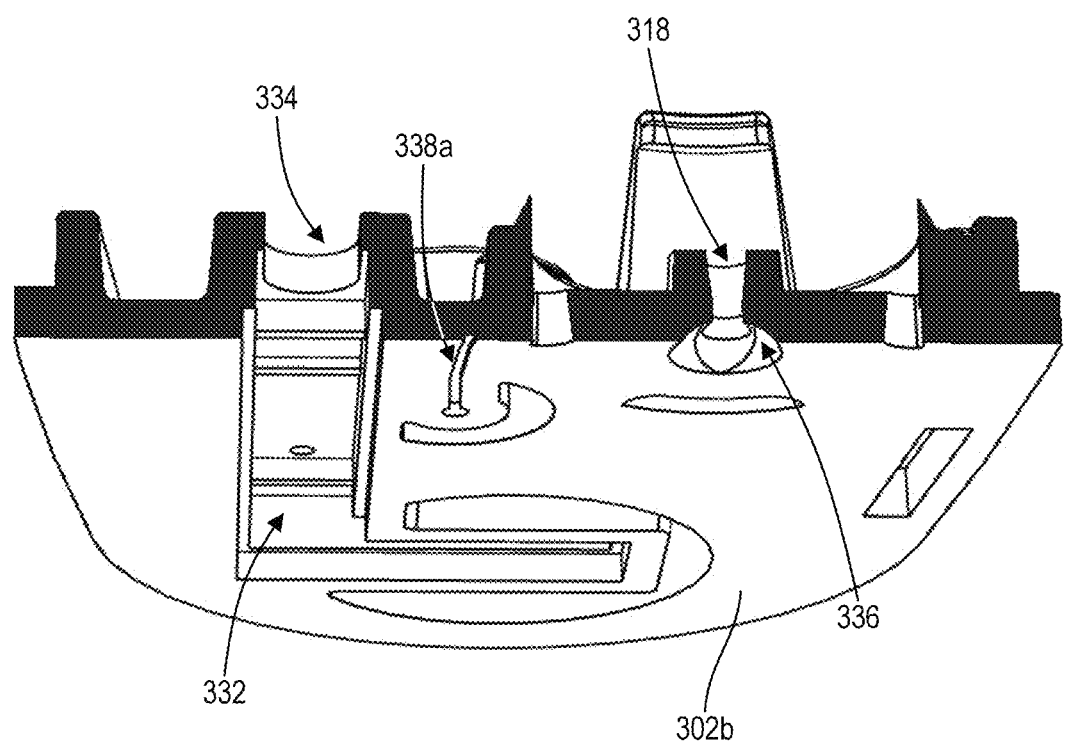
Figure 33A:
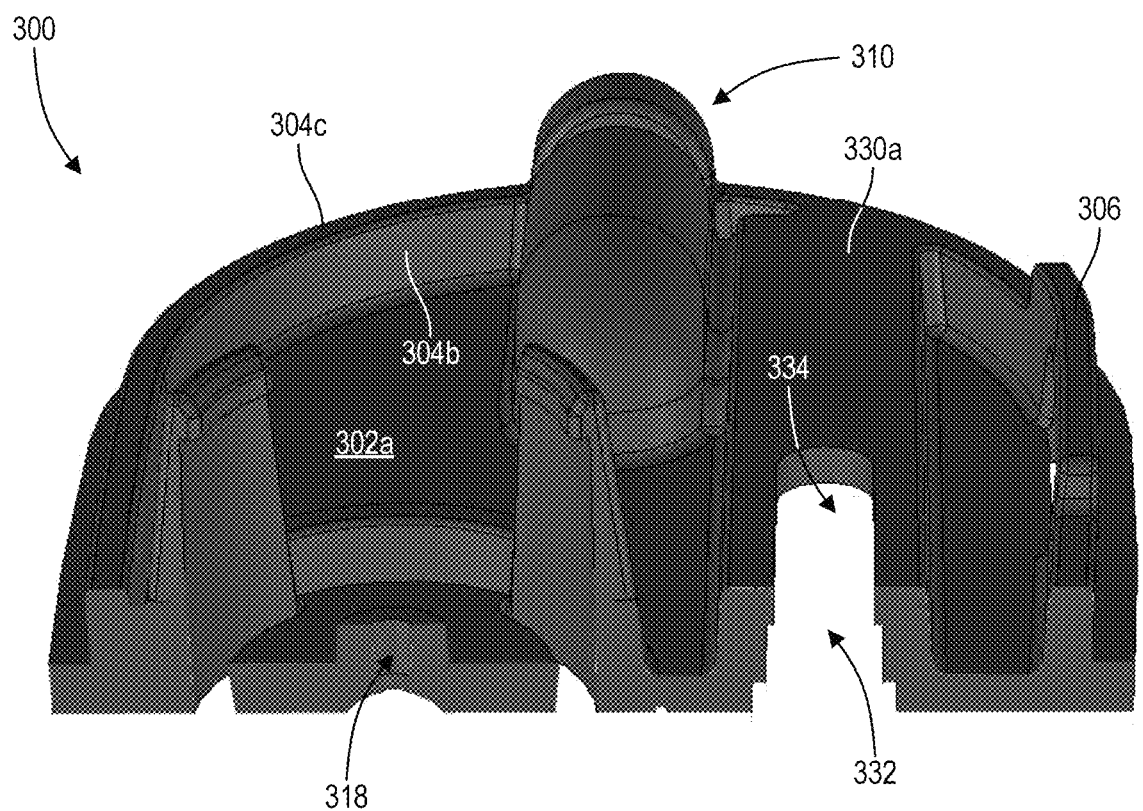
Figure 33B:
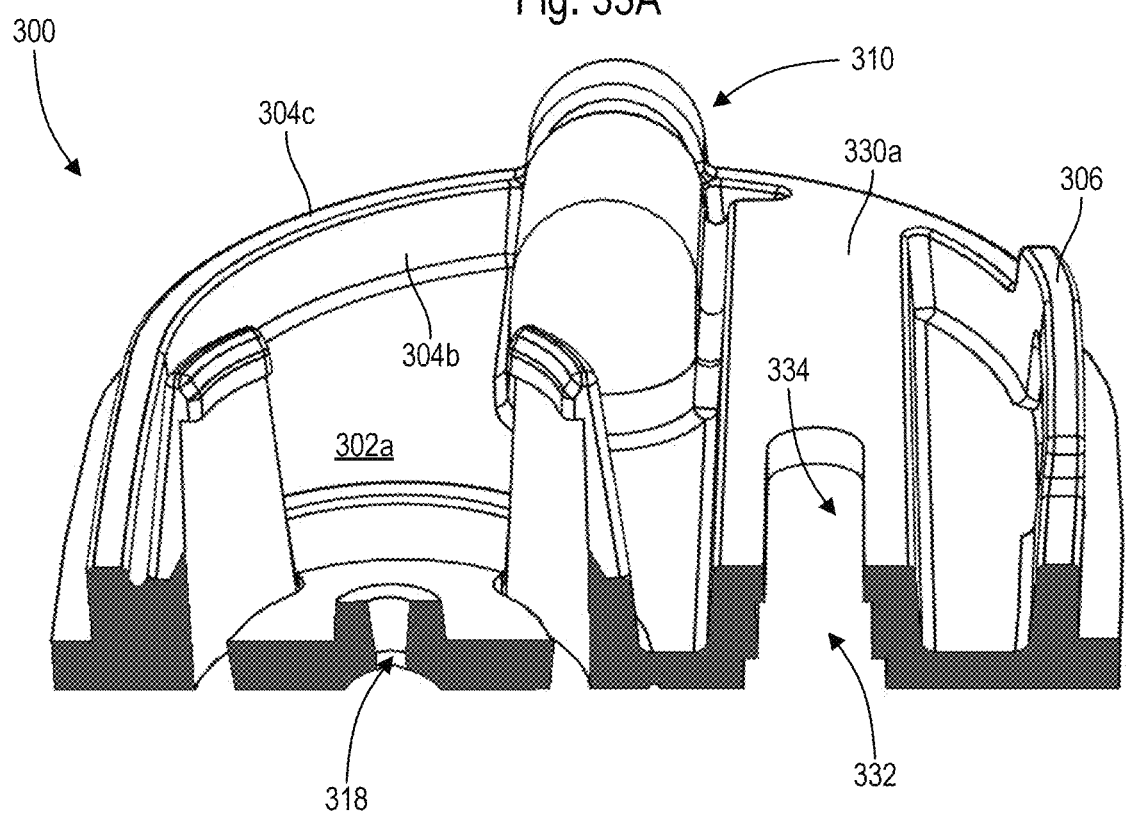
Figure 34A:
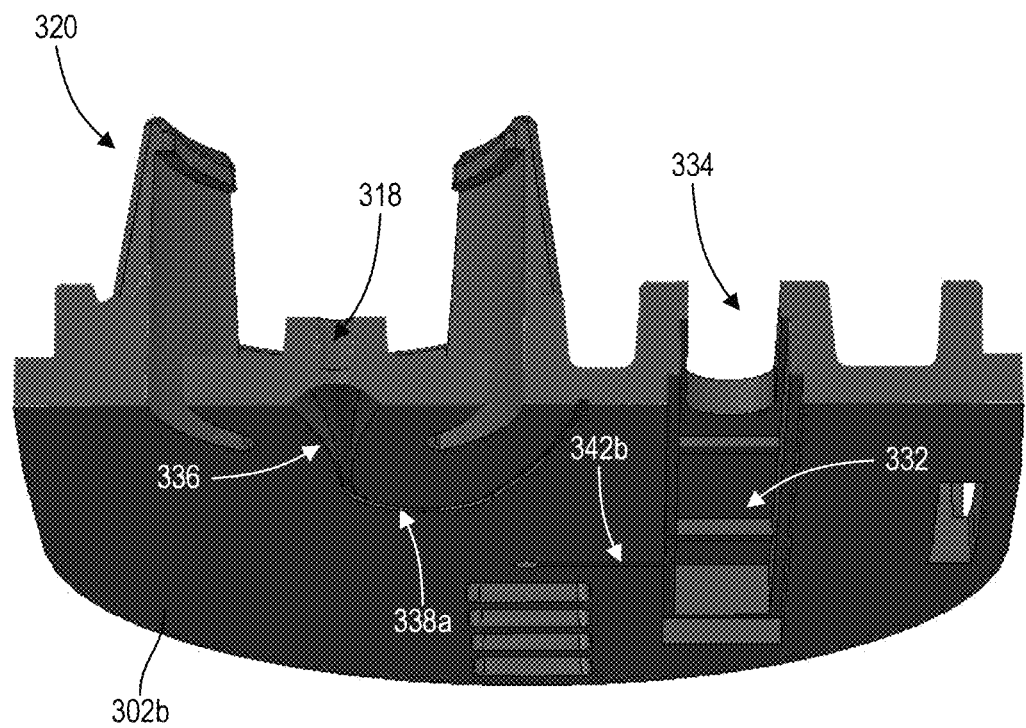
Figure 34B:
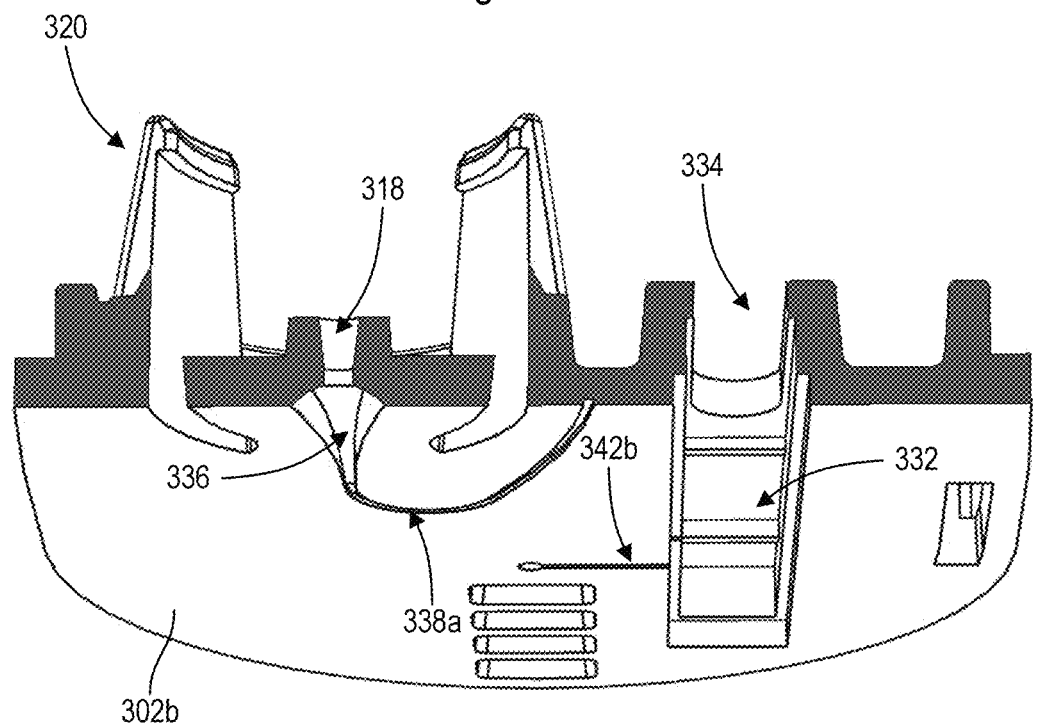
Figure 35A:
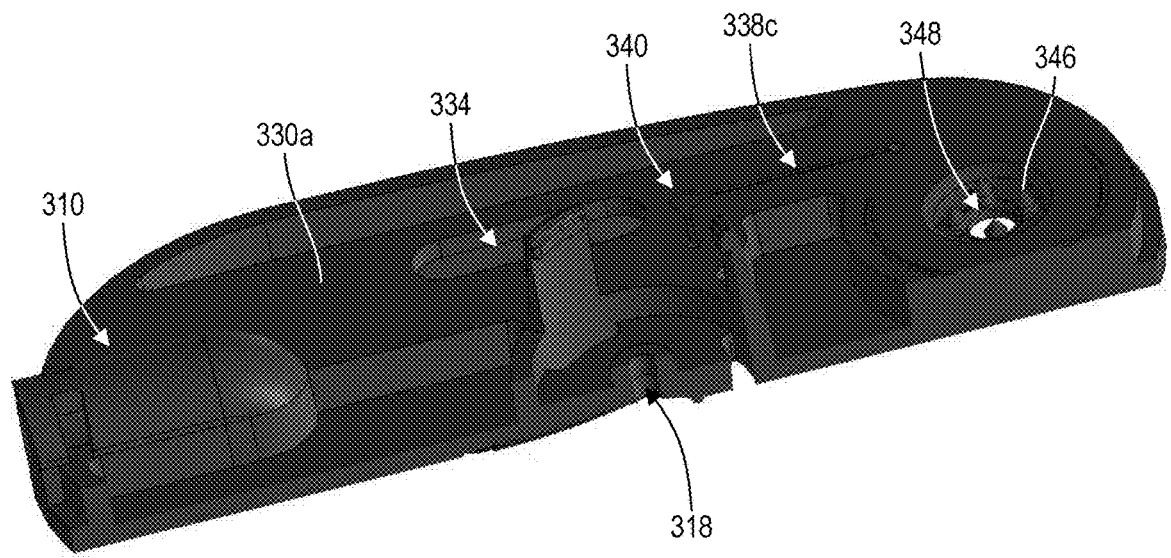
Figure 35B:
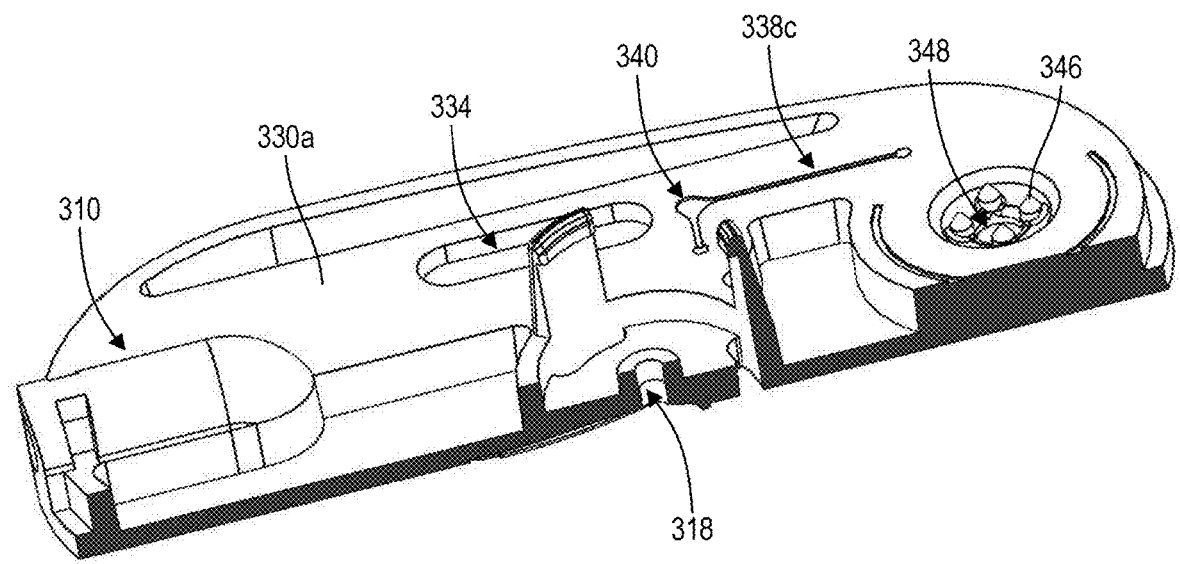
Figure 36A:
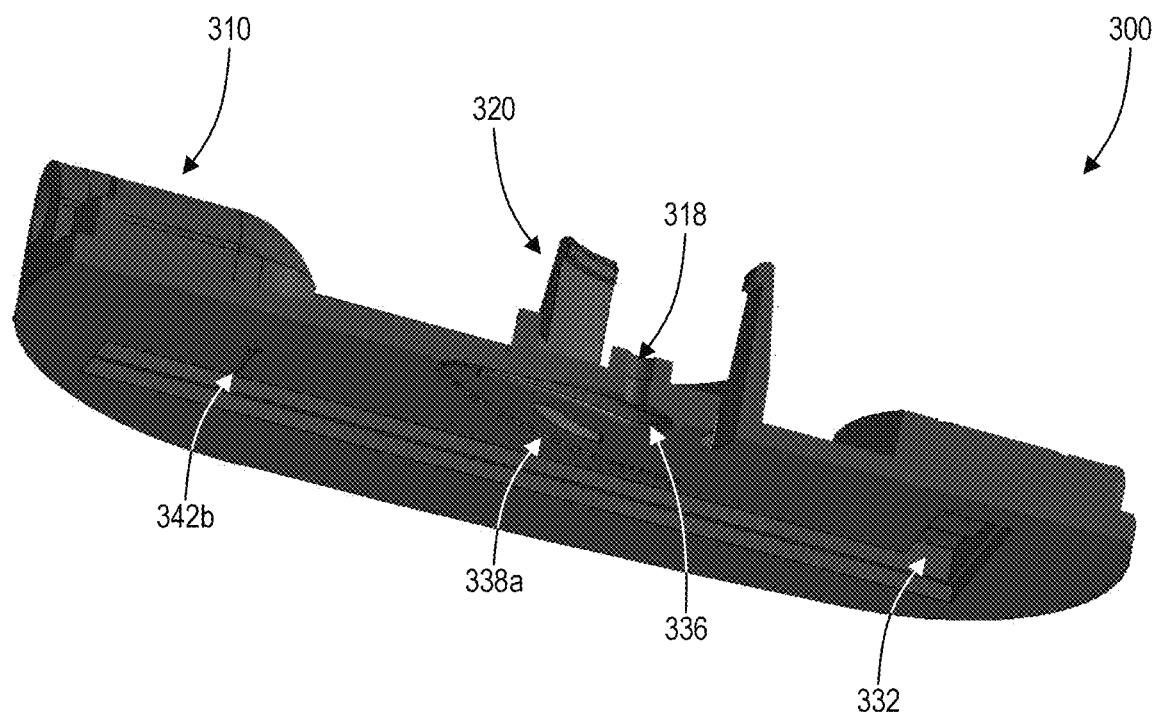
Figure 36B:
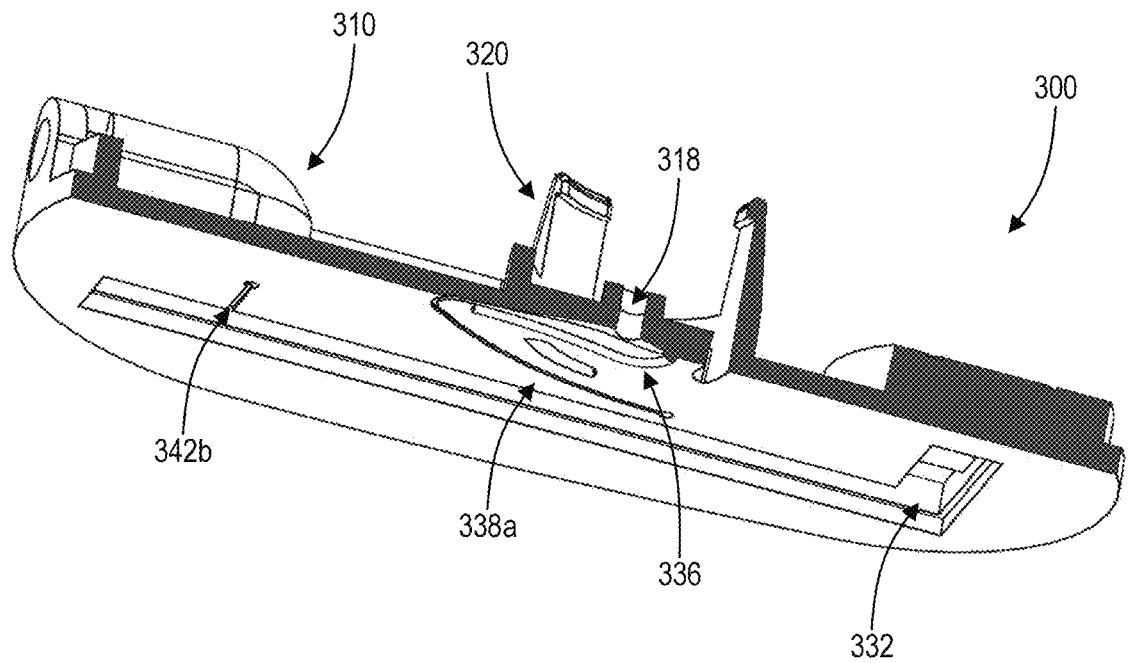
Figure 37A:
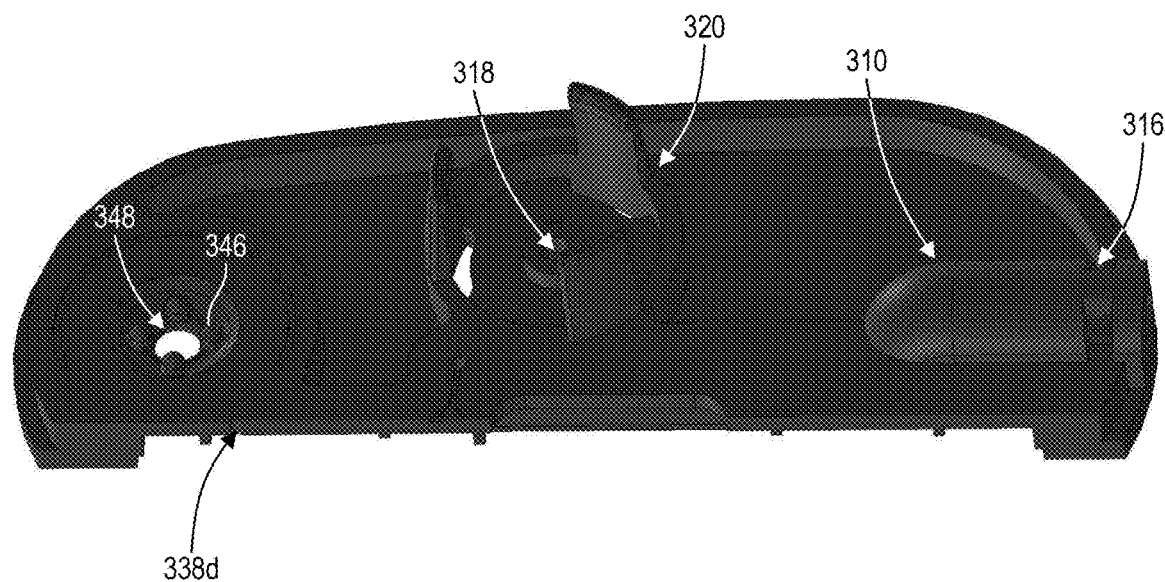
Figure 37B:
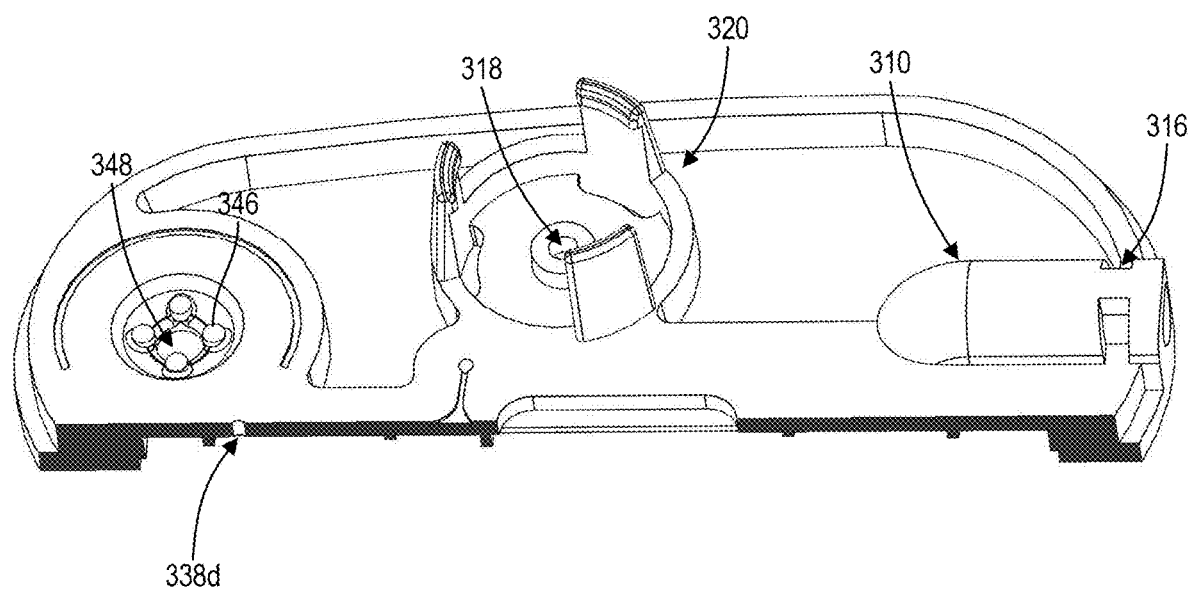
Figure 38A:
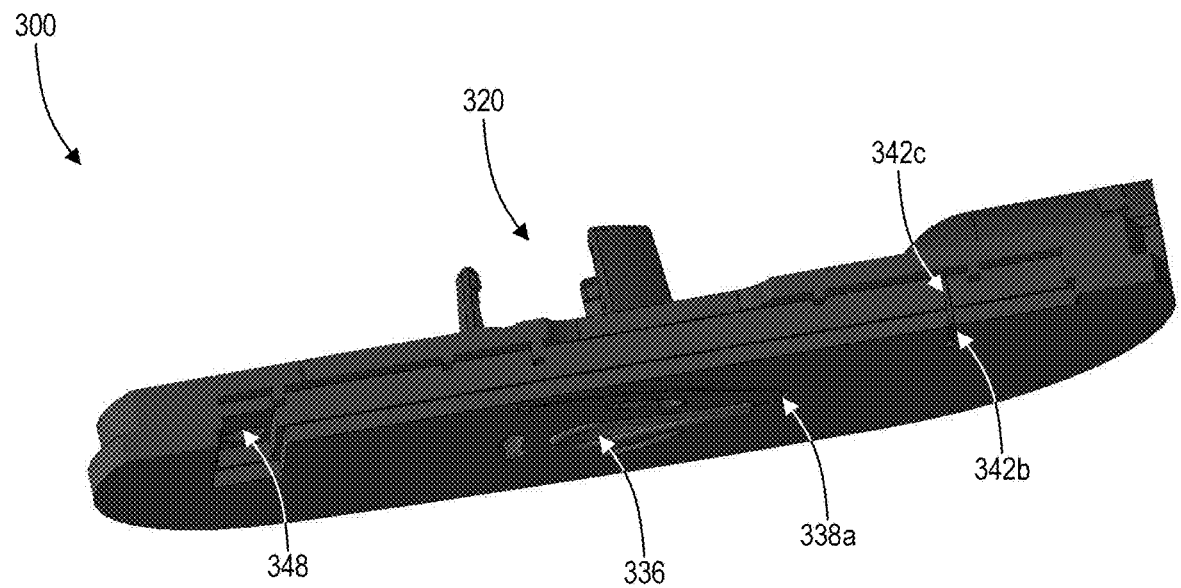
Figure 38B:
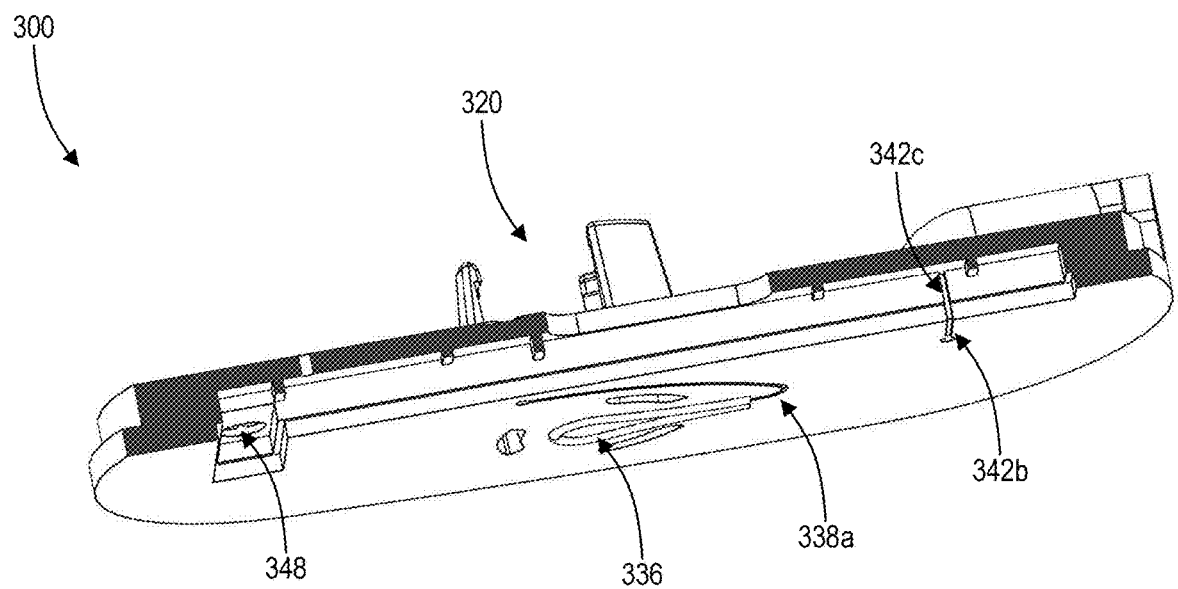
Figure 39A:
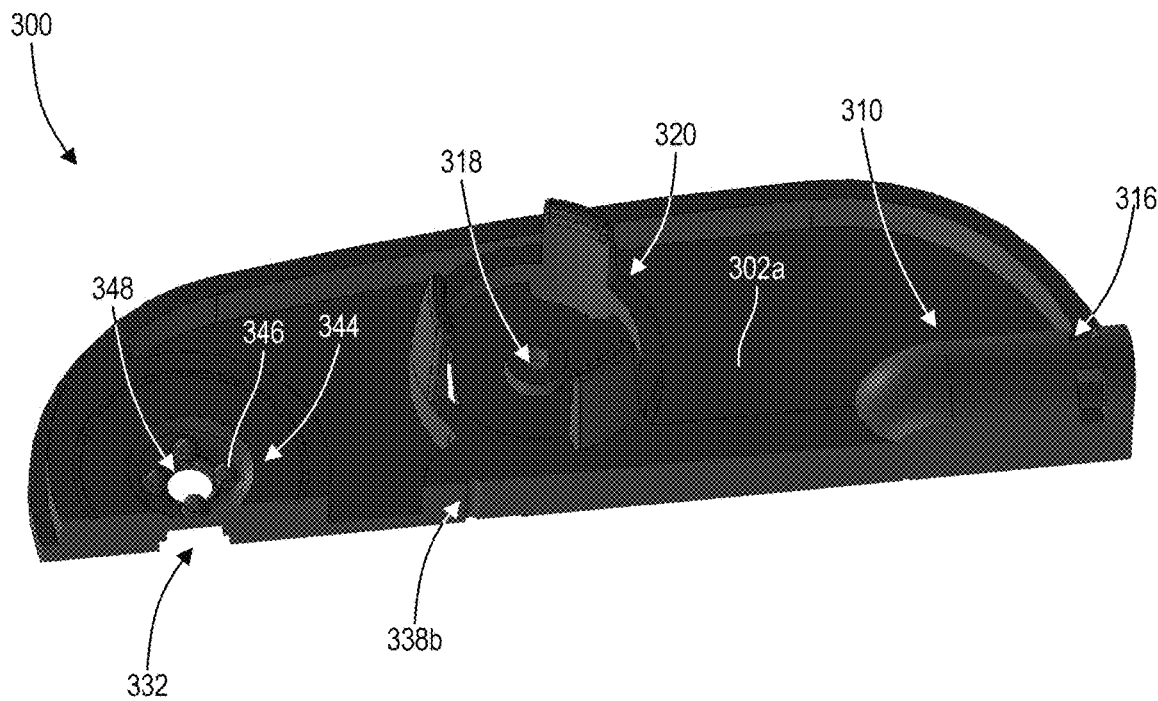
Figure 39B:
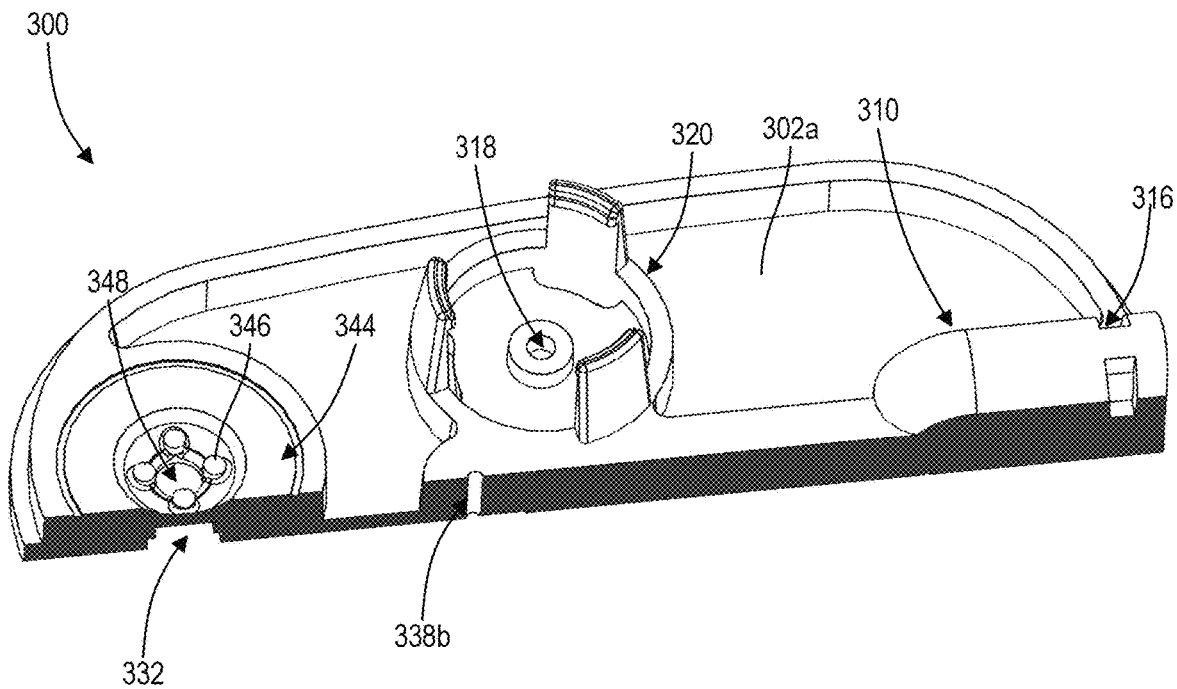
Figure 40A:
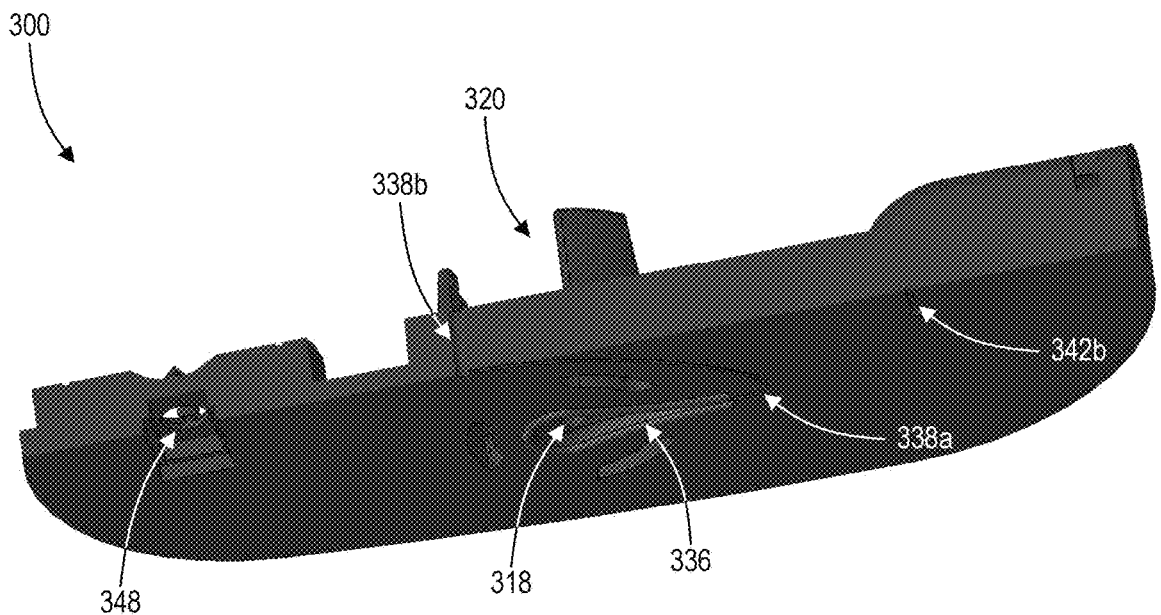
Figure 40B:
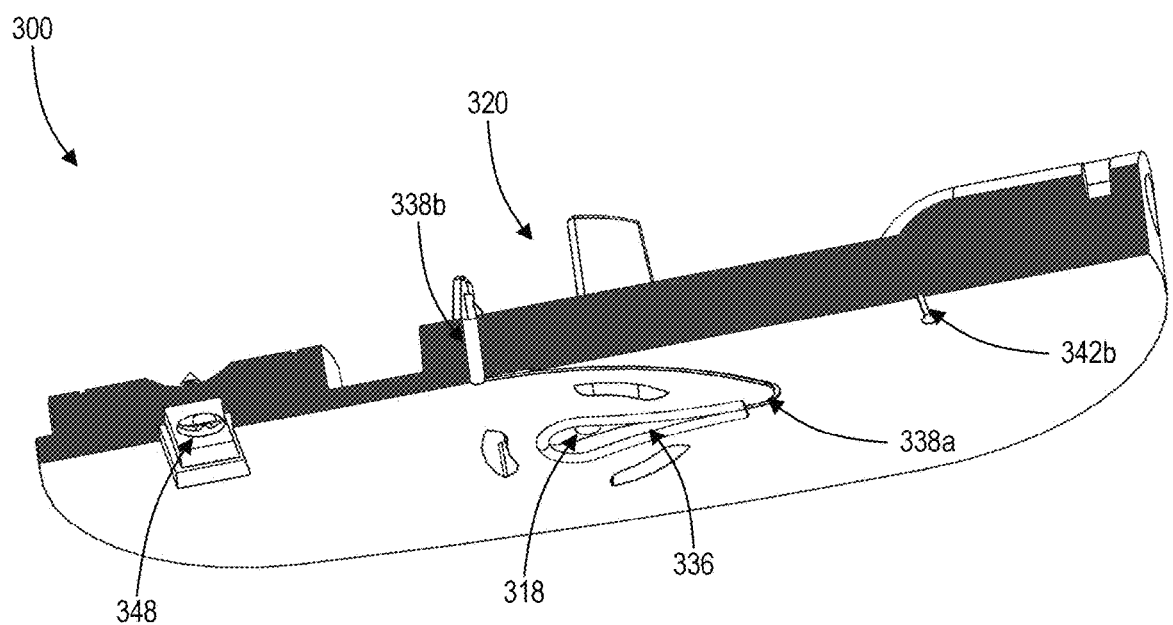

With continued reference to FIGS. 23A and 23B, the base 300 further includes a plurality of locking members 326

(FIG. 41) that extend vertically from and perpendicular to the top surface 322c of the outer circular projection 322. For the sake of clarity, one of the locking members 326 is not shown in FIGS. 23A and 23B. Each locking member 326 includes a hook 328 (FIG. 41) that extends inwardly from a top of a locking member 326 towards the inner circular projection 324. As will be discussed in further detail herein, the hooks 328 of the locking members 326 couple to the lancet 100 to retain the lancet 100 within the base 300. The locking members 326 are equally spaced around the outer circular projection 322 thereby defining a gap between the locking members 326. When the cover 200 is coupled to the base 300, the projection members 226 extend between the locking members 326 in these gaps thereby coupling the cover 200 to the base 300.

The base 300 includes a diagnostic test strip housing 330. The diagnostic test strip housing 330 extends vertically from and perpendicular to the top surface 302a and includes an outer surface 330a an opposed inner surface 330b and a vertical surface 330c. The vertical surface 330c extends perpendicular to and vertically between the inner surface 330b and the bottom surface 302b. The inner surface 330b and vertical surface 330c define an inner volume 332 of the diagnostic test strip housing 330. The diagnostic test strip housing 330 further includes an opening 334 that extends between the outer surface 330a and the inner surface 330b. When the cover 200 is coupled to the base 300 the opening 334 is positioned vertically below the test strip viewing aperture 216.

The base 300 further includes a physiological sample well 336 and a physiological sample channel 338 with a first portion 338a, a second portion 338b, a third portion 338c, and a fourth portion 338d.

The first portion 338a extends from the physiological sample well 336. As will be discussed in further detail herein, the physiological sample channel 338 is a fluidic channel that is configured to carry a physiological sample extracted from a subject. The physiological sample well 336 and the first portion 338a of the physiological sample channel 338 are open with respect to the bottom surface 302b of the bottom wall 302. Stated another way, the physiological sample well 336 and the first portion 338a of the physiological sample channel 338 do not include a bottom surface. The physiological sample well 336 is in open communication with the needle aperture 318. As will be discussed in further detail herein, when drawing a physiological sample, a needle of the lancet 100 extends through the needle aperture 318 and through the physiological sample well 336 to pierce the skin of the subject.

The second portion 338b of the physiological sample channel 338 extends vertically from and perpendicular to the first portion 338a. The second portion 338b extends through the bottom wall 302 and the diagnostic test strip housing 330. That is, the second portion 338b extends between the bottom surface 302b of the bottom wall 302 and the outer surface 330a of the diagnostic test strip housing 330.

The third portion 338c extends longitudinally from and perpendicular to the second portion 338b. The third portion 338c extends along the outer surface 330a of the diagnostic test strip housing 330. The third portion 338c of the physiological sample channel 338 is open with respect to the outer surface 330a of the diagnostic test strip housing 330. Stated another way, the third portion 338c of the physiological sample channel 338 does not include a top surface. The third portion 338c includes a reservoir 340. When the cover 200 is coupled to the base 300, the reservoir 340 is disposed below the sample viewing aperture 214 which allows a user of the dermal patch system 10 to view a drawn physiological sample within the reservoir 340.

The fourth portion 338d of the physiological sample channel 338 extends vertically from and perpendicular to the third portion 338c. The fourth portion 338d extends between outer surface 330a and the inner surface 330b of the diagnostic test strip housing 330 such that the physiological sample channel 338 is in open communication with the inner volume 332.

The base 300 further includes a vacuum channel 342 that is in fluid communication with the chamber 314 of the vacuum pin receptacle 310. A first portion 342a of the vacuum channel 342 extends from the chamber 314 and extends vertically within the base 300. A second portion 342b of the vacuum channel 342 extends longitudinally from and perpendicular to the first portion 342a of the vacuum channel 342 such that the second portion 342b of the vacuum channel 342 extends along the bottom surface 302b of the bottom wall 302. Similar to the physiological sample well 336 and the first portion 338a of the physiological sample channel 338, the second portion 342b of the vacuum channel 342 is open with respect to the bottom surface 302b of the bottom wall 302. The vacuum channel 342 further includes a third portion 342c that extends vertically from and perpendicular to the second portion 342b. The third portion 342c extends vertically along the vertical surface 330c of the diagnostic test strip housing 330. The vacuum channel 342 is in open communication with the inner volume 332 of the diagnostic test strip housing 330. As such, the vacuum channel 342 is in open communication with the physiological sample well 336 via the inner volume 332 and the physiological sample channel 338.

The base 300 further includes a depression 344 and a plurality of piercing elements 346 that extend vertically from the depression 344. The base 300 also includes a buffer aperture 348 that extends between the depression 344 and the inner surface 330b.

Figure 8A:
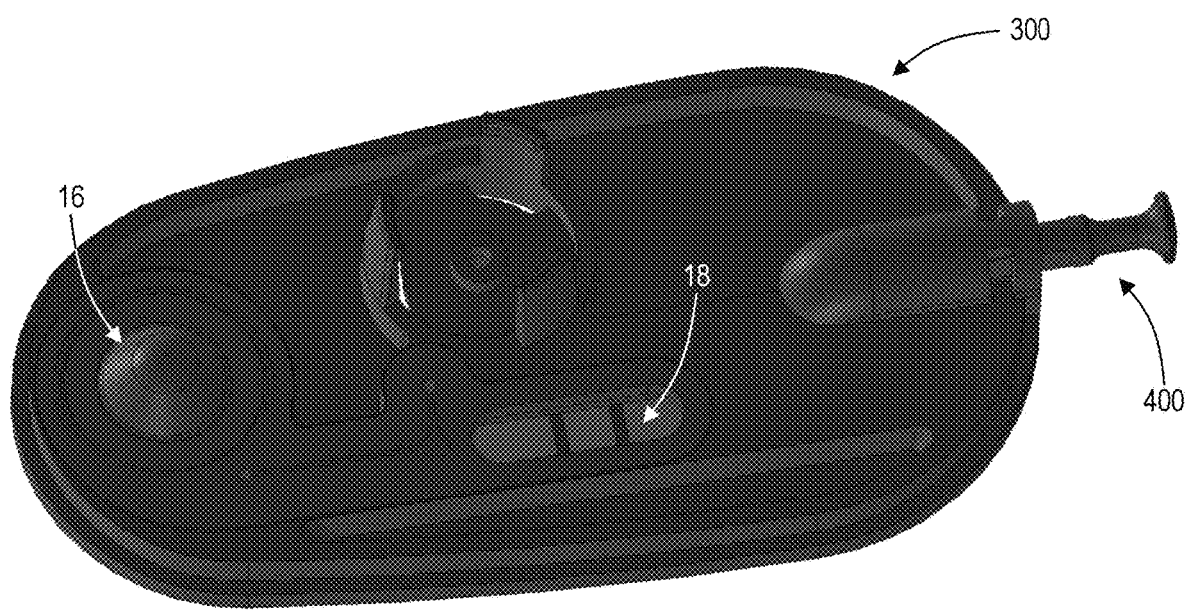
FIGS. 8A and 8B depict a base of the cartridge that includes a processing fluid pack and a diagnostic test strip in accordance with an exemplary embodiment of the present disclosure.
Figure 8B:
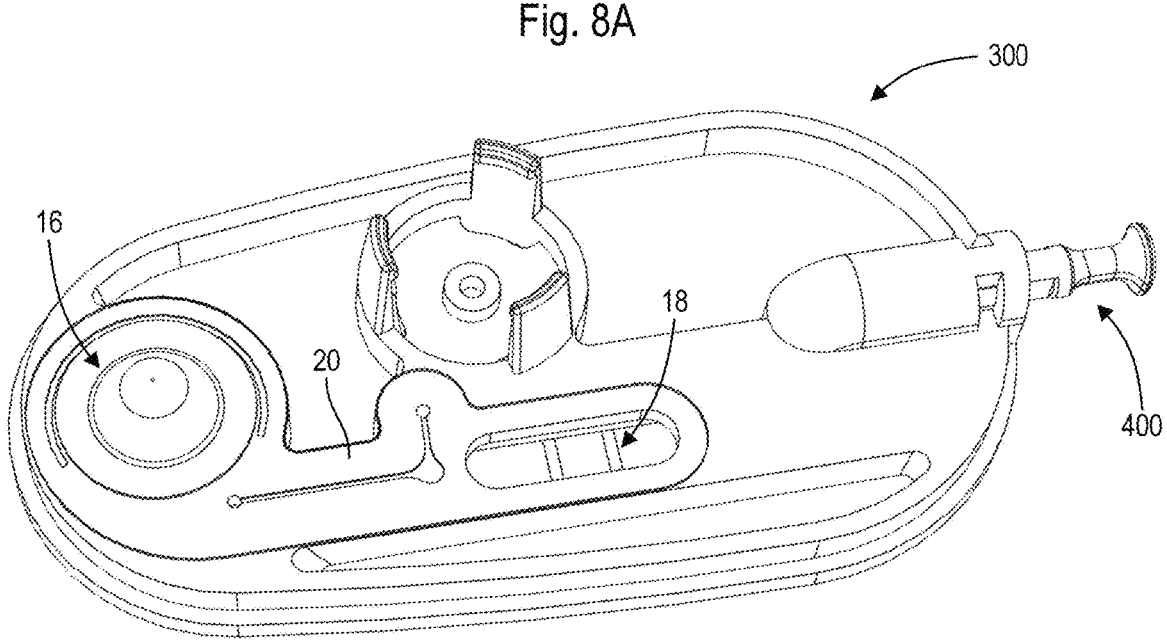

As previously discussed herein, the first portion 338a and the third portion 338c of the physiological sample channel 338 are open. As depicted in FIGS. 4A and 4B, the adhesive layer 14 is disposed on the bottom surface 302b of the bottom wall 302 thereby sealing the first portion 338a of the physiological sample channel 338. Furthermore, as depicted in FIGS. 8A and 8B, the film 20 is disposed on the outer surface 330a of the diagnostic test strip housing 330 thereby sealing the third portion 338c of the physiological sample channel 338.

Figure 42A:
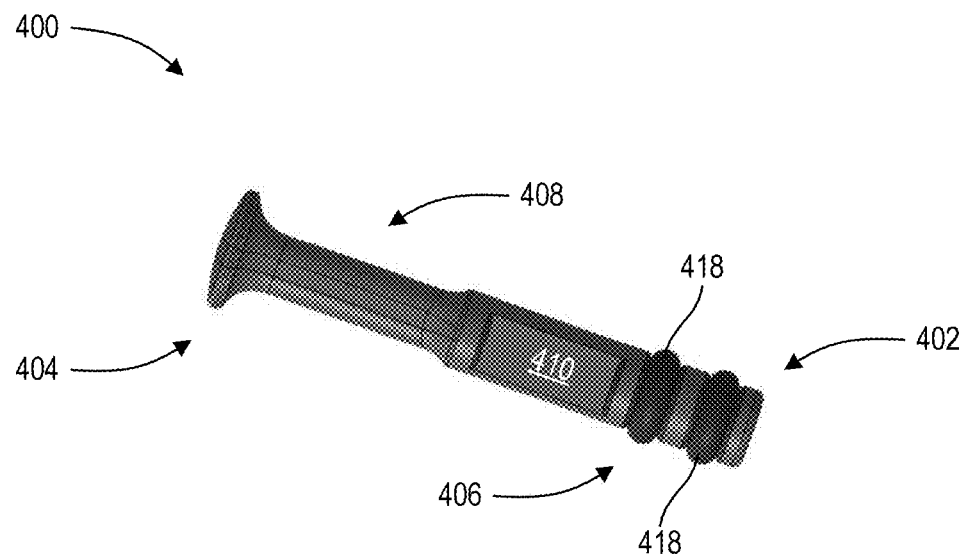
FIGS. 42A and 42B depict a vacuum pin of the dermal patch system in accordance with an exemplary embodiment of the present disclosure.
Figure 42B:
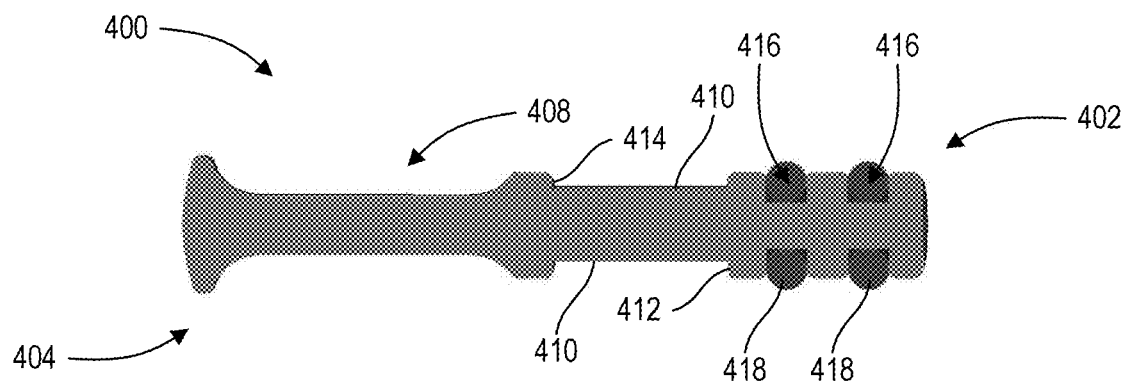
Figure 43A:
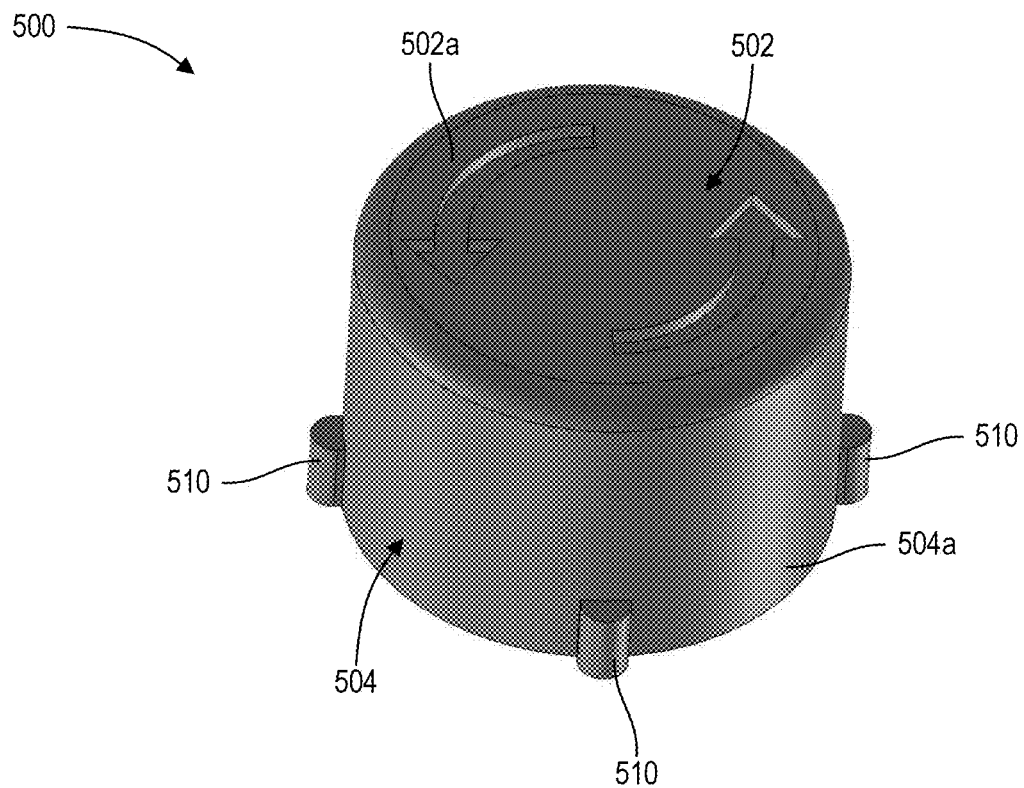
Figure 43B:
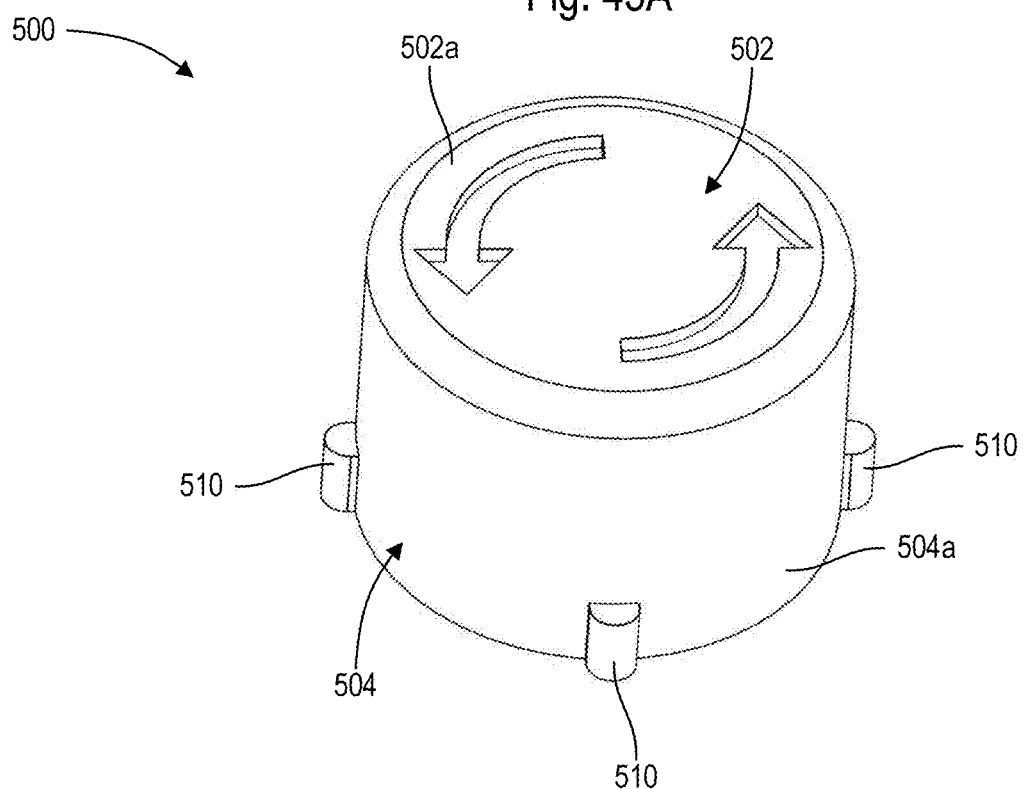
Figure 44A:
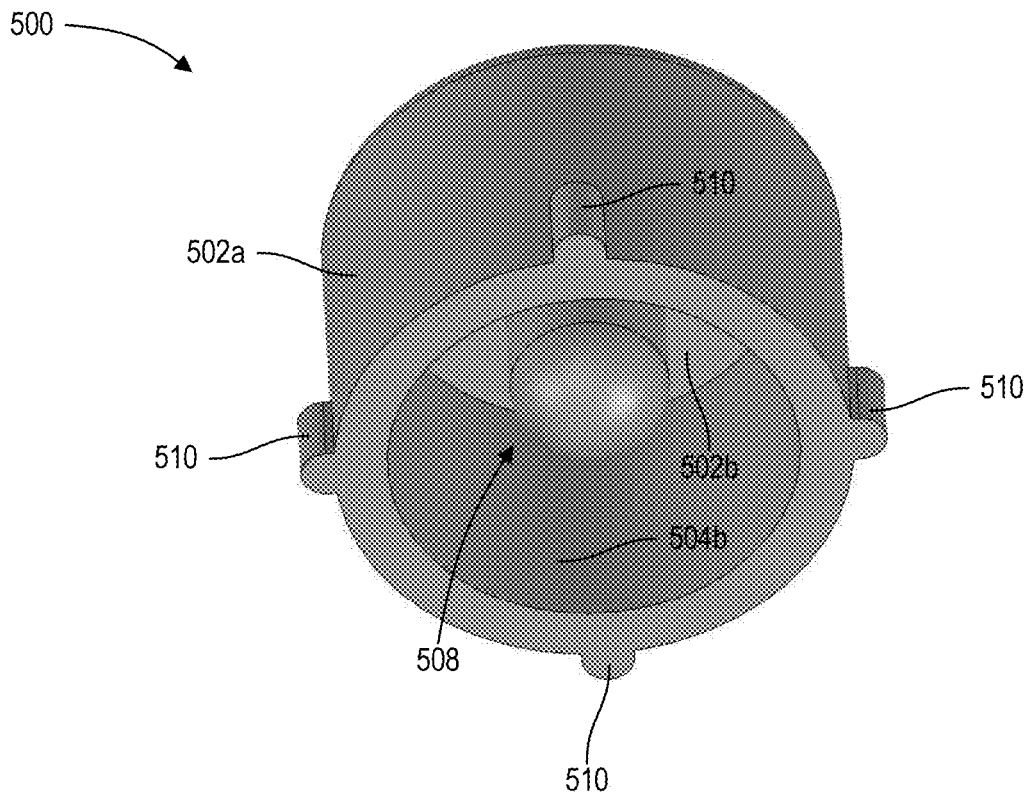
Figure 44B:
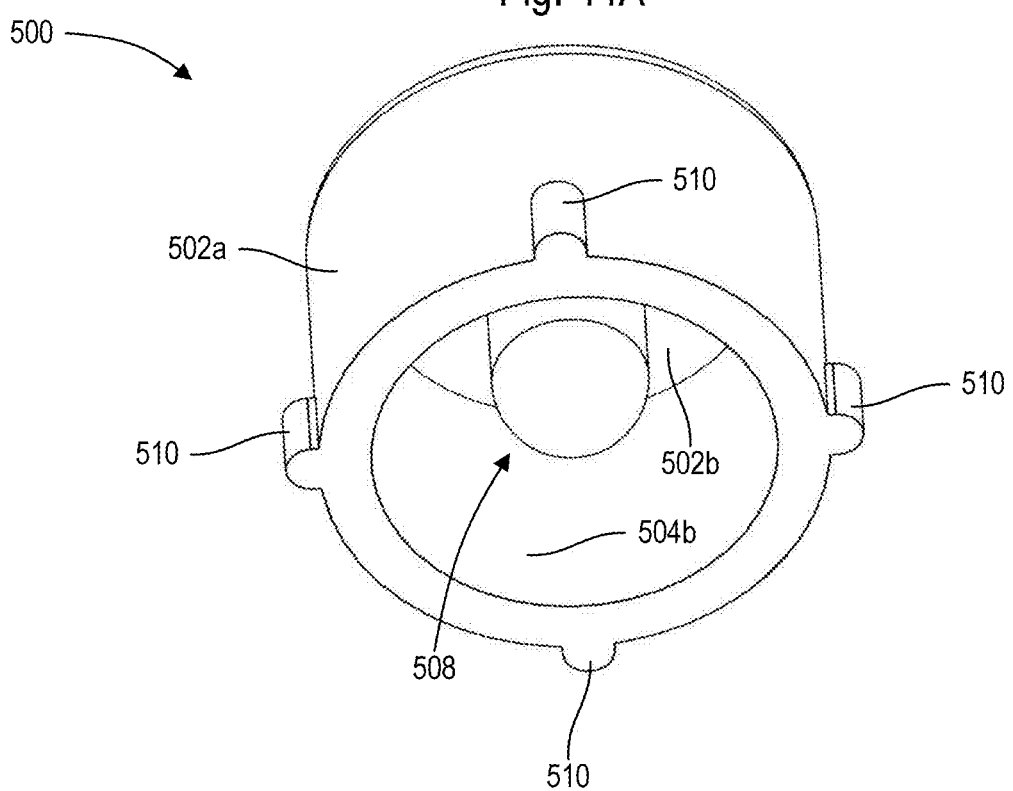
Figure 45:
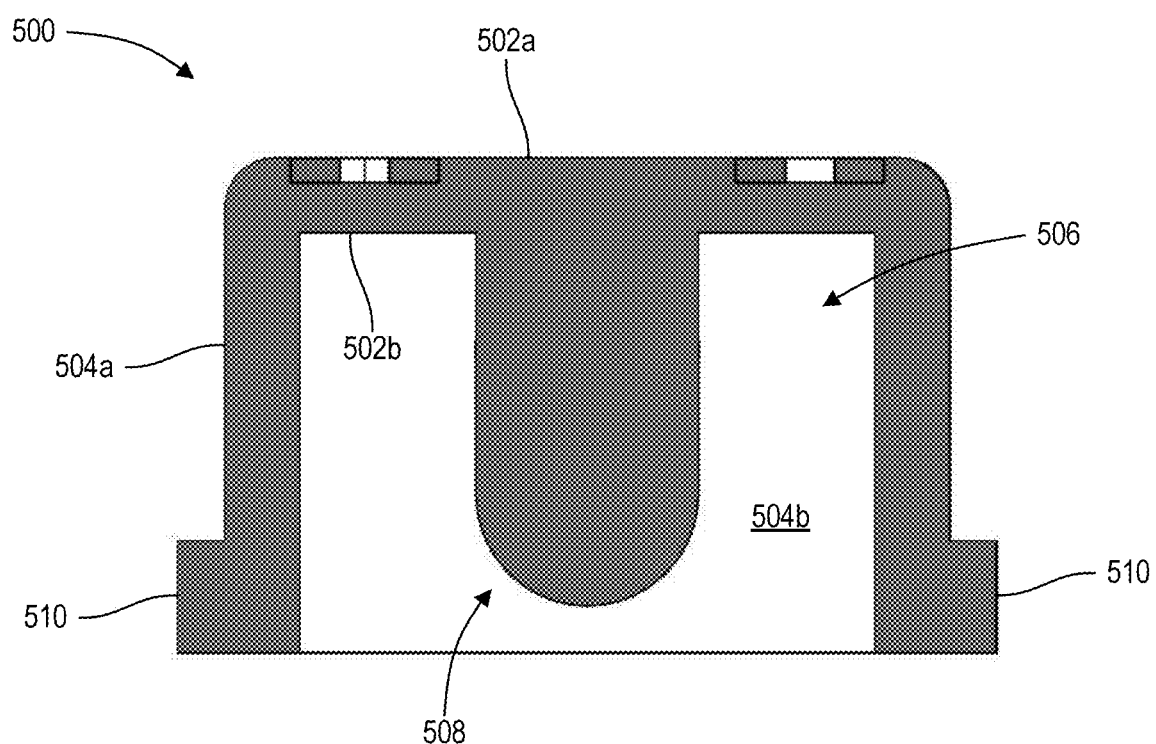

With reference to FIGS. 42A and 42B, the vacuum pin 400 is shown in accordance with an exemplary embodiment. The vacuum pin 400 is generally cylindrical in shape and extends between a proximal end 402 and a distal end 404. The vacuum pin 400 includes a barrel 406 that defines the proximal end 402 and a handle 408 that defines the distal end 404. The vacuum pin 400 also includes a first and second flat surface 410 between the barrel 406 and the handle 408. The flat surfaces 410 extend longitudinally between a first rim 412 and a second rim 414. The flat surfaces 410 extend perpendicular to and longitudinally between the rims 412 and 414.

The barrel 406 includes a first groove 416 and a second groove 416 shaped and dimensioned to accommodate a first and second elastomeric O-ring 418. When the vacuum pin 400 is disposed within the vacuum pin receptacle 310, the elastomeric O-rings 418 contact the inner surface of the chamber 314 such that the vacuum pin 400 creates an airtight seal within the chamber 314. This seal allows for the application of positive or negative pressure as needed.

The vacuum pin 400 may be moved within or completely removed from vacuum pin receptacle 310. When the vacuum pin 400 is transitioned from an undeployed portion (i.e., a position in which the vacuum pin 400 is fully inserted within the chamber 314 of the vacuum pin receptacle 310) to a deployed position (i.e., when the vacuum pin is moved within the vacuum pin receptacle away from the center of the base 300), a volume between the proximal end 402 of the vacuum pin 400 and the chamber 314 increases thereby creating a negative pressure within the chamber 314 which in turn causes the creation of a negative pressure within the physiological sample channel 338 via the vacuum channel 342 and the diagnostic test strip housing 330. Stated another way, when the vacuum pin 400 is moved from the undeployed position to the to the deployed position, the vacuum pin 400 creates a vacuum within the base 300 which draws a physiological sample from the physiological sample well 336 to the diagnostic test strip 18.

As previously discussed herein, the cover 200 includes a U-shaped locking member 224. When the cover 200 is coupled to base 300 the arms of the U-shaped locking member 224 extend through the gap 316 of the vacuum pin receptacle 310. Furthermore, when the vacuum pin 400 is in the undeployed position, the arms of the U-shaped locking member 224 are disposed between the rims 412 and 414. When the vacuum pin 400 is moved to the deployed position, the arms of the U-shaped locking member 224 contact the first rim 412 thereby preventing the vacuum pin 400 from moving further. As previously discussed, moving the vacuum pin 400 to the deployed position creates a vacuum within the base 300. Accordingly, the extent of movement of the vacuum pin 400 permitted by the U-shaped locking member 224 can determine the strength of a vacuum created within the base 300. The rims 412 and 414 are separated by a given distance. In other embodiments of the vacuum pin 400, the rims 412 and 414 are separated by a difference distance. This distance determines the extent by which the vacuum pin 400 can be removed from the vacuum pin receptacle 310 and as such can determine the strength of a vacuum created within the base 300. Hence, increasing or decreasing a distance between rims 412 and 414 increases or decreases the strength of a vacuum that can be created by the vacuum pin 400. The strength or amount of vacuum may also be increased by increasing a length of the vacuum pin receptacle 310, by increasing length of the vacuum pin 400, and/or by increasing the diameter of the vacuum pin receptacle 310.

With reference to FIGS. 43A, 43B-45 the button 500 is depicted in accordance with an exemplary embodiment. The button 500 includes a top wall 502 with an outer surface 502a and an opposed inner surface 502b. The button 500 also includes a side wall 504 with an outer surface 504a and an opposed inner surface 504b. The top wall 502 extends longitudinally from and perpendicular to the side wall 504. The side wall 504 extends vertically from and perpendicular to the top wall 502. The top wall 502 and the side wall 504 have generally circular cross sections and are concentric with one another. The inner surface 502a of the top wall 502 and the inner surface 504a of the side wall 504 define an inner volume 506 of the button 500.

The button 500 also includes a cylinder 508 that extends vertically from and perpendicular to the inner surface 502b of the top wall 502. The cylinder 508 is concentric with the top wall 502 and the side wall 504. The button 500 also includes a plurality of protrusions 510 that extend from the outer surface 504a of the side wall 504. The protrusions 510 couple the button 500 to the cover 200.

Figure 46A:
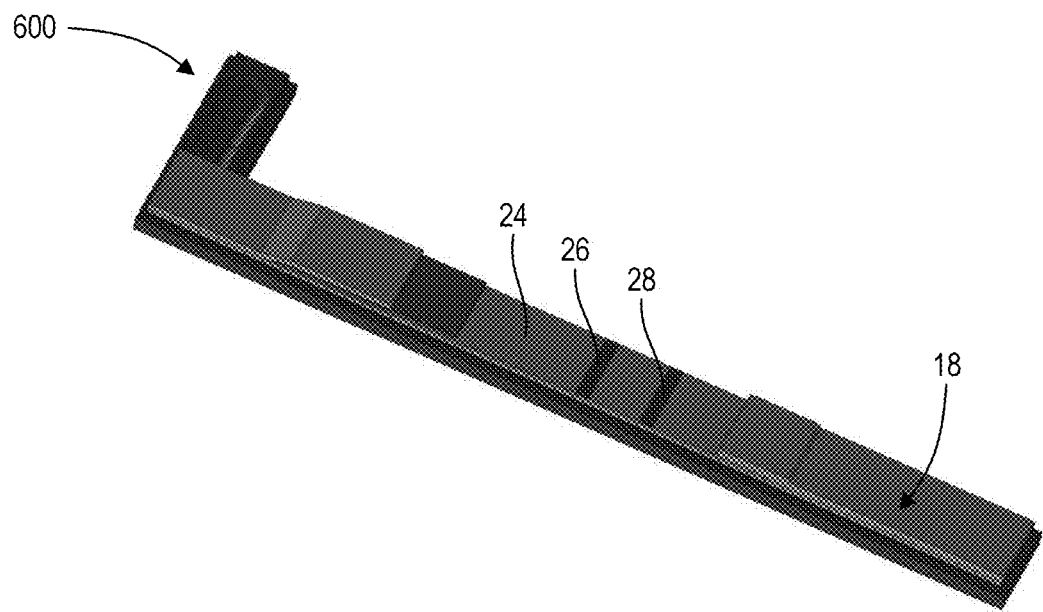
FIGS. 46A and 46B depict a test strip support with a diagnostic test strip in accordance with an exemplary embodiment of the present disclosure.
Figure 46B:
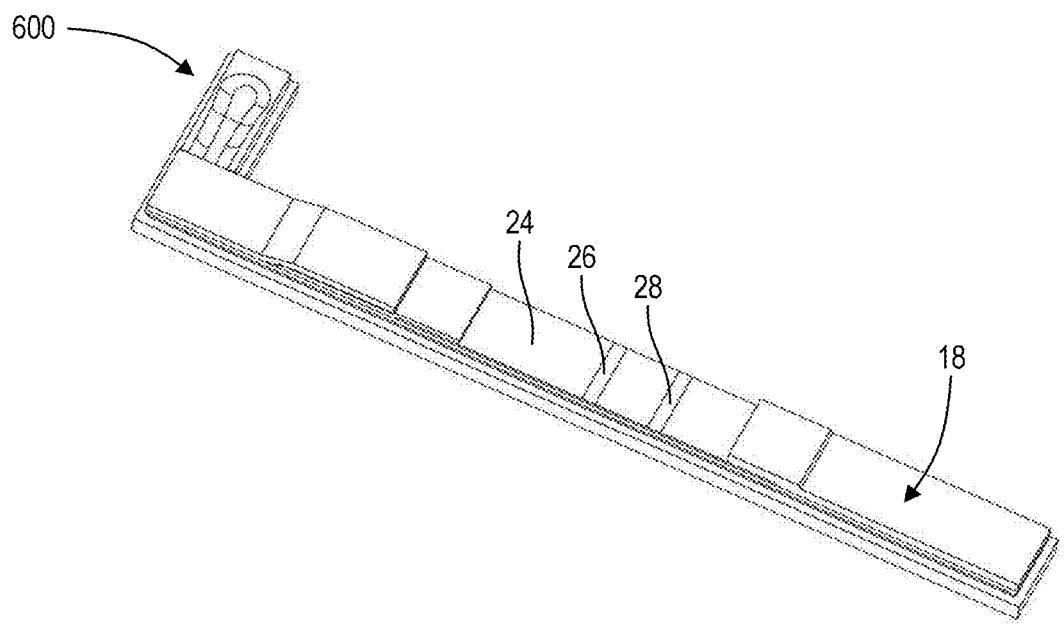
Figure 47A:
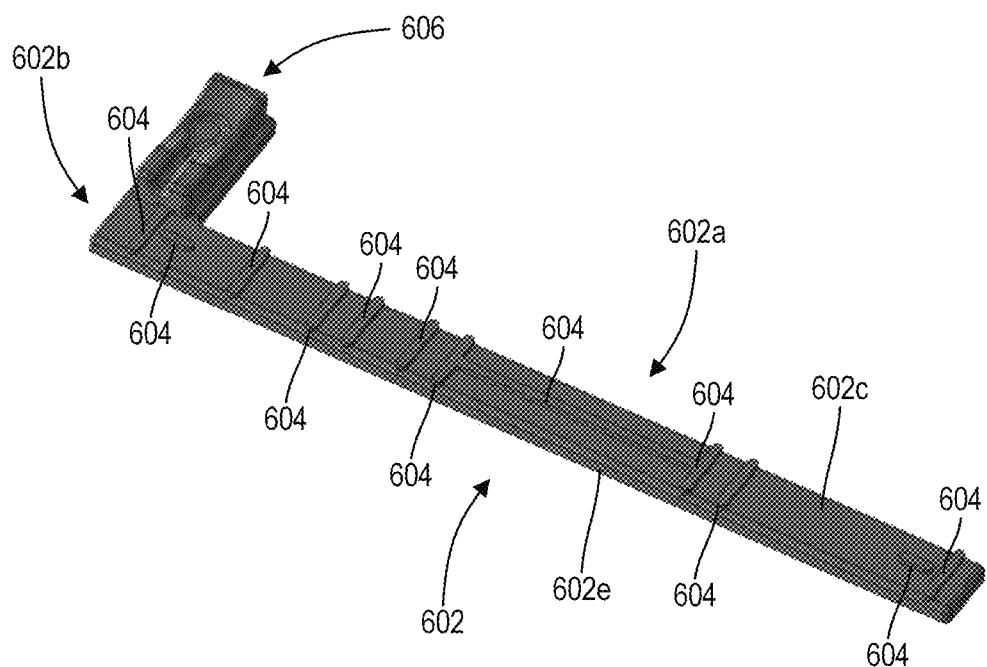
FIGS. 47A, 47B, 48A, and 48B depict a test strip support in accordance with an exemplary embodiment of the present disclosure.
Figure 47B:
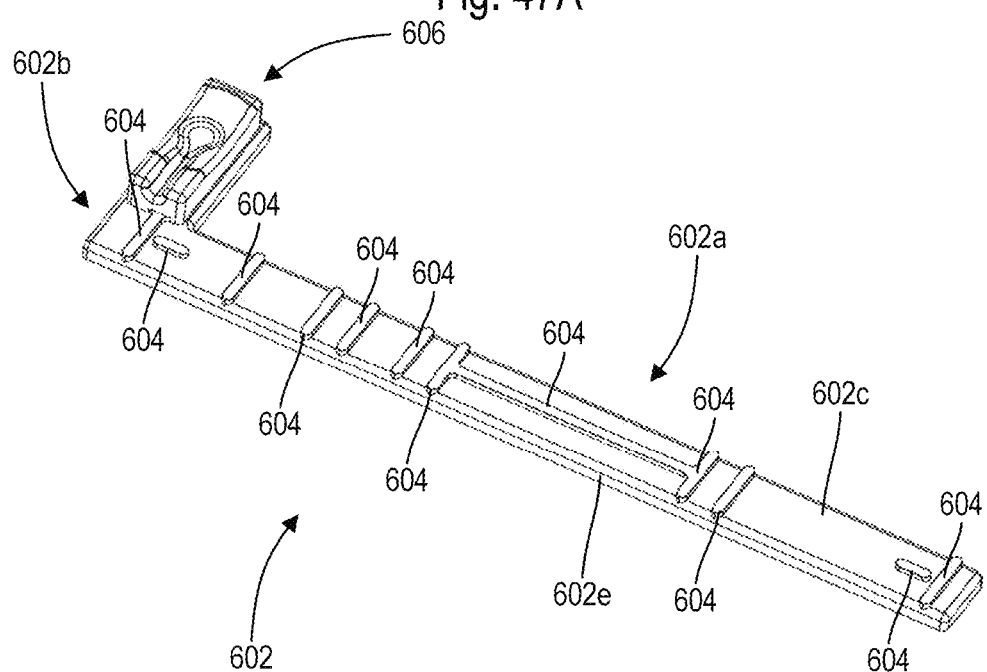
Figure 48A:
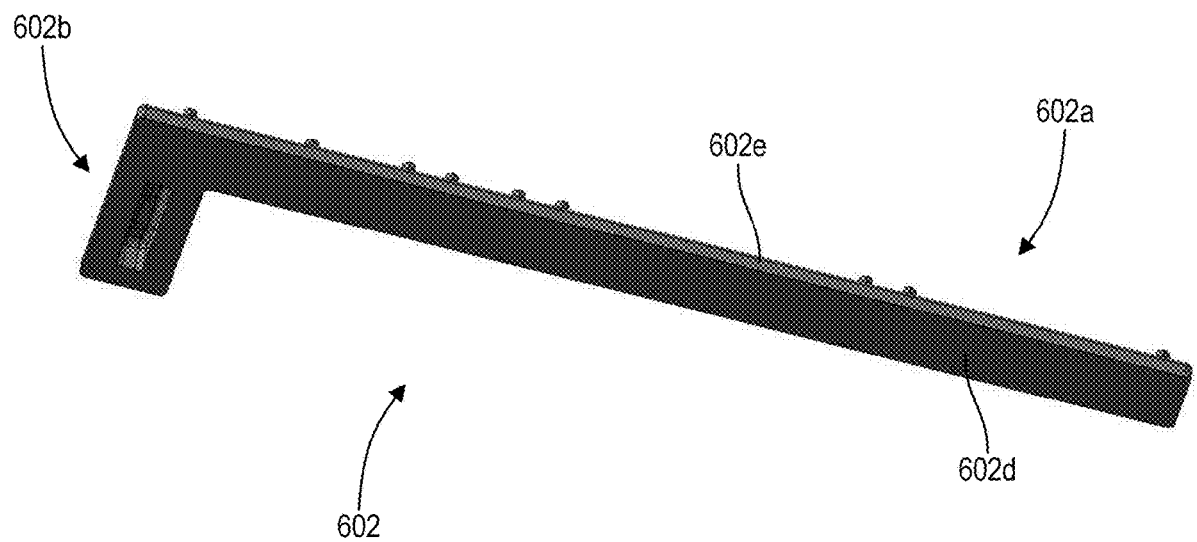
Figure 48B:
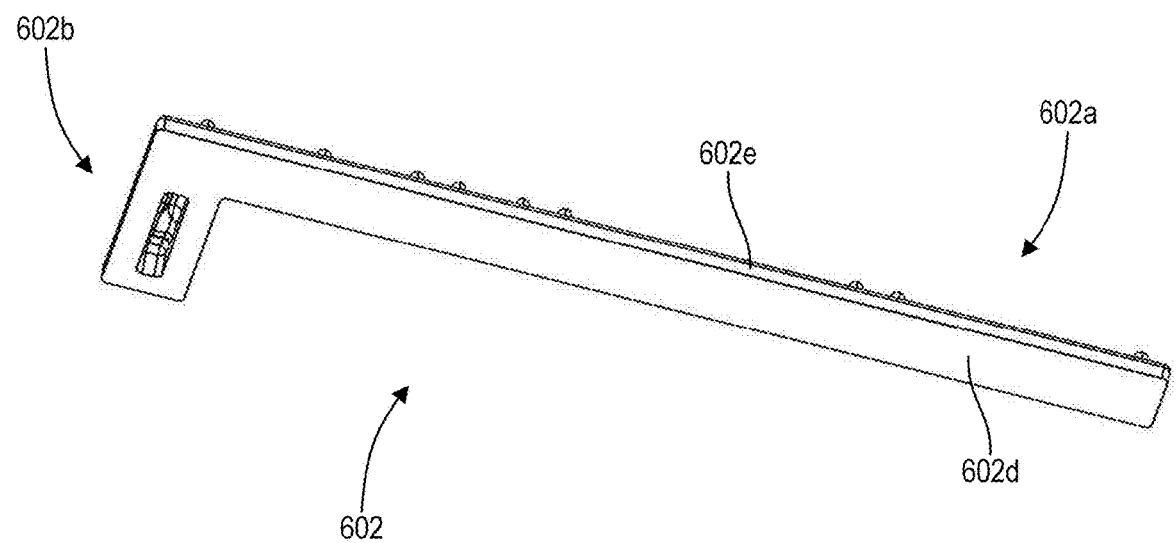

With reference to FIGS. 46A and 46B, the test strip support 600 and the diagnostic test strip 18 is shown in accordance with an exemplary embodiment.

As shown in FIGS. 47A, 47B, 48A, and 48B, the test strip support 600 includes an L-shaped base 602 with a first portion 602a and a second portion 602b that is perpendicular the first portion 602a.

The base 602 includes a top surface 602c, an opposed bottom surface 602d, and a side surface 602e that extends vertically between and perpendicular the top surface 602c and the bottom surface 602d. The side surface 602e gives the base 602 a height substantially that matches a height of the bottom wall 302 of the base 300. As such when the test strip support 600 is coupled to the base 300, the top surface 602c of the base 602 is flush with the top surface 302a of the bottom wall 302 and the bottom surface 602d of the base 602 is flush with the bottom surface 302b of the bottom wall 302.

The first portion 602a of the base 602 is shaped and dimensioned to support the diagnostic test strip 18. Furthermore, the base 602 includes a plurality of protrusions 604 that extend vertically from and perpendicular to the top surface 602c of the base 602. When the diagnostic test strip 18 is disposed on the test strip support 600, the diagnostic test strip 18 rests upon the protrusions 604. The protrusions 604 can prevent the test strip 18 from delaminating (i.e., the protrusions 604 can ensure that layers of the test strip 18 contact one another such that the physiological sample can transfer from one layer to another).

The second portion 602b of the base 602 includes a well 606 that extends vertically from and perpendicular to the top surface 602c of the base 602. When the test strip support 600 is coupled to the base 300, the well 606 extends into the inner volume 332 of the diagnostic test strip housing 330 and is positioned vertically below the buffer aperture 348. Furthermore, the well 606 is shaped and dimensioned to accept a processing fluid from the processing fluid pack 16 via the buffer aperture 348. A bottom surface of the well 606 is angled toward the first portion 602a of the base 602 and therefore directs a received fluid towards the diagnostic test strip 18 when the diagnostic test strip 18 is disposed on the first portion 602a of the base 602.

Figure 49:
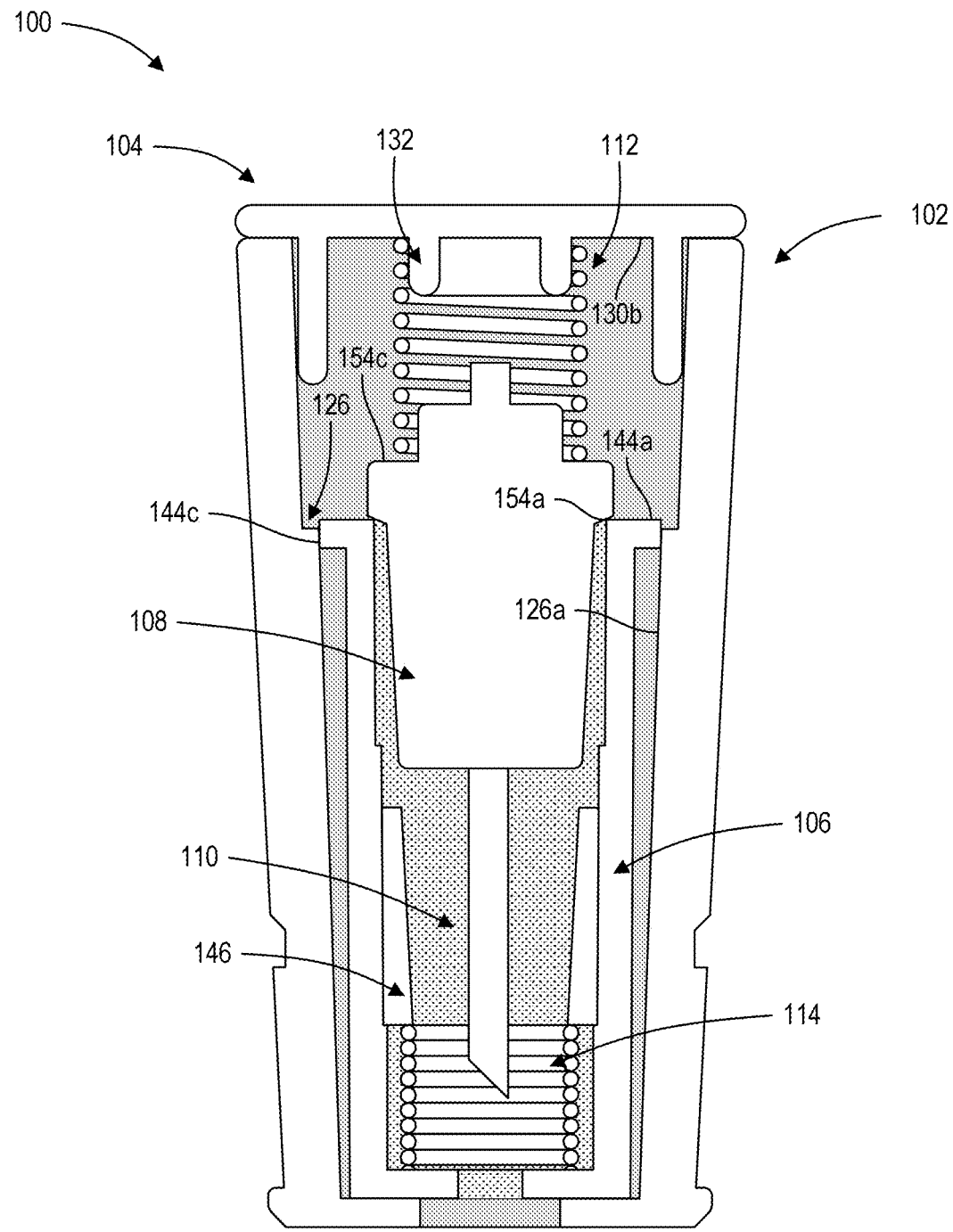
FIG. 49 depicts the lancet of the dermal patch system in an undeployed position in accordance with an exemplary embodiment of the present disclosure.
Figure 50:
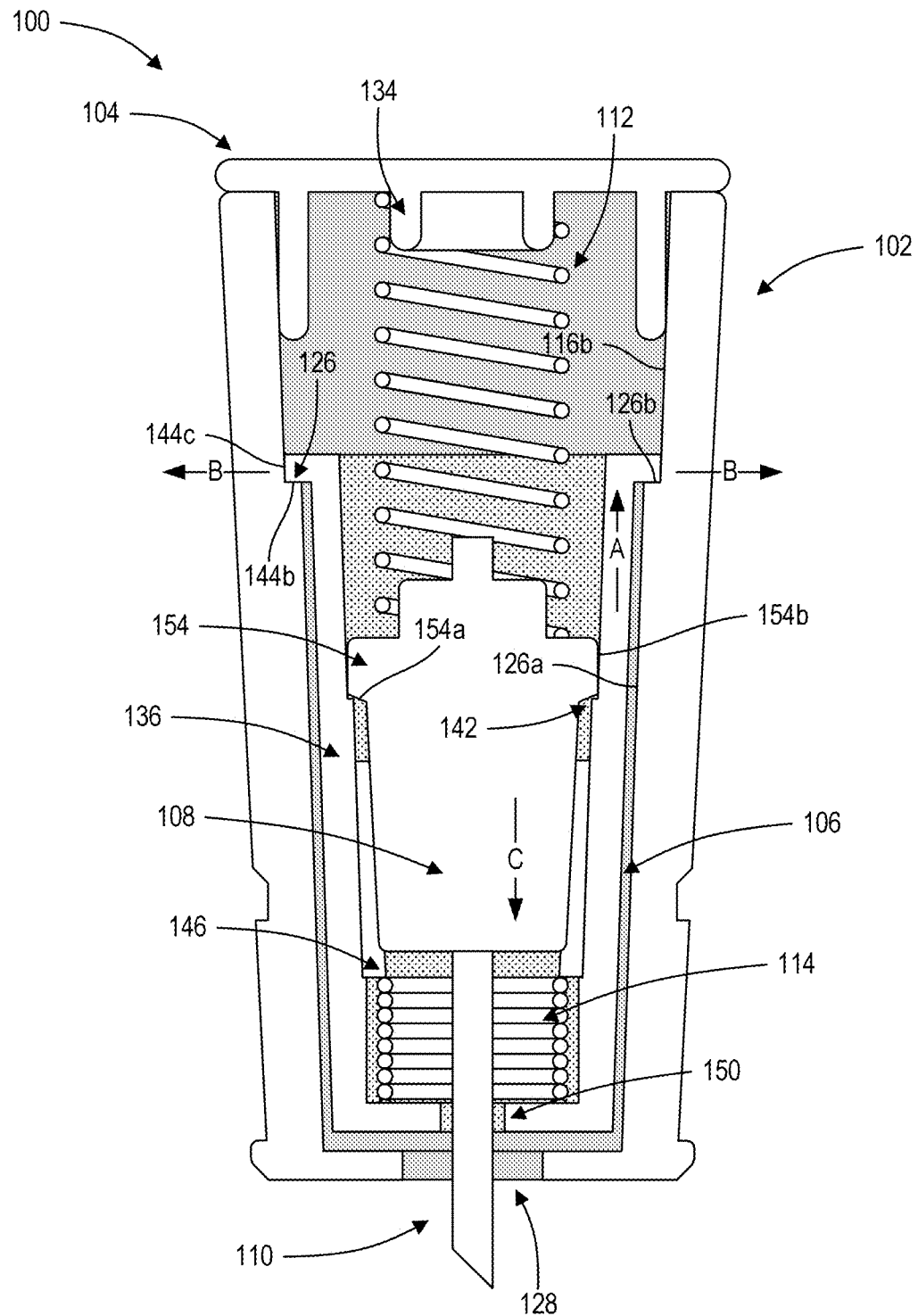
FIG. 50 depicts the lancet of the dermal patch system in a deployed position in accordance with an exemplary embodiment of the present disclosure.
Figure 51:
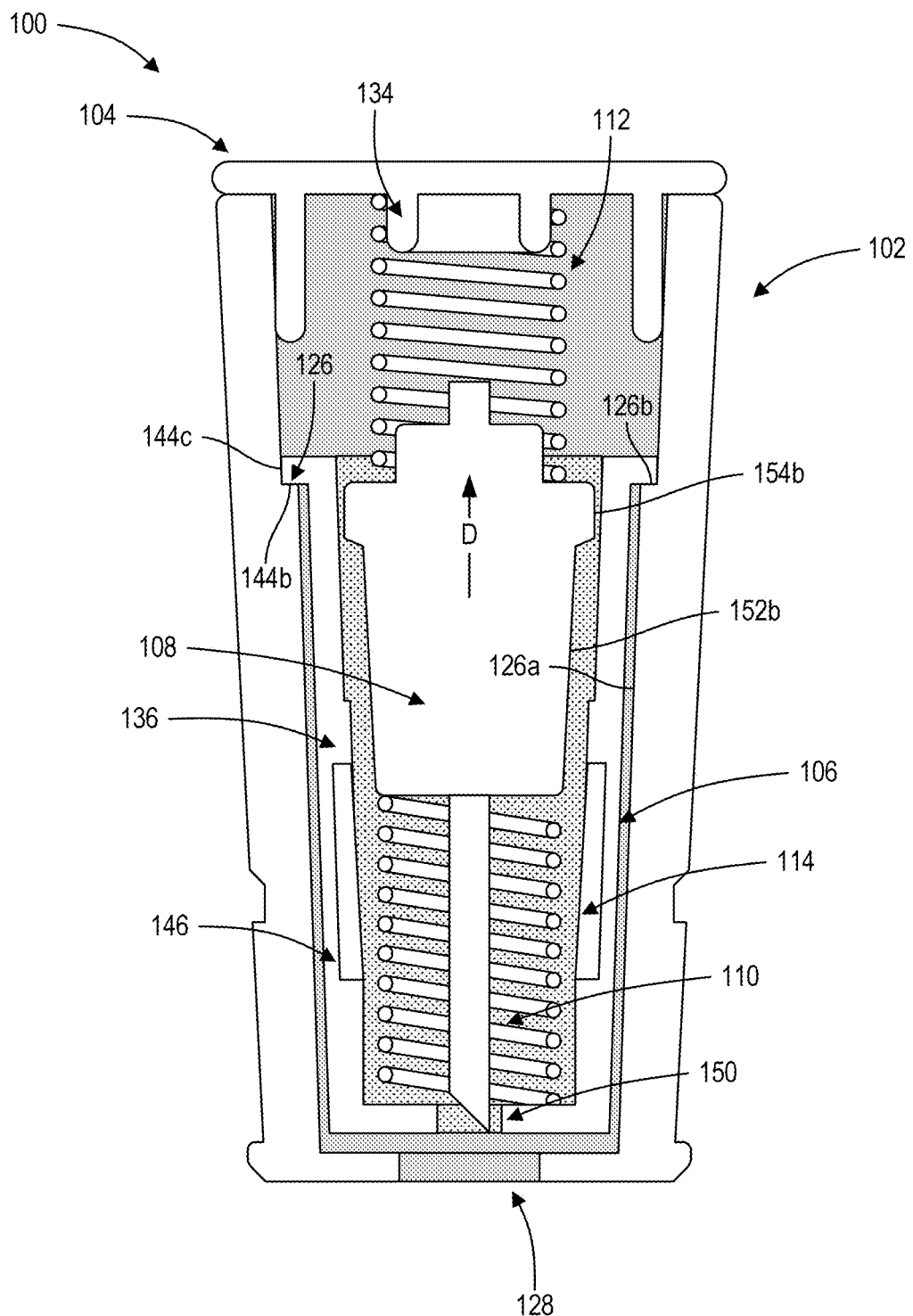
FIG. 51 depicts the lancet of the dermal patch system in a retracted position in accordance with an exemplary embodiment of the present disclosure.
Figure 52:
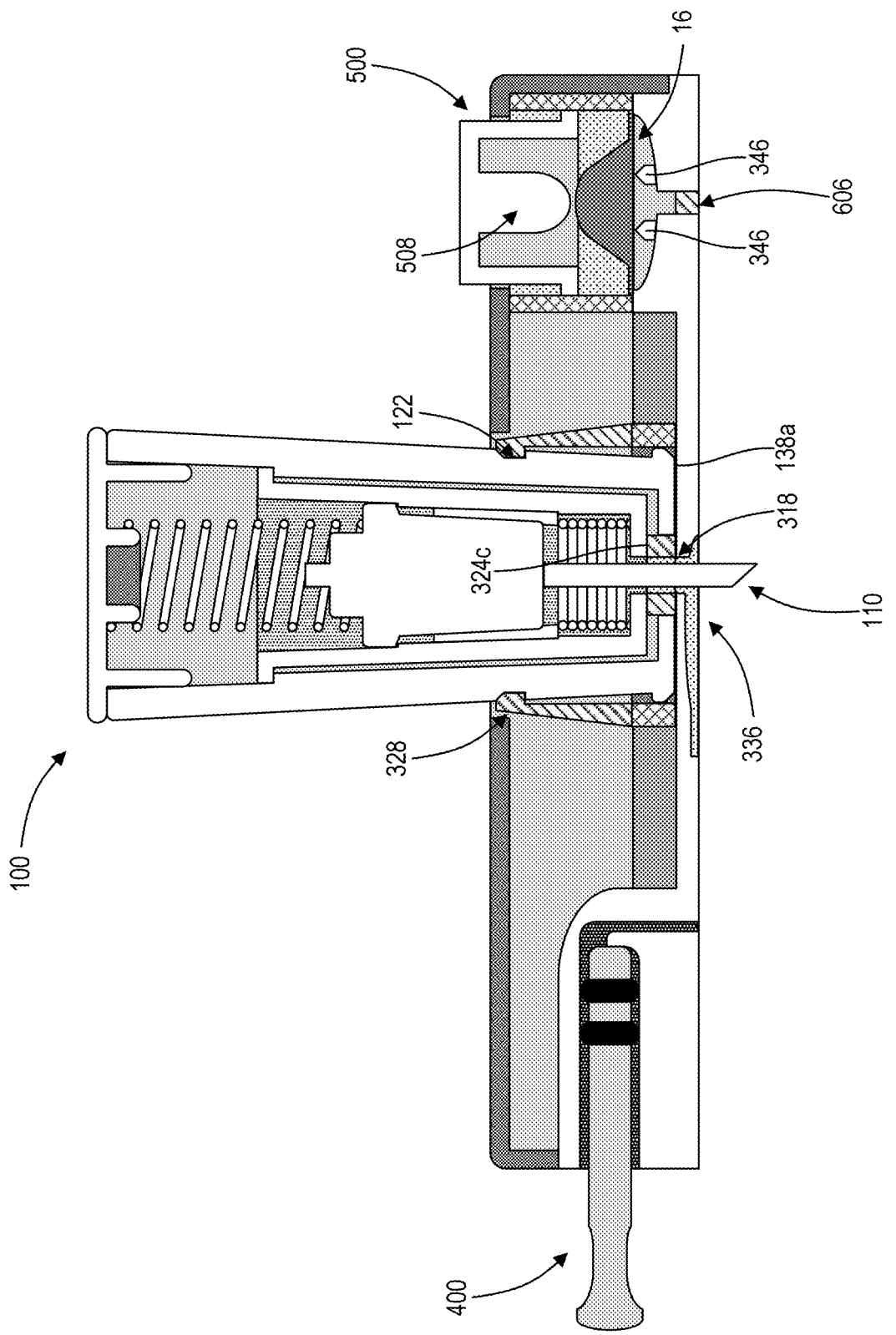
FIG. 52 depicts the lancet coupled to the cartridge, wherein the lancet is in a deployed position in accordance with an exemplary embodiment of the present disclosure.
Figure 53:
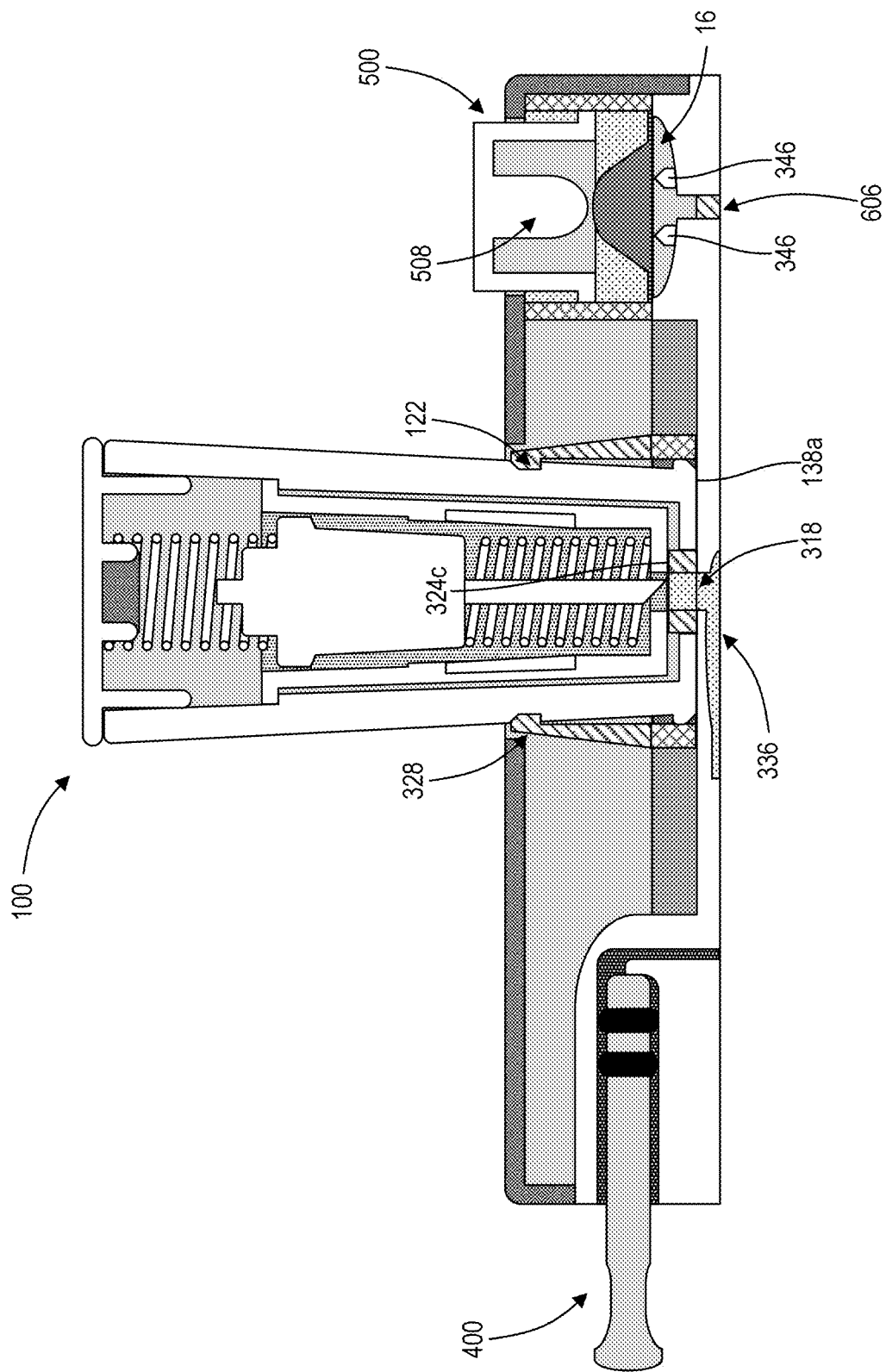
FIG. 53 depicts the lancet coupled to the cartridge, wherein the lancet is in a refracted position in accordance with an exemplary embodiment of the present disclosure.

As depicted in FIGS. 49-51, the lancet 100 is moveable between a first position (also referred to as an "undeployed position") (FIG. 49), a second position (also referred to as a "deployed position") (FIG. 50), and a third position (also referred to as a "retracted position") (FIG. 51).

In the undeployed position (before the lancet 100 is inserted into the cartridge 12; FIG. 49) the injection spring 112 and the retraction spring 114 are in a compressed state. In the compressed state, the retraction spring 114 extends vertically between the bottom wall 138 and a proximal end of the locking members 146. More specifically, a distal end of the retraction spring 114 contacts a lower surface of the proximal end of the locking members 146 and a proximal end of the retraction spring 114 contacts the inner surface 138b of the bottom wall 138.

When in the undeployed position the outer surface 144c contacts the inner surface 126a of the columns 126 which compresses the side wall 136 inwardly. Furthermore, the bottom surface 154a of the second cylinder 154 contacts and rests upon the top surfaces 144a of the ledges 144 such that the ledges 144 supports the needle frame 108 in the undeployed position. In this position, the injection spring 112 is prevented from decompressing (due to the second cylinder 154 resting upon the ledges 144) and the needle 110 is disposed completely within the inner volume 140 of the inner sleeve 106.

When the lancet 100 is inserted into the cartridge 12, the engagement of the lancet with the cartridge 12 causes the lancet 100 to automatically move from the undeployed position to the deployed position.

When the lancet 100 is coupled to the base 300 (FIGS. 52-55), the inner circular projection 324 extends through the aperture 128 to contact the bottom wall 138. Specifically, the top surface 324c of the inner circular projection 324 contacts the outer surface 138a of the bottom wall 138 which forces the inner sleeve 106 to move vertically upward in the direction of arrow A (FIG. 50) within the housing 102. This vertical movement causes the ledges 144 to extend vertically above the top surfaces 126b of the columns 126. Moving beyond the top surfaces 126b of the columns 126 allows the side wall 136 to decompress and expand in the direction of arrow B (FIG. 50) and extend toward the inner surface 116b of the side wall 116. In this position, the bottom surface 144b of the ledges 144 rest upon the top surfaces 126b of the columns 126 and the outer surfaces 144c of the ledges 144 contacts the inner surface 116b of the side wall 116. Furthermore, when the lancet 100 is inserted into the cartridge 12, the hooks 328 of the locking members 326 are disposed within and coupled to the notch 122 via a snap fit.

The expansion of the side wall 136 causes the inner volume 140 of the inner sleeve 106 to have a larger width relative to when the inner sleeve 106 is in the undeployed position such that at least a portion of the side wall 136 has a larger width than the second cylinder 154 (the widest portion of the needle frame 108 which allows the needle frame 108 move vertically downward in the direction of arrow C) (FIG. 50).

Furthermore, the injection spring 112 also causes the needle frame 108 to move in the direction of arrow C as the ledges 144 no longer prevent the injection spring 112 from expanding. The force applied by the injection spring 112 causes the needle frame 108 (and therefore the needle 110) to travel with a force that is sufficient to cause the needle 110 to puncture the skin of a subject wearing the dermal patch system 10. Stated another way, the injection spring 112 causes the needle 110 to extend through the aperture 150 of the inner sleeve 106, through the aperture 128 of the housing 102, and through the needle aperture 318 of the base 300 to puncture the skin of a subject. In the deployed position, the bottom surface 154a of the second cylinder 154 rests upon the columns 142 and at least a portion of the outer surface 154b of the second cylinder 154 contacts the inner surface 136b of the side wall 136.

While moving in the direction of arrow C, the outer surface 152b contacts the locking members 146 which causes a proximal portion of locking members 146 that is aligned with an opening 148 to extend into the opening. In this position, the locking members 146 no longer contact the retraction spring 114 thereby allowing the retraction spring 114 to decompress and expand. When decompressed, the retraction spring 114 contacts the outer surface 152b of the first cylinder 152 which causes needle frame 108 to also move in the direction of arrow D (FIG. 51). That is after moving to the deployed position, the retraction spring 114 causes the needle 110 to retract back into the inner volume 140 of the inner sleeve 106 via the aperture 150 of the base 300 and the apertures 128 and 150 of the lancet 100. After penetrating the skin of a subject, the refraction spring 114 causes the needle 110 to automatically retract back into the housing of the lancet 100 thereby placing the lancet 100 in the retraced position.

As previously discussed herein, the lancet includes a mechanism can be transition the lancet between a locked state and a released state. In various embodiments, this mechanism includes the columns 126, the ledges 144, and the locking members 146. An upper locking portion of the mechanism refers to the columns 126 and the ledges 144 while a locker locking portion refers to the locking members 146 as the columns 126 and the ledges 144 can be positioned vertically above the locking members 146. The term upper interference portion refers to the top surface 144a of the ledges 144 as this surface interferes with the needle frame's 108 ability to transition to the deployed position when the mechanism is in the locked state. As used herein, a lower interference member refers to the columns 142 as the columns 142 interfere with the needle frame's 108 ability to further extend beyond a desired position.

In use, after affixing the cartridge 12 to the skin of the subject, a user of the dermal patch system 10 inserts the lancet into the cartridge 12 which causes the needle 110 to move to the deployed position and puncture the subject's skin and draw a physiological sample. After the needle 110 retracts into the lancet 100, the drawn physiological sample pools within the physiological sample well 336 of the base 300.

Figure 54:
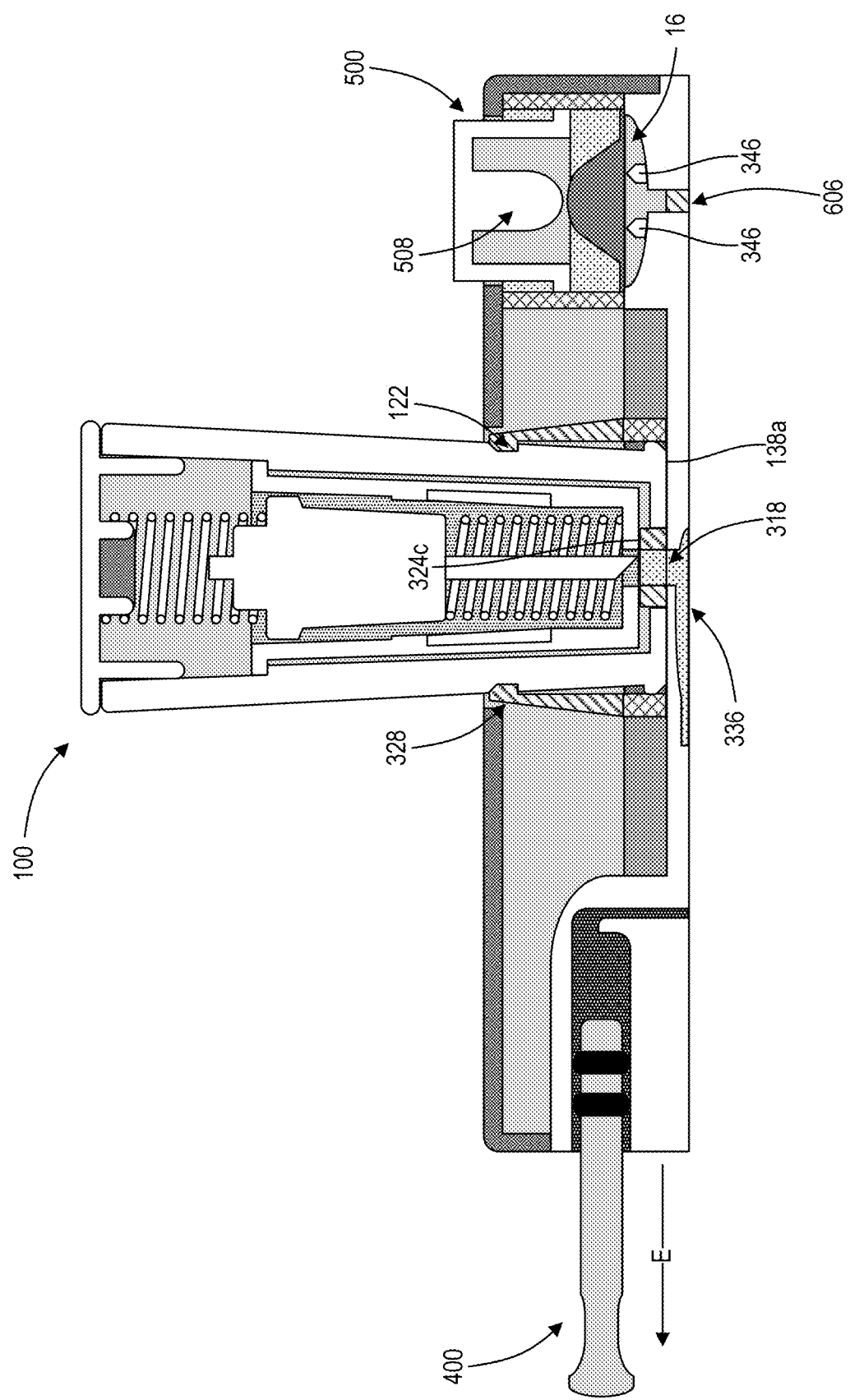
FIG. 54 depicts the lancet coupled to the cartridge, wherein a vacuum pin of the cartridge is in a deployed position in accordance with an exemplary embodiment of the present disclosure.
Figure 55:
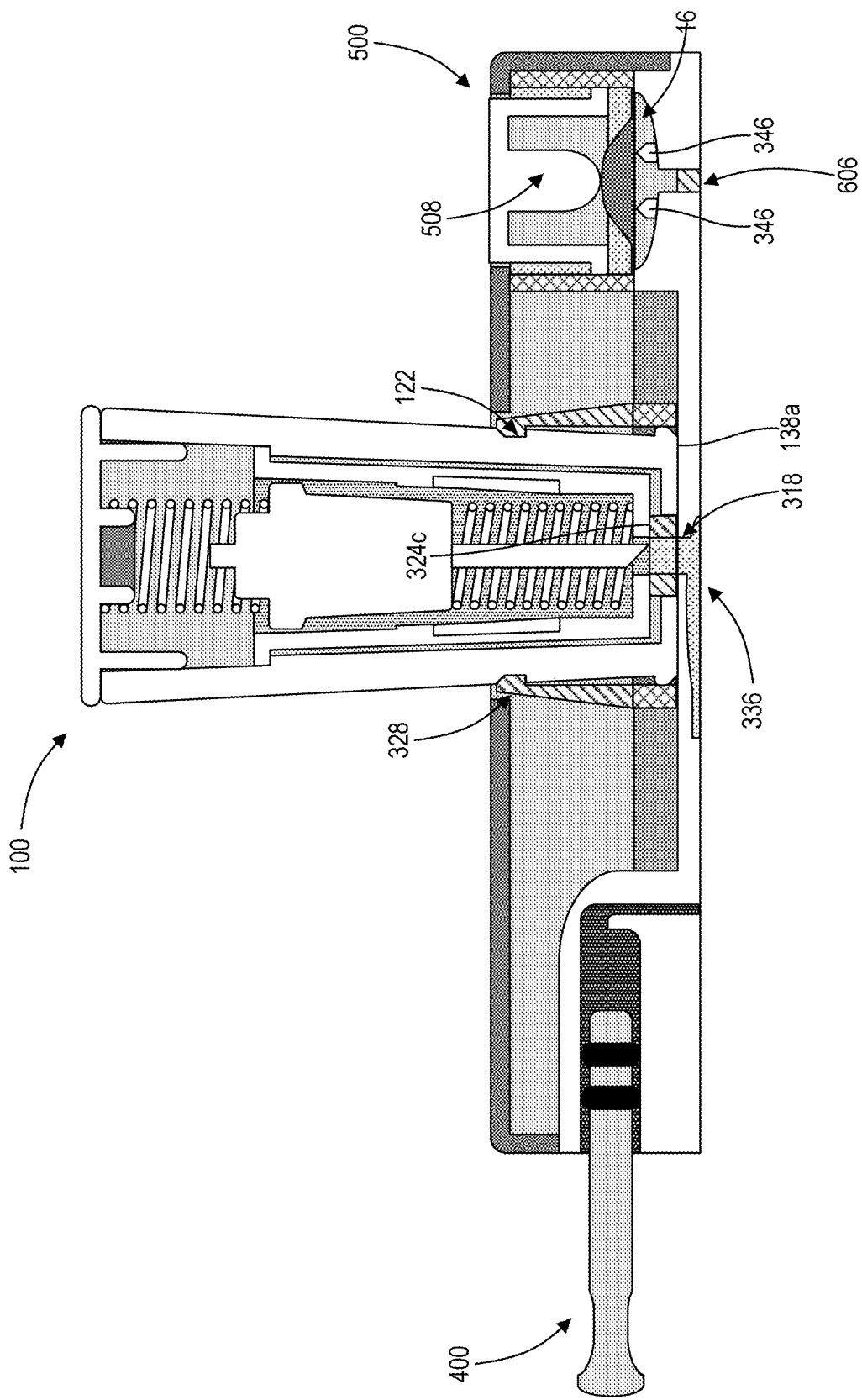
FIG. 55 depicts the lancet coupled to the cartridge, wherein a button and a vacuum pin of the cartridge are in a deployed position in accordance with an exemplary embodiment of the present disclosure.

As depicted in FIGS. 52-55, the button 500 is moveable between a first position (also referred to as a "locked" position) (FIGS. 52 and 53), a second position (also referred to as an "unlocked" position), and a third position (also referred to as a "deployed" position) (FIGS. 54 and 55).

In the locked position, the protrusions 510 are disposed between and within the horizontal grooves 232 of the button guide 228. In this position, the horizontal grooves 232 prevent a user of the dermal patch system 10 from moving the button 500 into the deployed position. A user of the dermal patch system 10 can rotate the button 500 to the unlocked position. In the unlocked position the protrusions 510 are aligned with the vertical grooves 230 of the button guide 228 and the horizontal grooves 232 do not prevent a user from moving the button 500 into the deployed position. That is, in the unlocked position, a user of the dermal patch system 10 may move the button 500 into the deployed position by pressing the button 500. When moving to the deployed position, the protrusions 510 travel downward within the vertical grooves 230.

Moving the button 500 to the deployed position places at least a portion of the processing fluid pack 16 within the inner volume 506 and causes the cylinder 508 to compress the processing fluid pack 16 into the piercing elements 346 which causes the processing fluid pack 16 to rupture and release the stored processing fluid. The released processing fluid travels to the diagnostic test strip 18 via the buffer aperture 348 and the well 606. The well 606 can slow the flow of the processing fluid from the processing fluid pack 16 and allows the processing fluid to be more easily wicked by the diagnostic test strip 18 which may mimic the rate at which a diagnostic test strip outside of the dermal patch system 10.

A user of the dermal patch system 10 may move the button 500 to the deployed position thereby releasing the processing fluid before or after drawing the physiological sample.

When the physiological sample is within the physiological sample well 336 and before rupturing the processing fluid pack 16, a user of the dermal patch system 10 can pull the vacuum pin 400 in the direction of arrow E (FIG. 55) to move the vacuum pin 400 from a first position (also referred to as an "undeployed" position) (FIGS. 52-54) to a second position (FIG. 55) (also referred to as an "deployed" position). Moving the vacuum pin 400 to the deployed position creates a vacuum within the vacuum channel 342 which causes the drawn physiological sample to travel to the diagnostic test strip 18 via the physiological sample channel 338. In some such embodiments, the flow of the drawn physiological sample can be aided by capillary action, gravity and wicking action. As previously discussed herein, en route to the diagnostic test strip 18, the drawn physiological sample passes through the reservoir 340. The user may verify the drawn physiological sample is traveling to the diagnostic test strip 18 by verifying at least a portion of the drawn physiological sample is within the reservoir 340 via the sample viewing aperture 214.

After pulling the vacuum pin 400, the user pushes the button 500 which releases the processing fluid and causes the processing fluid to mix and interact with the physiological sample to form a processed physiological sample. The processed physiological sample is washed across the diagnostic test strip 18. The processed physiological sample can be configured to facilitate the detection of a target biomarker of interest, if any, in the processed physiological sample via the diagnostic test strip 18. By way of example, when the physiological sample is the blood, the processing fluid can include an anti-coagulant to prevent coagulation of the drawn sample prior to its analysis. In some cases, the processing fluid can include a lysing agent for lysing cells present in a drawn sample, e.g., to allow analysis of genetic materials, e.g., DNA and/or RNA segments, within the cell.

The diagnostic test strip 18 can include, but is not limited to, a lateral flow assay, a Bio-marker sensing chip, and Iso-thermal amplification technology.

Figure 3A:
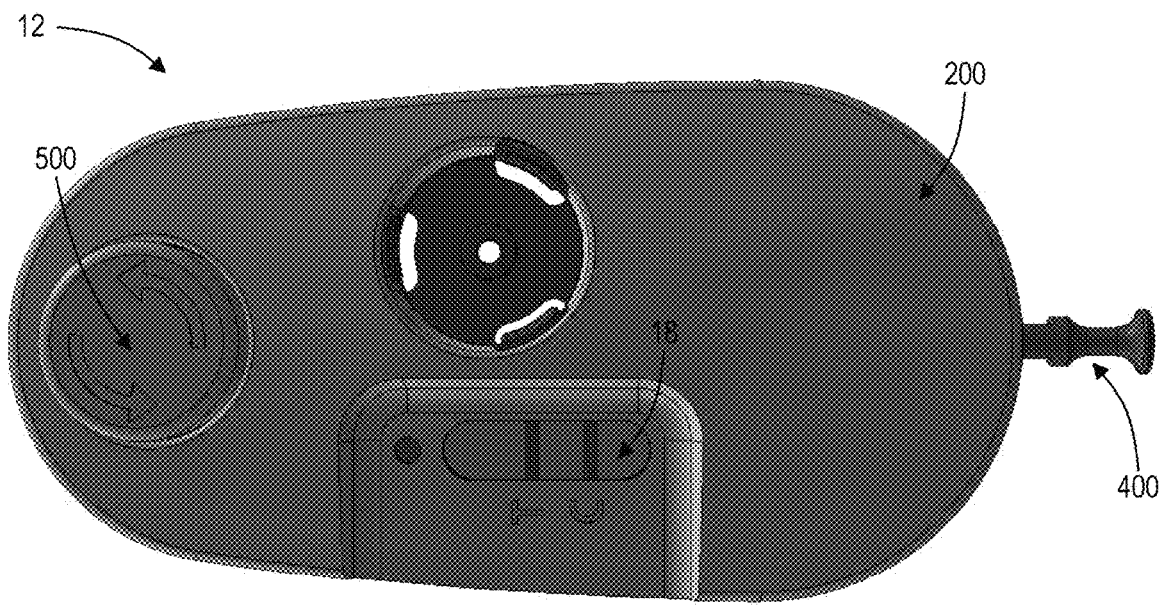
Figure 3B:
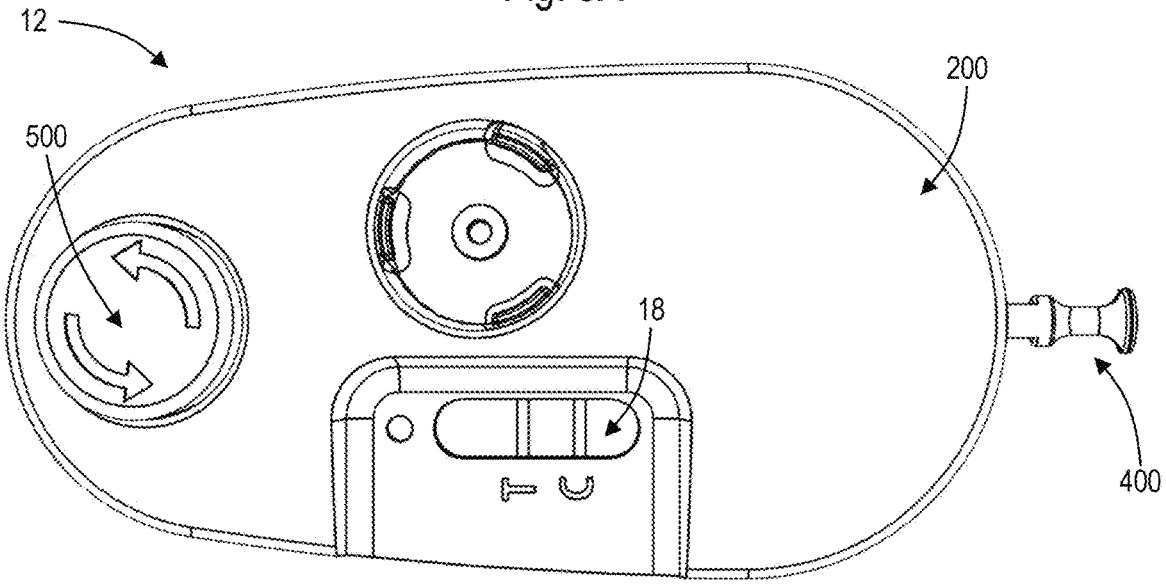

In an embodiment wherein the diagnostic test strip 18 is a lateral flow assay (FIGS. 3A and 3B), the diagnostic test strip 18 includes a nitrocellulose membrane 24 with a line of test capture antibodies 26 (FIGS. 46A and 46B) specific to a desired biomarker and a line of control capture antibodies 28 (FIGS. 46A and 46B). When the diagnostic test strip 18 is disposed within the cartridge 12, the line of test capture antibodies 26 is aligned with test result indicator 218 and the line of control capture antibodies 28 is aligned with the control indicator 220 which allows a user to visually determine if a biomarker (e.g., HbA1c, Cardiac Troponin, CBC, Creatinine, Infectious diseases, etc.) is present in the drawn physiological sample by viewing the diagnostic test strip 18 via the test strip viewing aperture 216.

In some embodiments, after the diagnostic test strip 18 includes the processed physiological sample, the user can remove the dermal patch system 10 from the skin of the subject and can send the dermal patch system to a medical professional. The medical professional can then view the diagnostic test strip 18 to determine if a biomarker is present in the drawn physiological sample.

Figure 56:
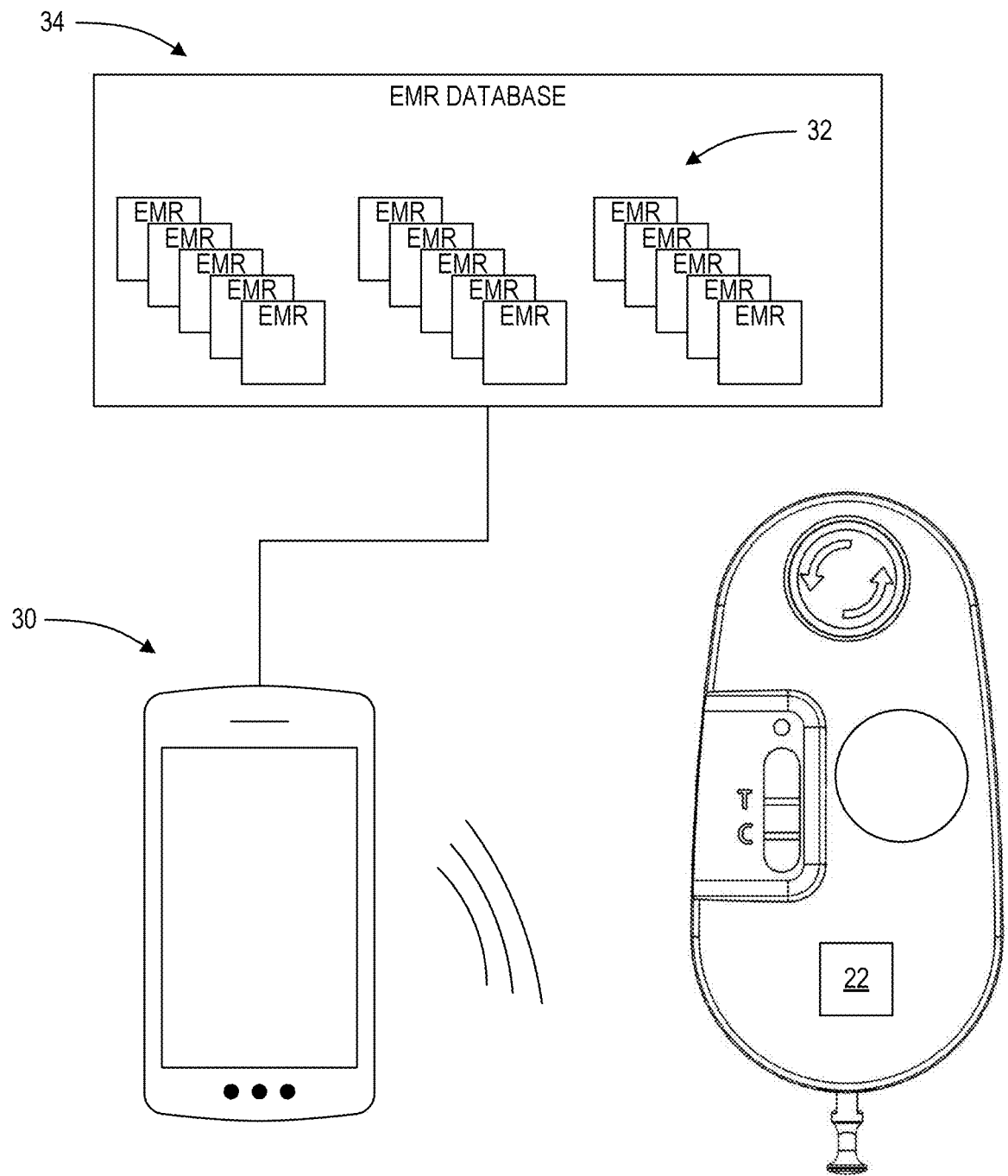
FIG. 56 diagrammatically depicts an electronic medical record database, a computer system, and a dermal patch system with a quick response ("QR") code in accordance with an exemplary embodiment of the present disclosure.

With reference to FIG. 56, in some embodiments wherein the dermal patch system 10 includes the QR code 22, a user of a computer system 30 may scan the QR code 22 to determine a test to perform on the stored physiological sample and/or to view and/or update an EMR 32 that is associated with the QR code 22. In these embodiments, the EMR 32 is stored in an EMR database 34 that is in communication with the computer system 30. Furthermore, the QR code 22 may be employed to preserve the chain of custody of the dermal patch system 10.

In these embodiments, the computer system 30 may include an application that provides access to the EMR database 34 via a network connection and allows a user to photograph of scan the QR code 22. As shown in FIG. 56, the EMR database 34 includes a plurality of EMRs 32 each of which is associated with an individual subject. The application causes the computer system 30 to scan or retrieve an image of the QR code 22, analyze the QR code 22 and associate the QR code 22 with an EMR 32. In some embodiments, the computer system 30 may then update the associated EMR 32 to indicate a diagnostic test has been run on the drawn physiological sample. The computer system 30 may automatically update the EMR 32 automatically or based on a user input. In some embodiments, after associating an EMR 32 with the QR code 22, the computer system 30 may analyze information within the EMR 32 to determine a diagnostic test that associated with the diagnostic test strip 18 and in some embodiments, the computer system 30 may utilize image recognition software to determine a result of the diagnostic test by determining the presence or absence of a test line on the diagnostic test strip 18 in an in an image captured by the computer system 30. In these embodiments, the computer system 30 may automatically update the associated EMR 32 to indicate the determined result.

Figure 57:
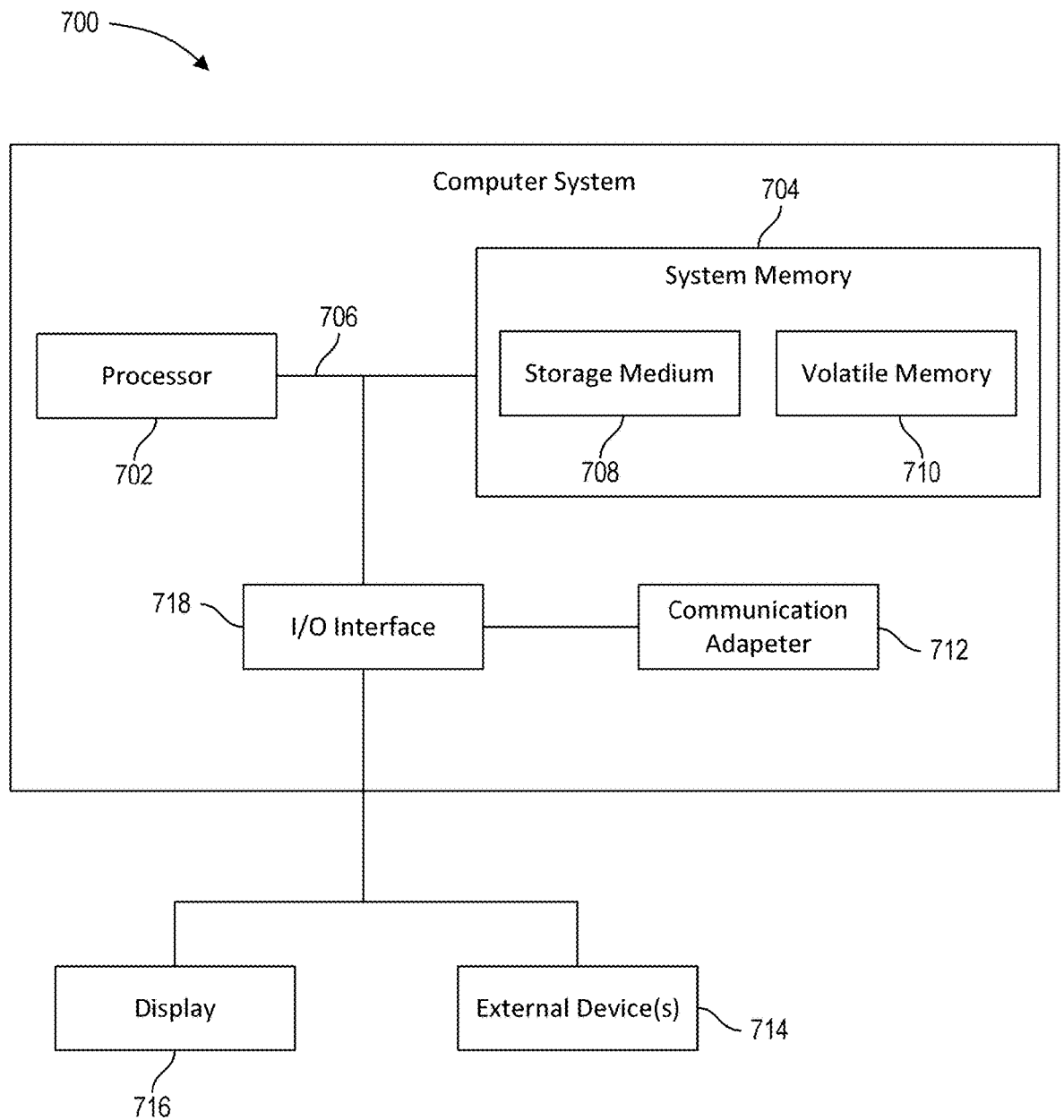
FIG. 57 diagrammatically depicts a computer system in accordance with an exemplary embodiment of the present disclosure.

Referring now to FIG. 57, a computer system 700 is shown in accordance with an exemplary embodiment. The computer system 700 may serve as any computer system disclosed herein (e.g., the computer system 30). As used herein a computer system (or device) is any system/device capable of receiving, processing, and/or sending data. Computer systems include, but are not limited to, microprocessor-based systems, personal computers, servers, hand-held computing devices, tablets, smartphones, multiprocessor-based systems, mainframe computer systems, virtual reality ("VR") headsets and the like.

As shown in FIG. 57, the computer system 700 includes one or more processors or processing units 702, a system memory 704, and a bus 706 that couples the various components of the computer system 700 including the system memory 704 to the processor 702. The system memory 704 includes a computer readable storage medium 708 and volatile memory 710 (e.g., Random Access Memory, cache, etc.). As used herein, a computer readable storage medium includes any media that is capable of storing computer readable; program instructions and is accessible by a processor. The computer readable storage medium 708 includes non-volatile and non-transitory storage media (e.g., flash memory, read only memory (ROM), hard disk drives, etc.). Computer program instructions as described herein include program modules (e.g., routines, programs, objects, components, logic, data structures, etc.) that are executable by a processor. Furthermore, computer readable program instructions, when executed by a processor, can direct a computer system to function in a particular manner such that a computer readable storage medium comprises an article of manufacture. Specifically, the computer readable program instructions when executed by a processor can create a means for carrying out at least a portion of the steps of the methods disclosed herein.

The bus 706 may be one or more of any type of bus structure capable of transmitting data between components of the computer system 700 (e.g., a memory bus, a memory controller, a peripheral bus, an accelerated graphics port, etc.).

The computer system 700 may further include a communication adapter 712 which allows the computer system 700 to communicate with one or more other computer systems/devices via one or more communication protocols (e.g., Wi-Fi, BTLE, etc.) and in some embodiments may allow the computer system 700 to communicate with one or more other computer systems/devices over one or more networks (e.g., a local area network (LAN), a wide area network (WAN), a public network (the Internet), etc.).

In some embodiments, the computer system 700 may be connected to one or more external devices 714 and a display 716. As used herein, an external device includes any device that allows a user to interact with a computer system (e.g., mouse, keyboard, touch screen, etc.). An external device 714 and the display 716 may be in communication with the processor 702 and the system memory 704 via an Input/Output (I/O) interface 718.

The display 716 may display a graphical user interface (GUI) that may include a plurality of selectable icons and/or editable fields. A user may use an external device 714 (e.g., a mouse) to select one or more icons and/or edit one or more editable fields. Selecting an icon and/or editing a field may cause the processor 702 to execute computer readable program instructions stored in the computer readable storage medium 708. In one example, a user may use an external device 714 to interact with the computer system 700 and cause the processor 702 to execute computer readable program instructions relating to at least a portion of the steps of the methods disclosed herein.

Figure 58:
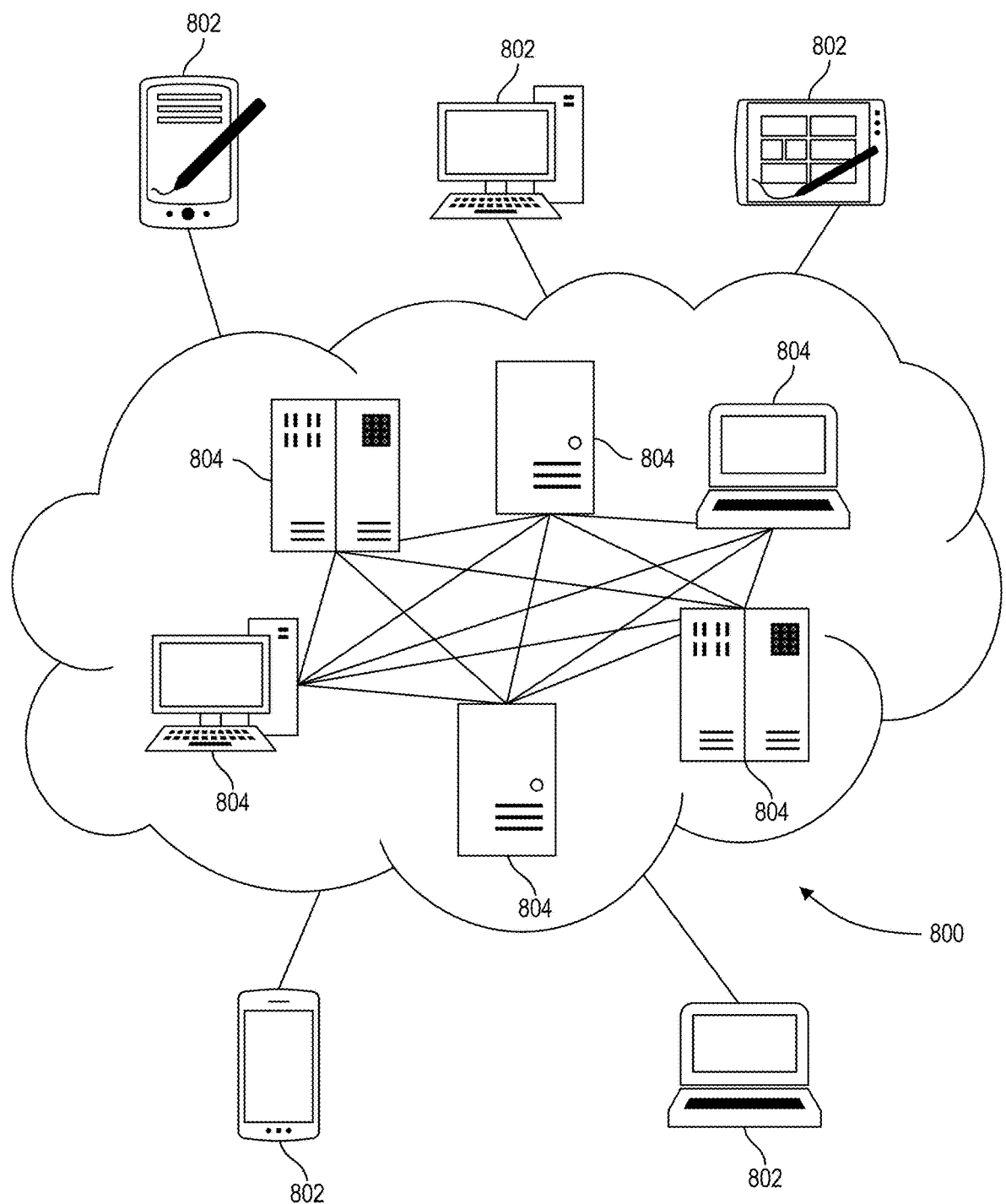
FIG. 58 diagrammatically depicts a cloud computing environment in accordance with an exemplary embodiment of the present disclosure.

Referring now to FIG. 58, a cloud computing environment 800 is depicted in accordance with an exemplary embodiment. The cloud computing environment 800 is connected to one or more user computer systems 802 and provides access to shared computer resources (e.g., storage, memory, applications, virtual machines, etc.) to the user computer systems 802. As depicted in FIG. 58, the cloud computing environment includes one or more interconnected nodes 804. Each node 804 may be a computer system or device local processing and storage capabilities. The nodes 804 may be grouped and in communication with one another via one or more networks. This allows the cloud computing environment 800 to offer software services to the one or more computer services to the one or more user computer systems 802 and as such, a user computer system 802 does not need to maintain resources locally.

In one embodiment, a node 804 includes computer readable program instructions for carrying out various steps of various methods disclosed herein. In these embodiments, a user of a user computer system 802 that is connected to the cloud computing environment may cause a node 804 to execute the computer readable program instructions to carry out various steps of various methods disclosed herein.

Figure 59:
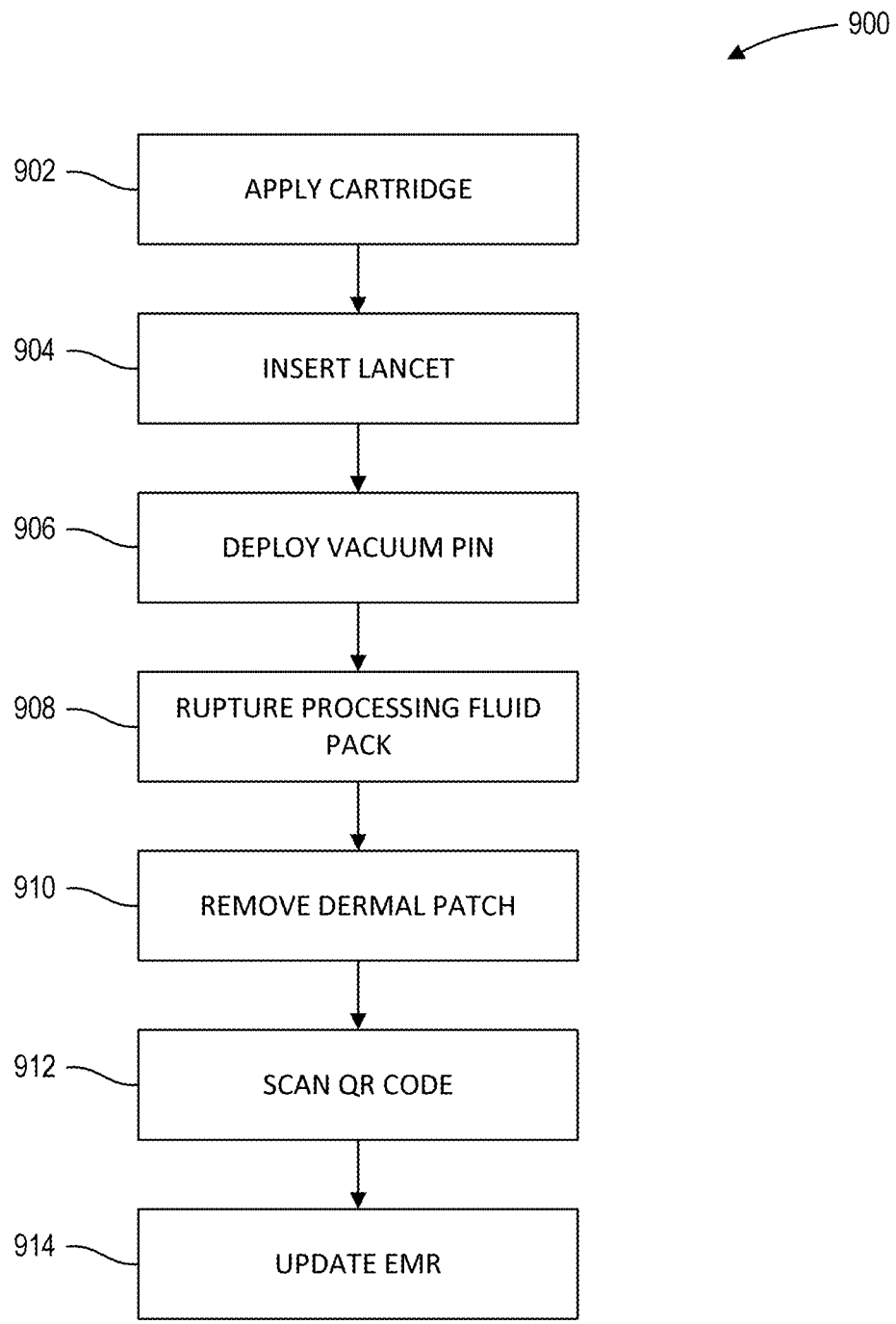
FIG. 59 is a flow chart of a method for running a diagnostic test on a drawn physiological sample in accordance with an exemplary embodiment of the present disclosure.

Referring now to FIG. 59, a method 900 for running a diagnostic test on a drawn physiological sample is shown in accordance with an exemplary embodiment.

At 902, a user (e.g., a medical professional, a subject, etc.) applies the cartridge 12 to the skin of the subject via the adhesive layer 14 at a suitable location (e.g., on a leg, arm, etc.) as previously discussed herein.

At 904, the user inserts the lancet 100 into the cartridge 12 thereby causing the needle 110 of the lancet 100 to draw a physiological sample (e.g., a blood sample, a sample of interstitial fluid, etc.) from the subject as previously discussed herein.

At 906, the user moves the vacuum pin 400 from the undeployed position to the deployed position to draw the drawn physiological sample to the diagnostic test strip 18 as previously discussed herein.

At 908, the user ruptures the processing fluid pack 16 by moving the button 500 from the locked position to the deployed position, wherein the drawn physiological sample interacts with the released processing fluid to form a processed physiological sample as previously discussed herein.

At 910, the user removes the dermal patch system 10 from the skin of the subject and determines the presence or absence of a biomarker in the drawn physiological sample by viewing the test strip as previously discussed herein.

At 912, a user of the computer system 30 scans the QR code 22 and photographs the diagnostic test strip 18 as previously discussed herein.

At 914, the computer system 30 or another computer system that is in communication with the computer system 30 associates the QR code 22 with an EMR 32 and updates the associated EMR 32 to indicate a diagnostic test has been performed on the drawn physiological sample. In one embodiment, the computer system 30 automatically updates the associated EMR 32. In another embodiment, the user of the computer system 30 updates the associated EMR 32. Furthermore, at 914 the user of the computer system 30 photographs the diagnostic test strip 18 and the computer system 30 associates the photograph with the EMR 32 in the EMR database 34. In one embodiment, the computer system 30 or another computer system connected to the EMR database 34 analyzes the photograph to determine the result of the diagnostic test (i.e., the presence or absence of a biomarker in the drawn physiological sample) and updates the associated EMR 32 to include the determined result.

As previously discussed, some of the steps of the various methods disclosed herein may be implemented by way of computer readable instructions, encoded or embedded on computer readable storage medium (which excludes transitory medium), which, when executed by a processor(s), cause the processor(s) to carry out various steps of the methods of the present disclosure.

While various embodiments have been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A system for analyzing a physiological sample, comprising:
   a cartridge configured to attach to the skin of a subject, wherein the cartridge includes:
   a processing fluid pack that is configured to release a processing fluid stored therein,
   a diagnostic test strip, and
   a vacuum pin, and
   a lancet with a needle, wherein the lancet is configured to automatically deploy the needle upon engagement of the lancet with the cartridge to draw a physiological sample from the subject,
   wherein the vacuum pin is configured to create a vacuum within the cartridge to draw the released processing fluid and the drawn physiological sample to the diagnostic test strip.

2. The system of claim 1, wherein the drawn physiological sample and the released processing fluid interact to form a processed physiological sample and the diagnostic test strip is configured to detect a biomarker, when present, within the processed physiological sample.

3. The system of claim 1, wherein the vacuum pin is moveable between an undeployed position and a deployed position and wherein the vacuum pin creates the vacuum within the dermal patch as the vacuum pin moves to the deployed position.

4. The system of claim 3, wherein a strength of the vacuum is based on a distance the vacuum pin moves.

5. The system of claim 3, wherein the cartridge further includes:
a vacuum chamber, wherein the vacuum pin is moveable between the undeployed position and the deployed position within the vacuum chamber.

6. The system of claim 5, wherein the cartridge further includes:
a physiological sample channel in open communication with the vacuum chamber,
wherein the physiological sample channel is configured to carry the drawn physiological sample, and
wherein the vacuum draws the physiological sample to the diagnostic test strip via the physiological sample channel.

7. The system of claim 1, wherein the cartridge further includes:
a moveable button that is configured to compress the processing fluid pack.

8. The system of claim 7, wherein the button is configured to move from a locked position to a deployed position, and wherein the cartridge is configured to prevent the button from compressing the processing fluid pack when the button is in the locked position and is configured to allow the button to compress the processing fluid pack when the button is in the deployed position.

9. The system of claim 8, wherein the cartridge further includes:
a piercing element, and
wherein the button is configured to compress the processing fluid pack into the piercing element to rupture the processing fluid pack.

10. The system of claim 1, wherein the lancet is configured to automatically retract the needle into a housing of the lancet after deployment of the needle.

11. The system of claim 1, wherein the vacuum pin includes an elastomeric O-ring that seals the vacuum pin within the cartridge.

12. The system of claim 1, further comprising:
a computer system configured to image the diagnostic test strip and determine a result of a test associated with the diagnostic test strip based on the image.

13. The system of claim 12, further comprising:
an electronic medical record database that stores a plurality of electronic medical records,
wherein the cartridge further includes a quick response code, and
wherein the computer system is configured to associate the quick response code with an electronic medical record within the electronic medical record database.

14. The system of claim 13, wherein the computer system is configured to:
update the associated electronic medical record with the determined result.

15. The system of claim 1, wherein the processing fluid is a lysing agent.

16. The system of claim 1, wherein the diagnostic test strip is a lateral flow test strip.

17. A cartridge configured to attach to skin of a subject comprising:
a processing fluid pack that is configured to release a processing fluid stored therein,
a diagnostic test strip, and
a vacuum pin, and
a lancet with a needle, wherein the lancet is configured to automatically deploy the needle upon engagement of the lancet with the cartridge to draw a physiological sample from the subject,
wherein the vacuum pin is configured to create a vacuum within the cartridge to draw the released processing fluid and the drawn physiological sample to the diagnostic test strip.

* * * * *